US012604890B2

(12) United States Patent
Wolf et al.

(10) Patent No.: US 12,604,890 B2
(45) Date of Patent: *Apr. 21, 2026

(54) OXYGEN REDUCTION DISPOSABLE KITS, DEVICES AND METHODS OF USE THEREOF

(71) Applicant: Hemanext Inc., Lexington, MA (US)

(72) Inventors: Michael Wolf, Brookline, MA (US); Jancarlo Sarita, Lynn, MA (US); Jeffrey Karl Sutton, Medway, MA (US); Rafael Cordero, Bedford, MA (US); Michael Zocchi, Arlington, MA (US); Philip Keegan, Newton, MA (US); Narendran Renganathan, Plano, TX (US); Robert Harhen, Haverhill, MA (US)

(73) Assignee: Hemanext Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/297,193

(22) Filed: Apr. 7, 2023

(65) Prior Publication Data

US 2023/0247984 A1     Aug. 10, 2023

Related U.S. Application Data

(63) Continuation of application No. 17/749,872, filed on May 20, 2022, now Pat. No. 11,638,421, which is a
(Continued)

(51) Int. Cl.
| *A01N 1/146* | (2025.01) |
| *A01N 1/122* | (2025.01) |
(Continued)

(52) U.S. Cl.
CPC ............. *A01N 1/146* (2025.01); *A01N 1/122* (2025.01); *A61J 1/1468* (2015.05);
(Continued)

(58) Field of Classification Search
CPC .................................. C12M 23/14; A61J 1/10
See application file for complete search history.

(56) References Cited

U.S. PATENT DOCUMENTS

| 3,064,647 A | 11/1962 | Earl |
| 3,361,041 A | 1/1968 | Grob |
(Continued)

FOREIGN PATENT DOCUMENTS

| AU | 2012279043 | 7/2016 |
| CA | 2184868 A1 | 3/1997 |
(Continued)

OTHER PUBLICATIONS

U.S. Appl. No. 62/131,130, filed Mar. 15, 2015, Wolf et al.
(Continued)

*Primary Examiner* — Jonathan M Hurst
(74) *Attorney, Agent, or Firm* — Arnold & Porter Kaye Scholer LLP

(57) ABSTRACT

The present disclosure relates to Oxygen Reduction Disposable kits (ORDKit), devices and methods for the improved preservation of whole blood and blood components. The improved devices and methods for the collection of blood and blood components provide for whole blood and blood components having reduced levels of oxygen. The devices and methods provide for the rapid preparation of deoxygenated blood and blood components for storage that improves the overall quality of the transfused blood and improves health outcomes in patients.

20 Claims, 22 Drawing Sheets

Related U.S. Application Data continuation of application No. 16/375,311, filed on Apr. 4, 2019, now Pat. No. 11,375,709, which is a continuation of application No. 16/052,738, filed on Aug. 2, 2018, now Pat. No. 11,350,626, which is a continuation of application No. 15/459,813, filed on Mar. 15, 2017, now Pat. No. 10,058,091, which is a continuation of application No. PCT/US2016/021794, filed on Mar. 10, 2016.

(60) Provisional application No. 62/131,130, filed on Mar. 10, 2015.

(51) Int. Cl.
    *A61J 1/14*      (2023.01)
    *A61M 1/02*      (2006.01)
    *A61J 1/10*      (2006.01)
    *A61K 35/00*     (2006.01)
    *C12M 1/00*      (2006.01)

(52) U.S. Cl.
    CPC .............. *A61M 1/0272* (2013.01); *A61J 1/10* (2013.01); *A61K 35/00* (2013.01); *A61M 2202/0208* (2013.01); *C12M 23/14* (2013.01)

(56) References Cited

U.S. PATENT DOCUMENTS

| | | | |
|---|---|---|---|
| 3,489,647 A | 1/1970 | Kolobow | |
| 3,668,837 A | 6/1972 | Gross | |
| 3,668,838 A | 6/1972 | McNeil et al. | |
| 3,803,810 A | 4/1974 | Rosenberg | |
| 3,910,841 A | 10/1975 | Esmond | |
| 3,942,529 A | 3/1976 | Waage | |
| 4,075,091 A | 2/1978 | Bellhouse | |
| 4,086,924 A | 5/1978 | Latham, Jr. | |
| 4,093,515 A | 6/1978 | Kolobow | |
| 4,131,200 A | 12/1978 | Rinfret | |
| 4,162,676 A | 7/1979 | Talcott | |
| 4,199,062 A | 4/1980 | Johnston et al. | |
| 4,222,379 A | 9/1980 | Smith | |
| 4,225,439 A | 9/1980 | Spranger | |
| 4,228,032 A | 10/1980 | Talcott | |
| 4,253,458 A | 3/1981 | Bacehowski et al. | |
| 4,256,692 A | 3/1981 | Cover | |
| 4,262,581 A | 4/1981 | Ferrell | |
| 4,300,559 A | 11/1981 | Gajewski et al. | |
| 4,314,480 A | 2/1982 | Becker | |
| 4,342,723 A | 8/1982 | Sado et al. | |
| 4,366,179 A | 12/1982 | Nawata et al. | |
| 4,370,160 A | 1/1983 | Ziemelis | |
| 4,381,775 A | 5/1983 | Nose' et al. | |
| 4,386,069 A | 5/1983 | Estep | |
| 4,398,642 A | 8/1983 | Okudaira et al. | |
| 4,440,815 A | 4/1984 | Zomorodi et al. | |
| 4,455,299 A | 6/1984 | Grode | |
| 4,540,416 A | 9/1985 | Hattori et al. | |
| 4,568,328 A | 2/1986 | King et al. | |
| 4,572,899 A | 2/1986 | Walker et al. | |
| 4,579,223 A | 4/1986 | Otsuka et al. | |
| 4,585,735 A | 4/1986 | Meryman et al. | |
| 4,609,383 A | 9/1986 | Bonaventura et al. | |
| 4,629,544 A | 12/1986 | Bonaventura et al. | |
| 4,639,353 A | 1/1987 | Takemura et al. | |
| 4,654,053 A | 3/1987 | Sievers et al. | |
| 4,659,549 A | 4/1987 | Hamada et al. | |
| 4,670,013 A | 6/1987 | Barnes et al. | |
| 4,701,267 A | 10/1987 | Watanabe et al. | |
| 4,713,176 A | 12/1987 | Schoendorfer et al. | |
| 4,731,978 A | 3/1988 | Martensson | |
| 4,748,121 A | 5/1988 | Beaver et al. | |
| 4,749,551 A | 6/1988 | Borgione | |
| 4,769,175 A | 9/1988 | Inoue | |
| 4,769,318 A | 9/1988 | Hamasaki et al. | |
| 4,798,728 A | 1/1989 | Sugisawa | |
| 4,828,561 A | 5/1989 | Woodroof | |
| 4,837,047 A | 6/1989 | Sato et al. | |
| 4,859,360 A | 8/1989 | Suzuki et al. | |
| 4,861,867 A | 8/1989 | Estep | |
| 4,880,548 A | 11/1989 | Pall et al. | |
| 4,880,786 A | 11/1989 | Sasakawa et al. | |
| 4,898,573 A * | 2/1990 | Takenaka .................. A61J 1/10<br>604/6.02 | |
| 4,902,701 A | 2/1990 | Batchelor et al. | |
| 4,925,572 A | 5/1990 | Pall | |
| 4,986,837 A | 1/1991 | Shibata | |
| 4,998,990 A | 3/1991 | Richter et al. | |
| 5,000,848 A | 3/1991 | Hodgins et al. | |
| 5,023,054 A | 6/1991 | Sato et al. | |
| 5,037,419 A | 8/1991 | Valentine et al. | |
| 5,120,659 A | 6/1992 | King et al. | |
| 5,137,531 A | 8/1992 | Lee et al. | |
| 5,139,668 A | 8/1992 | Pan et al. | |
| 5,143,763 A | 9/1992 | Yamada et al. | |
| 5,152,905 A | 10/1992 | Pall et al. | |
| 5,192,320 A | 3/1993 | Anazawa et al. | |
| 5,194,158 A | 3/1993 | Matson | |
| 5,208,335 A | 5/1993 | Ramprasad et al. | |
| 5,229,012 A | 7/1993 | Pall et al. | |
| 5,254,248 A | 10/1993 | Nakamura et al. | |
| 5,286,407 A | 2/1994 | Inoue et al. | |
| 5,328,268 A | 7/1994 | LaFleur | |
| 5,353,793 A | 10/1994 | Bornn | |
| 5,356,375 A | 10/1994 | Higley | |
| 5,360,734 A | 11/1994 | Chapman et al. | |
| 5,362,442 A | 11/1994 | Kent | |
| 5,368,808 A | 11/1994 | Koike et al. | |
| 5,382,526 A | 1/1995 | Gajewski et al. | |
| 5,386,014 A | 1/1995 | Nho et al. | |
| 5,387,624 A | 2/1995 | Morita et al. | |
| 5,417,986 A | 5/1995 | Reid et al. | |
| 5,427,663 A | 6/1995 | Austin et al. | |
| 5,443,743 A | 8/1995 | Gsell | |
| 5,449,617 A | 9/1995 | Falkenberg et al. | |
| 5,476,764 A | 12/1995 | Bitensky | |
| 5,506,141 A | 4/1996 | Weinreb et al. | |
| 5,529,821 A | 6/1996 | Ishikawa et al. | |
| 5,605,934 A | 2/1997 | Giertych | |
| 5,617,873 A | 4/1997 | Yost et al. | |
| 5,624,794 A | 4/1997 | Bitensky et al. | |
| 5,635,358 A | 6/1997 | Wilding et al. | |
| 5,686,304 A | 11/1997 | Codner | |
| 5,691,452 A | 11/1997 | Gawryl et al. | |
| 5,693,122 A | 12/1997 | Berndt | |
| 5,693,230 A | 12/1997 | Asher | |
| 5,698,250 A | 12/1997 | DelDuca et al. | |
| 5,709,472 A | 1/1998 | Prusik et al. | |
| 5,730,989 A | 3/1998 | Wright | |
| 5,744,056 A | 4/1998 | Venkateshwaran et al. | |
| 5,750,115 A | 5/1998 | Van Den Bosch | |
| 5,783,094 A | 7/1998 | Kraus et al. | |
| 5,783,148 A | 7/1998 | Cottingham et al. | |
| 5,789,151 A | 8/1998 | Bitensky et al. | |
| 5,789,152 A | 8/1998 | Black et al. | |
| 5,811,142 A | 9/1998 | DelDuca et al. | |
| 5,846,427 A | 12/1998 | Kessler et al. | |
| 5,858,015 A | 1/1999 | Fini | |
| 5,858,643 A | 1/1999 | Ben-Hur et al. | |
| 5,863,460 A | 1/1999 | Slovacek et al. | |
| 5,895,810 A | 4/1999 | Light et al. | |
| 5,902,747 A | 5/1999 | Nemser et al. | |
| 5,906,285 A | 5/1999 | Slat | |
| 5,928,178 A | 7/1999 | Samolyk | |
| 5,955,519 A | 9/1999 | Neri | |
| 5,962,650 A | 10/1999 | Osterberg et al. | |
| 5,972,710 A | 10/1999 | Weigl et al. | |
| 6,007,529 A | 12/1999 | Gustafsson et al. | |
| 6,027,623 A | 2/2000 | Ohkawa | |
| 6,042,264 A | 3/2000 | Prusik et al. | |
| 6,045,701 A | 4/2000 | Ung-Chhun et al. | |
| 6,047,203 A | 4/2000 | Sackner et al. | |
| 6,068,152 A | 5/2000 | Meiners et al. | |
| 6,076,664 A | 6/2000 | Yeager | |

(56) References Cited

U.S. PATENT DOCUMENTS

| | | | |
|---|---|---|---|
| 6,080,322 A | 6/2000 | Deniega et al. |
| 6,090,062 A | 7/2000 | Sood et al. |
| 6,097,293 A | 8/2000 | Galloway et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,287,284 B1 | 9/2001 | Woarburton-Pitt |
| 6,287,289 B1 | 9/2001 | Niedospial, Jr. |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,479,252 B1 | 11/2002 | Barbera-Guillem et al. |
| 6,482,585 B2 | 11/2002 | Dottori |
| 6,494,909 B2 | 12/2002 | Greenhalgh |
| 6,527,957 B1 | 3/2003 | Denienga et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 8,877,508 B2 | 11/2014 | Hyde et al. |
| 8,887,721 B2 | 11/2014 | Zapol et al. |
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 | 10/2017 | Yoshida et al. |
| 9,844,615 B2 | 12/2017 | Yoshida et al. |
| 10,058,091 B2 | 8/2018 | Wolf et al. |
| 10,295,781 B2 | 5/2019 | Park et al. |
| 10,603,417 B2 | 3/2020 | Yoshida et al. |
| 10,849,824 B2 | 12/2020 | Yoshida et al. |
| 11,350,626 B2 | 6/2022 | Wolf et al. |
| 11,375,709 B2 | 7/2022 | Wolf et al. |
| 11,638,421 B2 | 5/2023 | Wolf et al. |
| 12,201,584 B2 | 1/2025 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1 | 2/2003 | Ng et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0146671 A1 | 7/2004 | Szabo et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0207186 A1 | 9/2007 | Scanlon et al. |
| 2007/0240569 A1 | 10/2007 | Ooya |
| 2007/0276508 A1 | 11/2007 | Fischer et al. |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2008/0299538 A1 | 12/2008 | Goodrich et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |

(56)                References Cited

U.S. PATENT DOCUMENTS

| | | |
|---|---|---|
| 2010/0282662 A1 | 11/2010 | Lee et al. |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004586 A1 | 1/2013 | Vachon et al. |
| 2013/0004937 A1 | 1/2013 | Yoshida et al. |
| 2013/0144266 A1 | 6/2013 | Borenstein et al. |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0091047 A1 | 4/2014 | Radwanski et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |
| 2018/0087997 A1 | 3/2018 | Thenard et al. |
| 2018/0094269 A1 | 4/2018 | Miller et al. |
| 2019/0275152 A1 | 9/2019 | Sowemimo-Coker et al. |
| 2021/0100721 A1 | 4/2021 | Yoshida et al. |
| 2025/0268792 A1 | 8/2025 | Yoshida et al. |

FOREIGN PATENT DOCUMENTS

| | | |
|---|---|---|
| CA | 2477946 | 9/2003 |
| CN | 1195965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 102711865 A | 10/2012 |
| CN | 103732056 | 4/2014 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 245 217 A2 | 10/2002 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | S57-3652 A | 1/1982 |
| JP | 58-194879 | 11/1983 |
| JP | 59-115349 | 7/1984 |
| JP | 61-109577 A | 5/1986 |
| JP | 63-63616 A | 3/1988 |
| JP | 01-013860 | 3/1989 |
| JP | 01-104271 A | 4/1989 |
| JP | 3-284263 | 12/1991 |
| JP | H 04-364850 | 12/1992 |
| JP | 5-503075 A | 5/1993 |
| JP | 5-503304 A | 6/1993 |
| JP | H05-148151 A | 6/1993 |
| JP | H05-237162 | 9/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | H 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |
| JP | 2001-523225 | 11/2001 |
| JP | 2002-087971 | 3/2002 |
| JP | 2002-253936 A | 9/2002 |
| JP | 2002-541941 | 12/2002 |
| JP | 2003-010287 | 1/2003 |
| JP | 2004-089495 A | 3/2004 |
| JP | 2004-244044 | 9/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-518952 | 6/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-535235 | 11/2010 |
| JP | 2010-538735 | 12/2010 |
| JP | 2011 000132 A | 1/2011 |
| JP | 2011-92905 | 5/2011 |
| JP | 2011-516570 A | 5/2011 |
| JP | 2013-500794 | 1/2013 |
| JP | 2013-507226 | 3/2013 |
| JP | 2014-501501 | 1/2014 |
| JP | 2014-518283 | 7/2014 |
| JP | 2014-527436 | 10/2014 |
| JP | 2007-509206 A | 4/2017 |
| JP | A 2018/512970 | 5/2018 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/36330 A1 | 7/1999 |
| WO | WO 1999/48963 A2 | 9/1999 |
| WO | WO 2000/011946 A2 | 3/2000 |
| WO | WO 2000/0062891 | 10/2000 |
| WO | WO 01/10470 A1 | 2/2001 |
| WO | WO 2002/043485 | 6/2002 |
| WO | WO 2002/096471 | 12/2002 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006/050328 A1 | 5/2006 |
| WO | WO 2006/057473 A1 | 6/2006 |
| WO | WO 2006/088455 A1 | 8/2006 |

(56)                References Cited

FOREIGN PATENT DOCUMENTS

| | | |
|---|---|---|
| WO | WO 2008/063868 | 5/2008 |
| WO | WO 2009/126786 A2 | 10/2009 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/006238 | 1/2014 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |
| WO | WO 2017/205590 A2 | 11/2017 |

OTHER PUBLICATIONS

U.S. Appl. No. 62/151,957, filed Apr. 23, 2015, Yoshida et al.
U.S. Appl. No. 12/901,350, filed Oct. 8, 2010, Yoshida et al.
Agarwal et al., "Effect of pre-storage gamma irradiation on red blood cells," *Indian Journal of Medical Research* 122(5):385 (2005).
Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).
Apstein et al., "Effect of erythrocyte storage and oxyhemoglobin affinity changes on cardiac function," *Am J. Physiol* 248: H508-15 (1985).
Aydogan et al., "Impaired erythrocytes deformability in $H(2)O(2)$-induced oxidative stress: protective effect of L-carnosine," *Clin Hemorheol Microcirc* 39: 93-8 (2008).
Babic, "In vitro function and phagocytosis of galactosylated platelet concentrates after longterm refrigeration," *Transfusion* 47: 442-51 (2007).
Barbee et al., "The Fahraeus Effect," *Microvascular Research*, 3:6-16 (1971).
Barclay et al., "A Method for Detecting Chaos in Canine Myocardial Microcirculatory Red Cell Flux," *Microcirculation*, 7(5):335-346 (2000).
Bardy et al., "Technetium-99m Labeling by Means of Stannous Pyrophosphate: Application to Bleomycin and Red Blood Cells," *Journal of Nuclear Medicine*, 16(5):435-437 (1975).
Barras et al., "Influence of Rejuvenation on the Rheological Properties of Stored Erythrocytes," *VASA*, 23(4):305-311 (1994) (with translation).
Basu et al., "Overview of blood components and their preparation," Indian J Anaesth 58:529-537 (2014).
Becker et al., "Studies of platelet concentrates stored at 22 C and 4 C," *Transfusion* 13: 61-8 (1973).
Benesch et al., "The effect of organic phosphates from the human erythrocyte on the allosteric properties of hemoglobin," *Biochem Biophys Res Commun* 26: 162-7 (1967).
Bensinger et al., "Prolonged maintenance of 2,3-DPG in liquid blood storage: Use of an internal CO.sub.2 trap to stabilize pH," *J. Lab. Clin. Med.*, 89(3):498-503 (1977).
Benson et al., "Accumulation of Pro-Cancer Cytokines in the Plasma Fraction of Stored Packed Red Cells," *J Gastrointest Surg.*, 16:460-468 (2012).
Bersin et al., "Importance of oxygen-haemoglobin binding to oxygen transport in congestive heart failure," *Br Heart J* 70: 443-7 (1993).

Beutler et al., "Storage of red cell concentrates in CPD-A2 for 42 and 49 days," *The Journal of Laboratory and Clinical Medicine*, 102(1):53-62 (1983).
Bordbar et al., "Identified metabolic signature for assessing red blood cell unit quality is associated with endothelial damage markers and clinical outcomes," *Transfusion* 56: 852-62 (2016).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Browne et al., "The molecular pathobiology of cell membrane iron: the sickle red cell as a model" *Free Radic Biol Med* 24: 1040-8 (1998).
Browne et al., "Removal of erythrocyte membrane iron in vivo ameliorates the pathobiology of murine thalassemia," *J Clin Invest* 100: 1459-64 (1997).
Bryant et al., "Pathogen Inactivation The Definitive Safeguard for the Blood Supply," *Arch Pathol Lab Med* 131:719-733 (2007).
Burns et al., "Anaerobic Storage Improves the Mechanical Properties of Stored Red Blood Cells," *Transfusion* 52: 83A (2012).
Burns et al., "Artificial microvascular network: a new tool for measuring rheologic properties of stored red blood cells," *Transfusion*, 52(5):1010-1023 (2012).
Burns et al., "Deterioration of red blood cell mechanical properties is reduced in anaerobic storage," *Blood Transfus* 14: 80-8 (2016).
Buskirk et al., "Accumulation of Biologic Response Modifiers During Red Blood Cell Cold Storage," *Transfusion*, 49(Suppl3): 102A-103A (2009).
Cabrales et al., "Microvascular pressure and functional capillary density in extreme hemodilution with low-and high-viscosity dextran and a low-viscosity Hb-based 02 carrier," *American Journal of Physiology-Heart and Circulatory Physiology* 287: H363-H73 (2004).
Cabrales et al., "Plasma viscosity regulates systemic and microvascular perfusion during acute extreme anemic conditions," *Am J. Physiol Heart Circ Physiol* 291: H2445-52 (2006).
Cannon et al., "Damage control resuscitation in patients with severe traumatic hemorrhage: A practice management guideline from the Eastern Association for the Surgery of Trauma," *J Trauma Acute Care Surg* 82: 605-17 (2017).
Cap et al., "Whole Blood Transfusion," *Military Medicine* 183, 9/10:44 (2018).
Cardo et al., "Pathogen inactivation of *Leishmania donovani infantum* in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Chanutin et al., "Effect of organic and inorganic phosphates on the oxygen equilibrium of human erythrocytes," *Arch Biochem Biophys* 121: 96-102 (1967).
Chaplin et al., "The Proper Use of Previously Frozen Blood Cells for Transfusion," *Blood*, 59:1118-1120 (1982).
Chatpun et al., "Cardiac mechanoenergetic cost of elevated plasma viscosity after moderate hemodilution," *Biorheology* 47: 225-37 (2010).
Chatpun et al., "Cardiac systolic function recovery after hemorrhage determines survivability during shock," *J Trauma* 70: 787-93 (2011).
Chatpun et al., "Effects of plasma viscosity modulation on cardiac function during moderate hemodilution," *Asian J Transfus* Sci 4: 102-8 (2010).
Chilton et al., "Privacy Protection of Health Information: Patient Rights and Pediatrician Responsibilities," *Pediatrics*, 104(4):973-977 (1999).
Choi et al., "Influence of storage temperature on the responsiveness of human platelets to agonists," *Ann Clin Lab Sci* 33: 79-85 (2003).

(56) References Cited

OTHER PUBLICATIONS

Chouchani et al., "Ischaemic accumulation of succinate controls reperfusion injury through mitochondrial ROS," *Nature* 515: 431-5 (2014).

Coene, "Paired analysis of plasma proteins and coagulant capacity after treatment with three methods of pathogen reduction," *Transfusion* 54: 1321-31 (2014).

Cognasse et al., "The role of microparticles in inflammation and transfusion: A concise review," *Transfus. Apher. Sci.* 53(2):159-167 (2015).

Cokelet et al., "Fabrication of in Vitro Microvascular Blood Flow Systems by Photolithography," *Microvascular Research*, 46:394-400 (1993).

Corbin, "Pathogen Inactivation of Blood Components: Current Status and Introduction of an Approach Using Riboflavin as a Photosensitizer," *International Journal of Hematology* Supplement II 76:253-257 (2002).

Cotton et al., "A Randomized Controlled Pilot Trial of Modified Whole Blood Versus Component Therapy in Severely Injured Patients Requiring Large Volume Transfusions," *Annals of Surgery* 258(4) (2013).

Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).

D'Alessandro et al., "Heterogeneity of blood processing and storage additives in different centers impacts stored red blood cell metabolism as much as storage time: lessons from REDS-11I-Omics," *Transfusion* 59: 89-100 (2019).

D'Alessandro et al., "Time-course investigation of SAGM-stored leukocyte-filtered red blood cell concentrates: from metabolism to proteomics," *Haematologica* 97: 107-15 (2012).

D'Alessandro et al., "Red blood cell metabolism under prolonged anaerobic storage," *Mol Biosyst* 9: 1196-209 (2013).

D'Alessandro et al., "Red blood cell metabolic responses to refrigerated storage, rejuvenation, and frozen storage," *Transfusion* 57: 1019-30 (2017).

D'Alessandro et al., "Metabolomics of AS-5 RBC supernatants following routine storage," *Vox Sang* (2014).

D'Alessandro et al., "An update on red blood cell storage lesions, as gleaned through biochemistry and omics technologies," *Transfusion* 55: 205-19 (2015).

D'Alessandro et al., "Red blood cell storage and clinical outcomes: new insights," *Blood Transfus* 15: 101-3 (2017).

D'Alessandro et al., "Plasma succinate is a predictor of mortality in critically injured patients," *Journal of Trauma and Acute Care Surgery* 83: 491-5 (2017).

D'Alessandro et al., "Plasma First Resuscitation Reduces Lactate Acidosis, Enhances Redox Homeostasis, Amino Acid and Purine Catabolism in a Rat Model of Profound Hemorrhagic Shock," *Shock* 46: 173-82 (2016).

D'Alessandro et al., "Anaerobic storage Condition enhances GSH Levels while Maintaining Pentose Phosphate Pathway Activity," *Transfusion* 56: 51A (2016).

D'Alessandro et al., "Red blood cell storage in additive solution-7 preserves energy and redox metabolism: a metabolomics approach," *Transfusion* 55: 2955-66 (2015).

D'Alessandro et al., "Routine storage of red blood cell (RBC) units in additive solution-3: a comprehensive investigation of the RBC metabolome," *Transfusion* 55: 1155-68 (2015).

D'Alessandro et al., "Omics markers of the red cell storage lesion and metabolic linkage," *Blood Transfus* 15: 137-44 (2017).

D'Alessandro et al., "AltitudeOmics: Red Blood Cell Metabolic Adaptation to High Altitude Hypoxia," *J Proteome Res* 15: 3883-95 (2016).

D'Alessandro et al., "Citrate metabolism in red blood cells stored in additive solution-3," *Transfusion* 57: 325-36 (2017).

D'Alessandro et al., "Metabolic effect of alkaline additives and guanosine/gluconate in storage solutions for red blood cells," *Transfusion* 58: 1992-2002 (2018).

D'Alessandro et al., "Effects of aged stored autologous red blood cells on human plasma metabolome," *Blood Adv* 3: 884-96 (2019).

D'Alessandro et al., "Hitchhiker's guide to the red cell storage galaxy: Omics technologies and the quality issue," *Transfus Apher Sci* 56: 248-53 (2017).

D'Amici, et al., "Red blood cell storage in SAGM and AS3: a comparison through the membrane two-dimensional electrophoresis proteome," *Blood Transfusion = Trasfusione del sangue* 10 Suppl 2: s46-54 (2012).

De Angelis et al., "Erythrocyte Shape Control in Stored Blood: The Effect of Additive Solutions on Shape Recovery," *Haematologica*, 73:7-12 (1988).

Deible et al., "Molecular barriers to biomaterial thrombosis by modification of surface proteins with polyethylene glycol," *Biomaterials*, 19:1885-1893 (1998).

De Korte et al., "Prolonged maintenance of 2,3-diphosphoglycerate acid and adenosine triphosphate in red blood cells during storage," *Transfusion*, 48:1081-1089 (2008).

De Venuto et al., "Rejuvenation of Human Red Blood Cells During Liquid Storage," *Transfusion*, 14(4):338-344 (1974).

Delgado et al., "Platelet Function in Stored Whole Blood Measured by a Shear- and Von Willebrand Factor-Dependent Methodology is Retained During Storage at 4° C. for up to 7 Days," *Transfusion* 51: 65A (2011).

Dennis et al., "Transfusion of 2,3 DPG-enriched red blood cells to improve cardiac function," *Ann Thorac Surg* 26: 17-6 (1978).

Dennis et al., "Improved myocardial performance following high 2-3 diphosphoglycerate red cell transfusions," *Surgery* 77: 741-7 (1975).

De Wolski et al., "Metabolic pathways that correlate with post-Transfusion circulation of stored murine red blood cells," *Haematologica* 101: 578-86 (2016).

Dumaswala et al., "Studies in Red Blood Cell Preservation: 9. The Role of Glutamine in Red Cell Preservation," *Vox Sang*, 67:255-259 (1994).

Dumaswala et al., "Glutamine- and Phosphate-Containing Hypotonic Storage Media Better Maintain Erythrocyte Membrane Physical Properties," *Blood*, 88(2):697-704 (1996).

Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).

Dumont et al., "Anaerobic storage of red blood cells in a novel additive solution improves in vivo recovery," *Transfusion*, 49(3):458-464 (2009).

Dumont et al., "Performance Of Anaerobic Stored Red Blood Cells Prepared Using A Prototype 02 & CO2 Depletion And Storage System," *Transfusion* 51s: SP89 (2011).

Dumont et al., "Randomized cross-over in vitro and in vivo evaluation of a prototype anaerobic conditioning and storage system vs. standard aerobic storage," *Vox Sang* 103: 123 (2012).

Dumont et al., "$CO_2$-dependent metabolic modulation in red cells stored under anaerobic conditions," *Transfusion* 56(2): 392-403 (2016)(epub 2015).

Dupont, "What is Tyvek(R)," downloaded from www.dupont.com/what-is-tyvek.html.

Durapore® Membrane Filters—Filter Discs and Membranes, retrieved on Aug. 26, 2014, from: www.emdmillipore.com/US/en/product/Durapore.

Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).

Erickson et al., "Evaluation of in vitro Quality of Stored RBC after Treatment with S303 Pathogen Inactivation at Varying Hematocrits," *Transfusion DUP—General Collection* 48(2) Supplement (2008).

European Search Report completed on Feb. 11, 2005, in European Patent Application No. 02 78 2307.9.

European Search Report Jun. 18, 2019, in European Patent Application No. 19163305.6.

Extended European Search Report, dated Aug. 29, 2014 for European Patent Application No. 10823965.8.

Extended European Search Report dated Oct. 30, 2014 in European Patent Application No. 11838889.1.

(56)　　　　　References Cited

OTHER PUBLICATIONS

Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Extended European Search Report dated Oct. 9, 2018, in European Patent Application No. 16784043.8.
Extended European Search Report dated Apr. 16, 2019, in European Patent Application No. 16845192.0.
Extended European Search Report dated Jun. 5, 2019, in European Patent Application No. 19158815.1.
Extended European Search Report dated Feb. 21, 2022 in European Patent Application No. 21199989.1.
Ezuki et al., "Survival and recovery of apheresis platelets stored in a polyolefin container with high oxygen permeability," *Vox Sanguinis* 94:292-298 (2008).
Fahraeus et al., "The Viscosity of the Blood in Narrow Capillary Tubes," *Am. J. Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Farber et al., "Effect of decreased 02 affinity of hemoglobin on work performance during exercise in healthy humans," *J Lab Clin Med* 104: 166-75 (1984).
Fast et al., "Inactivation of Human White Blood Cells in Red Blood Cell Products Using the MIRASOL® System for Whole Blood," *Blood* Abstract #2897 110(11)(pt. 1) (2007).
Fatouros et al., "Recombinant factor VII SQ—influence of oxygen, metal ions, pH and ionic strength on its stability in aqueous solution," *International Journal of Pharmaceutics*, 155(1):121-131 (1997).
Feys, "Oxygen removal during pathogen inactivation with riboflavin and UV light preserves protein function in plasma for Transfusion," *Vox Sang* 106: 307-15 (2013).
Frame et al., "A System for Culture of Endothelial Cells in 20-50-μm Branching Tubes," *Microcirculation*, 2(4):377-385 (1995).
"Friction Factor for Flow in Coils and Curved Pipe," Neutrium Available on the world wide web at neutrium.net/fluid flow/friction-factor-for-flow-in-coils-and-curved-pipe/ (2017).
Friesenecker et al., "Arteriolar vasoconstrictive response: comparing the effects of arginine vasopressin and norepinephrine," *Crit Care* 10: R75 (2006).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gardner, "Problems of Multiple Transfusions," *Official Journal of the California Medical Associate*, 83(2):93-97 (1958).
Gehrke et al., "Metabolomics evaluation of early-storage red blood cell rejuvenation at 4 degrees C and 37 degrees C," *Transfusion* 58: 1980-91 (2018).
Gevi et al., "Alterations of red blood cell metabolome during cold liquid storage of erythrocyte concentrates in CPD-SAGM," *J Proteomics* 76 Spec No. 168-180 (2012).
Gifford et al., "Parallel Microchannel-Based Measurements of Individual Erythrocyte Areas and Volumes," *Biophysical Journal*, 84:623-633 (2003).
Gifford et al., "A detailed study of time-dependent changes in human red blood cells: from reticulocyte maturation to erythrocyte senescence," *British Journal of Haematology*, 135:395-404 (2006).
Golan et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 (1990).
Goodrich, "The Use of Riboflavin for the Inactivation of Pathogens in Blood Products," *Vox Sanguinis* Suppl. 2 78:211-215 (2000).
Green et al., "10. Liposomal Vaccines," Immunobiology of Proteins and Peptides VII, Plenum Press, New York, pp. 83-92 (1995).
Greenwalt et al., "Studies In Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Haddaway et al., "Hemostatic properties of cold-stored whole blood leukoreduced using a platelet-sparing versus a non-platelet-sparing filter," *Transfusion* (2019).
Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).
Hebbel, et al., Oxidation-induced changes in microrheologic properties of the red blood cell membrane. *Blood* 1990;76: 1015-20.
Hebbel, "Auto-oxidation and a membrane-associated 'Fenton reagent': a possible explanation for development of membrane lesions in sickle erythrocytes," *Clin Haematol* 14: 129-40 (1985).
Henschler et al., "Development of the S-303 Pathogen Inactivation Technology for Red Blood Cell Concentrates," *Transfusion Medicine and Hemotherapy* 38(1):33-42 (2011).
Hershko, "Mechanism of iron toxicity and its possible role in red cell membrane damage," *Semin Hematol* 26: 277-85 (1989).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hess et al., "Advances in military, field, and austere Transfusion medicine in the last decade," *Transfus Apher Sci* 49: 380-6 (2013).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C.," *Vox Sang.*, 51:27-34 (1986).
Högman et al., "Effects of oxygen and mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).

(56)                References Cited

OTHER PUBLICATIONS

Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Hornsey et al., "Cold storage of pooled, buffy-coat-derived, leucoreduced platelets in plasma," *Vox Sang* 95 26-32 (2008).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/US2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (mailed Nov. 26, 2012).
International Search Report for PCT/US2016/021794 dated Jul. 18, 2016.
International Search Report for PCT/US2016/033151 dated Oct. 13, 2016.
International Search Report for PCT/US2016/051115 dated Nov. 21, 2016.
International Search Report for PCT/US2017/034410 dated Dec. 22, 2017.
International Search Report for PCT/US2020/057754 dated Feb. 15, 2021.
Irsch et al., "Pathogen inactivation of platelet and plasma blood components for transfusion using the INTERCEPT Blood SystemTM," *Transfusion Medicine and Hemotherapy*, 38:19-31 (2011).
Jagannathan et al., "Oxidative stress under ambient and physiological oxygen tension in tissue culture," *Curr Pharmacol Rep* 2: 64-72 (2016).
Jain et al., "Determinants of Leukocyte Margination in Rectangular Microchannels," *PLoS ONE*, 4(9):1-8 (2009).
Janetzko et al., "Pathogen reduction technology (Mirasol®) treated single donor platelets resuspended in a mixture of autologous plasma and PAS," *Vox Sanguinis* 97:234-239 (2009).

Jarman et al., "Rural risk: Geographic disparities in trauma mortality," *Surgery* 160: 1551-9 (2016).
Jarolim et al., "Effect of hemoglobin oxidation products on the stability of red cell membrane skeletons and the associations of skeletal proteins: correlation with a release of them in," *Blood* 76: 2125-31 (1990).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jenkins et al., "Trauma hemostasis and oxygenation research position paper on remote damage control resuscitation: definitions, current practice, and knowledge gaps," *Shock* 41 Suppl 1: 3-12 (2014).
Jesch et al., "Oxygen dissociation after Transfusion of blood stored in ACD or CPD solution," *J Thorac Cardiovasc Surg* 70: 35-9 (1975).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Jobes et al., "Toward a definition of "fresh" whole blood: an in vitro characterization of coagulation properties in refrigerated whole blood for Transfusion," *Transfusion* 51: 43-51 (2011).
Johnson et al., "Regulation of blood flow in single capillaries," *American Journal of Physiology*, 212:1405-1415 (1967).
Jy et al., "Release of Microparticles During Blood Storage Is Influenced by Residual Platelets, Leukocytes and Oxygen Levels," *Blood* 120: 3435 (2012).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kerger et al., "Systemic and subcutaneous microvascular pO2 dissociation during 4-h hemorrhagic shock in conscious hamsters," *Am J. Physiol* 270: H827-H36 (1996).
Khorana et al., "Blood Transfusions, thrombosis, and mortality in hospitalized patients with cancer," *Arch Intern Med* 168: 2377-81 (2008).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Kohli et al., "Packed red cells versus whole blood transfusion for severe paediatric anemia, pregnancy-related anemia and obstetric bleeding: an analysis of clinical proactive guidelines from sub-Saharan Africa and evidence underpinning recommendations," *Tropical Medicine and International Health* 24(1):11-22 (2019).
Korsten et al., "Determination of %502 in More Than 1300 Fresh Erythrocyte Concentrates by Resonance Raman Spectroscopy," *Transfusion* 58: 215A (2018).
Kotwal et al., "The Effect of a Golden Hour Policy on the Morbidity and Mortality of Combat Casualties," *JAMA Surg* 151: 15-24 (2016).
Kreuger et al., "A clinical evaluation of citrate-phosphate-dextrose-adenine blood," *Vox Sang* 29: 81-9 (1975).

(56) References Cited

OTHER PUBLICATIONS

Krogh, "Studies on the physiology of capillaries. II. The reactions to local stimuli of the blood-vessels in the skin and web of the frog," *The Journal of Physiology*, 55:412-422 (1921).

Kuraoka, et al., "Ship-in-a-bottle synthesis of a cobalt phthalocyanine/porous glass composite membrane for oxygen separation," *Journal of Membrane Science*, 286(1-2):12-14 (2006).

Kwan et al., "Microfluidic analysis of cellular deformability of normal and oxidatively damaged red blood cells," *Am J Hematol* 88: 682-9 (2013).

Kynar Flex Product Catalog, downloaded May 20, 2015 from Kynar.com.

Liu et al., "Beneficial Role of Erythrocyte Adenosine A2B Receptor-Mediated AMP-Activated Protein Kinase Activation in High-Altitude Hypoxia," *Circulation* 134: 405-21 (2016).

Lowndes, "Blood Interference in fluorescence spectrum: Experiment, analysis and comparison with intraoperative measurements on brain tumor," *Bachelor Thesis*, Linköping University, pp. 1-42 (2010).

Lozono et al., "Pathogen inactivation: coming of age," *Curr Opin Hematol* 20(6):540-545 (2013).

Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).

Lundblad, "Factor VIII—Reducing agents, copper ions, and stability," http://lundbladbiotech.com.

Manno et al., "Comparison of the hemostatic effects of fresh whole blood, stored whole blood, and components after open heart surgery in children," *Blood* 77: 930-6 (1991).

Mazor et al., "Prolonged Storage of Red Cells: The Effect of pH, Adenine Phosphate," *Vox Sanguinis*, 66:264-269 (1994).

McDonald et al., "Poly(dimethylsiloxane) as a Material for Fabricating Microfluidic Devices," *Accounts of Chemical Research*, 35(7):491-499 (2002).

Meryman et al., "Prolonged storage of red cells at 4° C.," *Transfusion*, 26(6):500-505 (1986).

Meryman et al., "Extending the storage of red cells at 4° C.," *Transfus. Sci.*, 15(2):105-115 (1994).

Miller, "New evidence in trauma resuscitation-is 1: 1: 1 the answer?" *Perioperative medicine* 2: 13 (2013).

Moll et al., "Dean vortices applied to membrane process. Part II: Numerical approach," *Journal of Membrane Science*, 288:321-335 (2007).

Mollison, "The Introduction of Citrate as an Anticoagulant for Transfusion and of Glucose as a Red Cell Preservative," *British Journal of Haematology* 108:1318 (2000).

Moroff et al., "Factors Influencing Changes in pH during Storage of Platelet Concentrates at 20-24° C.," *Vox Sanguinis*, 42(1):33-45 (1982).

Moroff et al., "Proposed standardization of methods for determining the 24-hour survival of stored red cells," *Transfusion*, 24:109-114 (1984).

Moroff et al., "Concepts about current conditions for the preparation and storage of platelets," *Transfus Med Rev* V(1):48-59 (1991).

Mufti, "Treatment of whole blood (WB) and red blood cells (RBC) with S-303 inactivates pathogens and retains in vitro quality of stored RBC," *Biologicals* 38:14-19 (2010).

Murphy et al., "Platelet storage at 22° C.: role of gas transport across plastic containers in maintenance of viability," *Blood* 46(2):209-218 (1975).

Murphy et al., "Increased Mortality, Postoperative Morbidity, and Cost After Red Blood Cell Transfusion in Patients Having Cardiac Surgery," *Circulation*, 116:2544-2552 (2007).

Musante et al., "Active Focal Segmental Glomerulosclerosis is Associated with Massive Oxidation of Plasma Albumin," *Journal of the American Society of Nephrology*, 18(3):799-810 (2007).

Mussano et al., "Cytokine, chemokine and growth factor profile of Platelet Rich Plasma," *Universita Degli Studi Di Tornio* 2016.

Nair et al., "Cold-Stored Platelets in PAS Exhibit Superior Hemostatic Potential" *Blood* 126: 772 (2015) Abstract.

Nemkov et al., "Metabolomics in Transfusion medicine," *Transfusion* 56: 980-93 (2015).

Nemkov et al., "Hypoxia modulates the purine salvage pathway and decreases red blood cell and supernatant levels of hypoxanthine during refrigerated storage," *Haematologica* 103: 361-72 (2018).

Nemkov et al., "Metabolism of Citrate and Other Carboxylic Acids in Erythrocytes As a Function of Oxygen Saturation and Refrigerated Storage," *Front Med (Lausanne)* 4: 175 (2017).

Nessen et al., "Fresh whole blood use by forward surgical teams in Afghanistan is associated with improved survival compared to component therapy without platelets," *Transfusion* 53:107S-113S (2013).

Ng et al., "Components for integrated poly(dimethylsiloxane) microfluidic systems," *Electrophoresis*, 23:3461-3473 (2002).

Nilsson et al., "Association between venous thromboembolism and perioperative allogeneic Transfusion," *Arch Surg* 142: 126-32; discussion 33 (2007).

Ohkuma et al., "The preservative-exchange method using a sextuple-bag system for a 10-week storage period of red blood cells," *Transfusion Medicine*, 1:257-262 (1991).

"Oxygen O2 in Blood," downloaded from http://web.utk.edu/~rstrange/wfs550/index2.html (2022).

Paglia et al., "Biomarkers defining the metabolic age of red blood cells during cold storage," *Blood* 128: e43-50 (2016).

Paillous et al. "Mechanisms of photosensitized DNA cleavage," *J. Photochem. Photobiol. B: Biol.* 20:203-209 (1993).

Pallotta et al., "Storing red blood cells with vitamin C and N-acetylcysteine prevents oxidative stress-related lesions: a metabolomics overview," *Blood Transfus* 12: 376-87 (2014).

Pallotta et al., "Supplementation of anti-oxidants in leucofiltered erythrocyte concentrates: assessment of morphological changes through scanning electron microscopy," *Blood Transfus* 12: 421-4 (2014).

Parkkinen et al., "Plasma ascorbate protects coagulation factors against photooxidation," *Thromb Haemost* 75(2):292-297 (1996).

Peirce et al., "The Membrane Lung: Studies with a New High Permeability Co-Polymer Membrane," *Trans. Amer. Soc. Artif. Int. Organs* vol. XIV:220-226 (1968).

Pelletier et al., "Pathogen inactivation techniques," *Best Practice & Research Clinical Haematology* 19(1):205-242 (2006).

Picker et al., "Current methods for the reduction of blood-borne pathogens: a comprehensive literature review," *Blood Transfusion* 11:343-348 (2013).

Pidcoke et al., "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).

Pidcoke et al., "Primary hemostatic capacity of whole blood: a comprehensive analysis of pathogen reduction and refrigeration effects over time," *Transfusion* 53:137S-149S (2013).

Poncelet et al., "Tips and tricks for flow cytometry-based analysis and counting of microparticles," *Transfus. Apher. Sci.* 53(2):110-126 (2015).

Poxton, "Antibodies to lipopolysaccharide," *Journal of Immunological Methods*, 186:1-15 (1995).

Prefiltration before membrane filtration, hydrophobic, 25 μm 142 mm, retrieved on Aug. 26, 2014, from: www.emdmillipore.com/US/en/product/Prefiltration-before-membrane-filtration.

Pries et al., "Biophysical aspects of blood flow in the microvasculature," *Cardiovascular Research*, 32:654-667 (1996).

Prowse et al., "Commercially available blood storage containers," *Vox Sanguinis* 106(1): 1-13 (2014).

Prudent, et al., "Oxygen in Red Blood Cell Concentrates Influence of Donor's Characteristics, Location and Blood Processing," *Vox Sang* 113: 116 (2018).

Przepiorka et al. "Use of Irradiated Blood components: Practice Parameter," *Am J Clin Pathol* 106(1):6-11 (1996).

Ramstack et al., "Shear-induced activation of platelets," *J. Biomech.*, 12:113-125 (1979).

(56)        References Cited

OTHER PUBLICATIONS

Reisz et al., "Red blood cells in hemorrhagic shock: a critical role for glutaminolysis in fueling alanine transamination in rats," *Blood Advances* 1:1296-305 (2017).

Reisz et al., "Methylation of protein aspartates and deamidated asparagines as a function of blood bank storage and oxidative stress in human red blood cells," *Transfusion* 58: 2978-91 (2018).

Reisz et al., "Metabolic Linkage and Correlations to Storage Capacity in Erythrocytes from Glucose 6-Phosphate Dehydrogenase-Deficient Donors," *Front Med* (*Lausanne*) 4: 248 (2017).

Reisz et al., "Oxidative modifications of glyceraldehyde 3-phosphate dehydrogenase regulate metabolic reprogramming of stored red blood cells," *Blood* 128: e32-42 (2016).

Reynolds et al., "S-nitrosohemoglobin deficiency: A mechanism for loss of physiological activity in banked blood," *Proceedings of the National Academy of Sciences*, 104(43):17058-17062 (2007).

Risbano et al., "Effects of Aged Stored Autologous Red Blood Cells on Human Endothelial Function," *Am J Respir Crit Care Med* 192: 1223-33 (2015).

Rock et al., "Nutricel as an additive solution for neonatal transfusion," *Transfusion Science*, 20:29-36 (1999).

Rolfsson et al., "Metabolomics comparison of red cells stored in four additive solutions reveals differences in citrate anticoagulant permeability and metabolism," *Vox Sang* (2017).

Sambuceti et al., "Why should we study the coronary microcirculation?," *Am J Physiol Heart Circ Physiol*, 279:H2581-H2584 (2000).

Schubert et al., "Whole blood treated with riboflavin and ultraviolet light: Quality assessment of all blood components produced by the buffy coat method," *Transfusion* 55(4):815-823 (2014).

Scott et al., "Effect of excess alpha-hemoglobin chains on cellular and membrane oxidation in model beta-thalassemic erythrocytes," *J Clin Invest* 91: 1706-12 (1993).

Seghatchian et al., "Pathogen-reduction systems for blood components: The current position and future trends," *Transfusion and Apheresis Science* 35:189-196 (2006).

Seghatchian, "Pathogen inactivation of whole blood and red cell components: An overview of concept, design, developments, criteria of acceptability and storage lesion," *Transfusion and Apheresis Science* 49:357-363 (2013).

Seok et al., "Genomic responses in mouse models poorly mimic human inflammatory diseases," *Proceedings of the National Academy of Sciences* 110: 3507-12 (2013).

Sivertsen et al., "Preparation of leukoreduced whole blood for Transfusion in austere environments; effects of forced filtration, storage agitation, and high temperatures on hemostatic function," *J Trauma Acute Care Surg* 84: S93-S103 (2018).

Shalev et al., "Extremely high avidity association of Fe(III) with the sickle red cell membrane," *Blood* 88: 349-52 (1996).

Shapiro, "To filter blood or universal leukoreduction: what is the answer?," *Critical Care* 8(Suppl 2): S27-draftS30 (2004).

Sheffield et al., "Changes in coagulation factor activity and content of di(2-ethylhexyl) phthate in frozen plasma units during refrigerated storage for up to 5 days after thawing," *Transfusion*, 52:494-502 (2012).

Shevkoplyas et al., "Direct measurement of the impact of impaired erythrocyte deformability on microvascular network perfusion in a microfluidic device," *Lab Chip*, 6:914-920 (2006).

Shimizu et al., "Multicenter Clinical Evaluation of Red Cell Concentrates Stored up to 6 Weeks in MAP, a new additive solution," *Japanese Journal of Clinical Hematology*, 33(2):148-156 (1992) (with translation).

Skalak et al., "Deformation of Red Blood Cell in Capillaries," *Science*, 164(3880):717-719 (1969).

Snyder et al., "In vitro and in vivo evaluation of a whole blood platelet-sparing leukoreduction filtration system," *Transfusion* 50: 2145-51 (2010).

Sohmer et al., "Phosphoenolypyruvate (PEP) Effects on Fresh and Stored Red Blood Cells," *Proceedings of the Society for Experimental Biology and Medicine*, 171:24-33 (1982).

Spinella et al., "Prehospital hemostatic resuscitation to achieve zero preventable deaths after traumatic injury," *Curr Opin Hematol* (2017).

Spinella et al., "Whole blood: back to the future," *Curr Opin Hematol* 23: 536-42 (2016).

Spinella et al., "Whole blood for hemostatic resuscitation of major bleeding," *Transfusion* 56:S190-S202 (2016).

Steurer et al., "Trauma and Massive Blood Transfusions," *Curr. Anesthesiol. Rep* 4:200-208 (2014).

Strandenes et al., "Emergency Whole-Blood Use in the Field: a Simplified Protocol for Collection and Transfusion," *SHOCK* 41(Suppl 1):76-83 (2014).

Strandenes et al., "Low Titer Group O Whole Blood in Emergency Situations," *SCHOCK* 41(Suppl 1): 70-75 (2014).

Su et al., "Impermeable barrier films and protective coatings based on reduced graphene oxide," *Nature Communications* 5 Article No. 4843 (2014).

Sun et al., "Purinergic control of red blood cell metabolism: novel strategies to improve red cell storage quality," *Blood Transfus* 15: 535-42 (2017).

Sun et al., "Sphingosine-1-phosphate promotes erythrocyte glycolysis and oxygen release for adaptation to high-altitude hypoxia," *Nat Commun* 7: 12086 (2016).

Supplementary European Search Report dated Jan. 20, 2015 in European Patent Application No. 12822378.2.

Sutera et al., "Deformation and Fragmentation of Human Red Blood Cells in Turbulent Shear Flow," *Biophys. J.*, 15:1-10 (1975).

Sutton et al., "A Novel Instrument for Studying the Flow Behaviour of Erythrocytes through Microchannels Simulating Human Blood Capillaries," *Microvascular Research*, 53:272-281 (1997).

Szymanski et al., "Effect of rejuvenation and frozen storage on 42-day-old AS-1 RBCs," *Transfusion*, 41:550-555 (2001).

Tannahill et al., "Succinate is an inflammatory signal that induces IL-lbeta through HIF-lalpha" *Nature* 496: 238-42 (2013).

Teisseire et al., "Induced low P50 in anesthetized rats: blood gas, circulatory and metabolic adjustments," *Respir Physiol* 58: 335-44 (1984).

Tinmouth et al., "The Clinical Consequences of the Red Cell Storage Lesion," *Transfusion Medicine Reviews*, 15(2):91-107 (2001).

Tolinski, "Getting the Most out of Polypropylene, Polythylene and TPO," *Additives for Polyolefins*, Second Edition 2015.

Tracey et al., "A Silicon Micromachined Device for Use in Blood Cell Deformability Studies," *IEEE Transactions on Biomedical Engineering*, 42(8):751-761 (1995).

"Transition and Turbulence," https://www.princeton.edu/~asmits/Bicycle_web/transition.html. Adapted from The Engine and the Atmosphere: An Introduction to Engineering by Z. Warhaft, Cambridge University Press, (1997).

Tsai et al., "Microvascular perfusion upon exchange Transfusion with stored red blood cells in normovolemic anemic conditions," *Transfusion* 44: 1626-34 (2004).

Tsantes et al., "Redox imbalance, macrocytosis, and RBC homeostasis," *Antioxid Redox Signal* 8: 1205-16 (2006).

Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).

Valeri et al., "Improved oxygen delivery to the myocardium during hypothermia by perfusion with 2,3 DPG-enriched red blood cells," *Am Thorac Surg* 30: 527-35 (1980).

Valeri, "Circulation and hemostatic effectiveness of platelets stored at 4 C or 22 C: studies in aspirintreated normal volunteers," *Transfusion* 16: 20-3 (1976).

Valeri, "Hemostatic effectiveness of liquid-preserved and previously frozen human platelets," *N Engl J Med* 290: 353-8 (1974).

Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).

(56) References Cited

OTHER PUBLICATIONS

Van Buskirk et al., "Comparison of Cytokine, Cell-free Hemoglobin, and Isoprostane Accumulations in Packed Red Blood Cells During Novel Anaerobic and Conventional Cold Storage," Transfusion 54S: SP53 (2014).

Van Buskirk et al., "Comparison of microparticles production in packed red blood cells stored under anaerobic and conventional cold storage condition," Vox Sang 105 (S1): 150 (2007).

Van Buskirk et al., "Evaluation of Select Red Blood Cell Biochemical and Coagulation Properties in Whole Blood Stored Using a Novel Anaerobic Storage Platform," Transfusion 56: 54A (2016).

Van der Meer et al., "Platelet preservation: Agitation and containers," Transfusion and Apheresis Science 44:297-304 (2011).

Van Slyke, "An Apparatus for Determination of the Gases in Blood and Other Solutions," Chemistry 7:229-231 (1921).

Voigt et al., "Effects of a restrictive Blood Transfusion protocol on acute pediatric burn care: Transfusion threshold in pediatric burns," J Trauma Acute Care Surg 85: 1048-54 (2018).

Vrielink et al., "Transfusion-transmissible infections," Current Opinion in Hematology 5:396-405 (1998).

Wallvik et al., "Platelet Concentrates Stored at 22° C. Need Oxygen the Significance of Plastics in Platelet Preservation," Vox Sanguinis, 45(4):303-311 (1983).

Wallvik et al., "The platelet storage capability of different plastic containers," Vox Sanguinis, 58(1):40-44 (1990).

Wang et al., "Fabrication of PLGA microvessel scaffolds with circular microchannels using soft lithography," Journal of Micromechanics and Microengineering, 17(10):2000-2005 (2007).

Wang et al., "The contribution of oxidative stress to platelet senescence during storage" Transfusion (2019).

Weinberg et al., "Transfusions in the Less Severely Injured: Does Age of Transfused Blood Affect Outcomes?," The Journal of Trauma, 65(4):794-798 (2008).

Wilding et al., "Manipulation and Flow of Biological Fluids in Straight Channels Micromachined in Silicon," Clinical Chemistry, 40(1):43-47 (1994).

Williams, "Blood Transfusion on Cruise Ships; A 36 Month Review of Preliminary Data," THOR Trauma Hemostasis & Oxygenation Research Network, RDCR Symposium, Bergen (2013).

Williams et al., "Transfusion of Anaerobically Stored Red Blood Cells Improves Recovery in Experimental Rat Hemorrhagic Shock Model," Transfusion 57: 33A (2017).

Williams et al., "Transfusion of Anaerobically Stored Red Blood Cells Improves Recovery in Experimental Rat Hemorrhagic Shock Model," Shock Abstract (2019).

Winter, "Red blood cell in vitro quality and function is maintained after S-303 pathogen inactivation treatment," Transfusion 54:1798-1807 (2014).

Wolfe et al., "Molecular defect in the membrane skeleton of blood bank-stored red cells. Abnormal spectrin-protein 4.1-actin complex formation," J Clin Invest 78: 1681-6 (1986).

Wolfe, "Oxidative injuries to the red cell membrane during conventional blood preservation," Semin Hematol 26: 307-12 (1989).

Wood et al., "The Viability of Human Blood Stored in Phosphate Adenine Media," Transfusion 7, 401-408 (1967).

Woodson, "Functional consequences of altered blood oxygen affinity," Acta Biol Med Ger 40: 733-6 (1981).

Wu et al., "Polymer microchips bonded by $O_2$-plasma activation," Electrophoresis, 23:782-790 (2002).

Yalcin et al., "Increased hemoglobin 02 affinity protects during acute hypoxia," Am J. Physiol Heart Circ Physiol 303: H271-81 (2012).

Yazer et al., "Coagulation factor levels in plasma frozen within 24 hours of phlebotomy over 5 days of storage at 1 to 6° C.," Transfusion, 48:2525-2530 (2008).

Yhap et al., "Decreased oxygen uptake with stored blood in the isolated hindlimb" J Appl Physiol 38: 882-885 (1975).

Yoshida et al., "Extended storage of red blood cells under anaerobic conditions," Vox Sanguinis, 92:22-31 (2007).

Yoshida et al., "Storage of red blood cells under anaerobic conditions: reply," Vox Sanguinis, 93:184 (2007).

Yoshida et al., "The effects of additive solution pH and metabolic rejuvenation on anaerobic storage of red cells," Transfusion, 48:2096-2105 (2008).

Yoshida et al., "Anaerobic storage of red blood cells," Blood Transfus, 8:220-236 (2010).

Yoshida et al., "Oxygen content—uncontrolled and overlooked parameter associated with stored red cell concentrate: Unexpectedly wide distribution," Vox Sang 112: P-244 (2017) Abstract.

Yoshida et al., "Enhancing uniformity and overall quality of red cell concentrate with anaerobic storage," Blood Transfus 15: 172-81 (2017).

Yoshida et al., "Toward a comprehensive biochemical model of human erythrocyte: relationship between metabolic and osmotic state of the cell and the state of hemoglobin," Prog Clin Biol Res 319: 179-93; discussion 94-6 (1989).

Yoshida et al., "Unexpected Variability of Hemoglobin Oxygen Saturation in Packed Red Blood Cells upon Donation Suggests Uncontrolled and Overlooked Parameter Associated with the Development of the Storage Lesion," Transfusion 57 (2017).

Yoshida et al., "Red blood cell storage lesion: causes and potential clinical consequences" Blood Transfus 17: 27-52 (2019).

Yoshida et al., "Reduction of Microparticle Generation During Anaerobic Storage of Red Blood Cells," Transfusion 52: 83A (2012).

Yuasa et al., "Improved extension of platelet storage in a polyolefin container with higher oxygen permeability," British Journal of Hematology 126:153-159 (2004).

Zaroulis, et al., "Lactic acidemia in baboons after Transfusion of red blood cells with improved oxygen transport function and exposure to severe arterial hypoxemia," Transfusion 19: 420-5 (1979).

Zavizion et al., "Inactivation of mycoplasma species in blood by Inactine PEN110 process," Transfusion 44:286-293 (2004).

Zhang et al., "Modification of Si(100) surface by the grafting of poly(ethylene glycol) for reduction in protein adsorption and platelet adhesion," J Biomed Mater Res, 56:324-332 (2001).

Zielinski et al., "Back to the future: The renaissance of whole-blood transfusions for massively hemorrhaging patients," Surgery 155(5) 883-886 (2014).

Zielinski, et al., "Prehospital Blood Transfusion programs: Capabilities and lessons learned," J Trauma Acute Care Surg 82: S70-s8 (2017).

Zimrin et al., "Current issues relating to the transfusion of stored red blood cells," Vox Sanguinis, 96:93-103 (2009).

Zimring et al., "Established and theoretical factors to consider in assessing the red cell storage lesion," Blood, 125:2185-2190 (2015).

Zingarelli et al., "Part I: Minimum Quality Threshold in Preclinical Sepsis Studies (MQTiPSS) for study design and humane modeling endpoints," Shock 51: 10-22 (2019).

Zink et al., "Noninvasive Evaluation of Active Lower Gastrointestinal Bleeding: Comparison Between Contrast-Enhanced MDCT and 99mTcLabeled RBC Scintigraphy," American Journal of Roentgenology 191: 1107-14 (2008).

Zinkham et al., "Carboxyhemoglobin levels in an unstable hemoglobin disorder (Hb Zurich): effect on phenotypic expression," Science 209: 406-8 (1980).

Zolla et al., "Classic and alternative red blood cell storage strategies: seven years of '-omics' investigations," Blood Transfus 13:21-31 (2015).

U.S. Appl. No. 15/459,813, filed Mar. 15, 2017, which issued as U.S. Pat. No. 10,058,091 on Aug. 28, 2018.

U.S. Appl. No. 16/052,738, filed Aug. 2, 2018, which issued as U.S. Pat. No. 11,350,626 on Jun. 7, 2022.

U.S. Appl. No. 16/375,311, filed Apr. 4, 2019, which issued as U.S. Pat. No. 11,375,709 on Jul. 5, 2022.

U.S. Appl. No. 17/749,872, filed May 20, 2022, which issued as U.S. Pat. No. 11,638,421 on May 2, 2023.

* cited by examiner

| | R-SLO | SLO | PF96 | 3D |
|---|---|---|---|---|
| Kinetic Rate (min$^{-1}$) | -0.769 x10$^{-02}$ | -1.32 x10$^{-02}$ | -0.99 x10$^{-02}$ | -1.65 x10$^{-02}$ |

| Blood Volume (ml) | 176 | 220 | 250 | 270 | 300 | 350 |
|---|---|---|---|---|---|---|
| Kinetic Rate (min$^{-1}$) | $-1.05 \times 10^{-02}$ | $-0.86 \times 10^{-02}$ | $-0.94 \times 10^{-02}$ | $-0.85 \times 10^{-02}$ | $-0.73 \times 10^{-02}$ | $-0.79 \times 10^{-02}$ |

| Blood Volume (ml) | 95 | 110 | 220 | 300 | 360 |
|---|---|---|---|---|---|
| Kinetic Rate (min$^{-1}$) | -1.39x10$^{-02}$ | -1.90x10$^{-02}$ | -0.82 x10$^{-02}$ | -0.56 x10$^{-02}$ | -0.32 x10$^{-02}$ |

| | PSU+PE | PSU+ClearFoil | Double-sided PSU | Double-sided PVDF |
|---|---|---|---|---|
| Kinetic Rate (min$^{-1}$) | -0.65 x10$^{-02}$ | -0.548 x10$^{-02}$ | -1.42 x10$^{-02}$ | -1.55 x10$^{-02}$ |

OXYGEN REDUCTION DISPOSABLE KITS, DEVICES AND METHODS OF USE THEREOF

CROSS REFERENCE TO RELATED APPLICATION

This application is a continuation of U.S. application Ser. No. 17/749,872, filed May 20, 2022 (now U.S. Pat. No. 11,638,421, issued May 2, 2023), which is a continuation of U.S. application Ser. No. 16/375,311, filed Apr. 4, 2019 (now U.S. Pat. No. 11,375,09, issued Jul. 5, 2022), which application is a continuation of U.S. application Ser. No. 16/052,738, filed Aug. 2, 2018 (now U.S. Pat. No. 11,350, 626, issued Jun. 7, 2022), which is a continuation of U.S. application Ser. No. 15/459,813, filed Mar. 15, 2017 (now U.S. Pat. No. 10,058,091, issued Aug. 28, 2018), which is a continuation of PCT Application No. PCT/US2016/021794 filed Mar. 10, 2016, which claims benefit of U.S. Provisional Application No. 62/131,130 filed Mar. 10, 2015, each of which is hereby incorporated by reference.

FIELD OF THE INVENTION

The present disclosure relates to Oxygen Reduction Disposable kits (ORDKit), devices and methods for the improved preservation of whole blood and blood components. More particularly, the disclosure relates to the improved devices and methods for the collection of blood and blood components to provide whole blood and blood components having reduced levels of oxygen. The methods, devices and kits of the present disclosure provide for improved quality of blood and blood components for transfusion and improved patient safety and outcome.

BACKGROUND OF THE INVENTION

The supplies of liquid blood and blood components are currently limited by storage systems used in conventional blood storage practices. Using current systems, stored blood expires after a period of about 42 days of refrigerated storage at a temperature above freezing (i.e., 4° C.) as packed blood cell preparations. For Example, the World Health Organization (WHO) estimates more than 100 million units of blood are collected and stored globally each year. In the US alone, there were 13.6 million units of red blood cells (RBCs) collected in 2013 according to the American Association of Blood Bankers. During refrigerated storage, RBCs become progressively damaged by storage lesions. When transfused within the current 6-week limit, stored RBCs have lower quality as well as potential toxicity, which can be manifested as side effects of transfusion therapy. Among the observed storage lesions are altered biochemical and physical parameters associated with stored red blood cells. Examples of these alterations include in vitro measured parameters such as reduced metabolite levels (adenosine triphosphate (ATP) and 2,3 diphosphoglycerate (2,3-DPG)), increased levels of cell-free iron, hemolysis, increased levels of microparticles, reduced surface area, echinocytosis, phosphatidylserine exposure, and reduced deformability. Expired blood cannot be used and must be discarded because it may harm the ultimate recipient. These reasons and others limit the amount of readily available high quality blood needed for transfusions.

When stored conventionally, stored blood undergoes a steady deterioration which is associated with hemolysis, hemoglobin degradation and reduced ATP and 2,3-DPG concentrations. When transfused into a patient, the effects of the steady deterioration during storage manifest, for example, as a reduction in the 24-hour in vivo recovery. Red blood cells stored for an extended period of time under conventional conditions deteriorate and up to 25% may be removed by the recipient's body shortly after transfusion. Non-viable RBCs cause iron overload in chronically transfused patients. Hemoglobin in RBCs does not release oxygen efficiently at tissues due to loss of 2,3-DPG. RBCs are not able to enter and perfuse capillary beds due to loss of deformability. Storage lesions in transfused blood may lead to major organ failure in the lungs, heart, kidney, liver, and central nervous system, among others. Storage lesions in transfused blood may be associated with increased morbidity.

Transfusing RBCs stored under conventional conditions for longer periods may result in higher morbidity and longer hospital stays compared to transfusing "fresher" red cells. Higher morbidity and longer hospital stays result with RBCs that are stored longer than 3 weeks, in comparison to fresher red cells. For example, negative clinical outcomes in cardiac surgery occur when using "older" blood, multiple organ failure in surgical patients is related to the age of transfused red cells, correlations exist between older units and increased mortality in severe sepsis, failure to improve $O_2$ utilization is attributed to decreased 2,3-DPG, and decreased cardiac index is associated with increased blood viscosity.

In addition to immediate removal by the recipient of certain RBCs, consequences of RBC storage lesions include: (i) depletion of ATP (loss of RBC's ability to dilate the pre-capillary arteriole); (ii) depletion of 2,3-DPG; (iii) accumulation of oxidative damage caused by reactive oxygen species (ROS) formed by the reaction of denatured hemoglobin with $O_2$; and (iv) decreased RBC deformability and increased RBC viscosity, caused in part by oxidative damage to membrane and cytoskeleton. Less deformable RBCs are excluded from capillary channels resulting in low capillary occupancy and reduced tissue perfusion. Massive transfusion of cells with reduced deformability may also contribute to multiple organ failure by blocking the organs' capillary beds. After transfusion, 2,3-DPG is synthesized relatively quickly in vivo to ~50% of the normal level in as little as 7 hours and to ~95% of the normal level in 2-3 days. However, since 2,3-DPG-depleted cells do not recover their levels immediately, $O_2$-carrying capacity is compromised to the detriment of critically ill patients requiring immediate $O_2$ delivery and tissue perfusion. There are numerous reports that emphasize the importance of RBCs with high oxygen carrying capacity in such clinical situations.

The transfusion of red blood cells (RBCs) is a life-saving therapy aimed at improving oxygenation of the tissues and vital end organs in severely anemic patients. The majority of RBC units used for transfusion are stored at 1-6° C. for up to 42 days in an oxygen-permeable polyvinylchloride blood bag that contains additive/preservative solution.

Storage of frozen blood is known in the art, but such frozen blood has limitations. For a number of years, frozen blood has been used by blood banks and the military for certain high-demand and rare types of blood. However, frozen blood is difficult to handle. It must be thawed then cryoprotectant must be gradually washed away which makes it impractical for emergency situations. Once blood is thawed, it must be used within 48 hours. U.S. Pat. No. 6,413,713 to Serebrennikov is directed to a method of storing blood at temperatures below 0° C.

U.S. Pat. No. 4,769,318 to Hamasaki et al. and U.S. Pat. No. 4,880,786 to Sasakawa et al. are directed to additive solutions for blood preservation and activation. U.S. Pat. No. 5,624,794 to Bitensky et al., U.S. Pat. No. 6,162,396 to Bitensky et al., and U.S. Pat. No. 5,476,764 to Bitensky are directed to the storage of red blood cells under oxygen-depleted conditions. U.S. Pat. No. 5,789,151 to Bitensky et al. is directed to blood storage additive solutions. For example, Rejuvesol (available from Citra Lab LLC, Braintree, MA) is added to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells.

U.S. Pat. No. 4,837,047 to Sato et al. relates to a container for storing blood for a long period of time to keep the quality of the blood in good condition.

Traditional manual blood collection is performed by a trained phlebotomist using a blood collection kit that includes, at a minimum, a blood collection bag, a phlebotomy needle, and tubing sufficient to connect the needle to the blood collection bag containing anticoagulant. Typically, a blood collection bag further includes an anticoagulant solution but an anticoagulant solution may alternatively be supplied in a separate bag or container connected to the blood collection bag with suitable tubing. None of the components of current commercial systems provide for, or include, the reduction of oxygen.

There is a need to begin the reduction of oxygen from blood prior to storage at the time of collection. In order to accomplish the blood reduction within the existing infrastructure and within the time periods as limited by current regulatory regimes, it is desirable to begin oxygen reduction as early as possible, preferably at collection before the temperature of the collected blood has been significantly reduced.

SUMMARY OF THE INVENTION

The present disclosure provides for, and includes, an oxygen depletion device for depleting oxygen from blood prior to anaerobic storage comprising an outer receptacle substantially impermeable to oxygen, an inner collapsible blood container comprising one or more chambers that are permeable to oxygen, and an oxygen sorbent situated within said outer receptacle.

The present disclosure provides for, and includes, an oxygen depletion device for depleting oxygen from whole blood prior to anaerobic storage comprising an outer receptacle substantially impermeable to oxygen, an inner collapsible blood container comprising one or more chambers that are permeable to oxygen, and an oxygen sorbent situated within said outer receptacle.

The present disclosure provides for, and includes, an oxygen depletion device for depleting oxygen from packed red blood cells prior to anaerobic storage comprising an outer receptacle substantially impermeable to oxygen, an inner collapsible blood container comprising one or more chambers that are permeable to oxygen, and an oxygen sorbent situated within said outer receptacle.

The present disclosure provides for, and includes, a method to prepare blood for storage comprising providing an oxygen depletion device comprising an outer receptacle substantially impermeable to oxygen, an inner collapsible blood container enclosed within the outer receptacle, and an oxygen sorbent situated between the outer receptacle and inner blood compatible blood container, flowing the blood into the inner collapsible blood container of the oxygen depletion device and producing oxygen-reduced blood having less than 20% oxygen saturation.

The present disclosure provides for, and includes, a method to prepare blood for storage comprising providing an oxygen depletion device comprising an outer receptacle substantially impermeable to oxygen, an inner collapsible blood container enclosed within the outer receptacle, and an oxygen sorbent situated between the outer receptacle and inner blood compatible blood container, flowing the blood into the inner collapsible blood container of the oxygen depletion device and producing oxygen-reduced blood having less than 10% oxygen saturation.

The present disclosure provides for, and includes, a blood storage device for storing oxygen depleted blood comprising an outer receptacle substantially impermeable to oxygen; an inner collapsible blood container comprising a locating feature adapted to align the collapsible blood container within the geometry of the outer receptacle; at least one inlet comprising tubing connecting to the collapsible blood container and a bond to the outer receptacle, wherein the bond to the outer receptacle is substantially impermeable to oxygen; and an oxygen sorbent situated within the outer receptacle.

The present disclosure provides for, and includes, an oxygen depletion device 10 for depleting oxygen from blood prior to anaerobic storage comprising an outer receptacle 101 substantially impermeable to oxygen; an oxygen indicator 206, a spacer material 110, and about 80 grams of an oxygen sorbent 103 in between an outer receptacle 101 and a 15 μm to 200 μm thick silicone collapsible blood container 102.

The present disclosure provides for, and includes, an oxygen depletion device 10 for depleting oxygen from blood prior to anaerobic storage comprising an outer receptacle 101 substantially impermeable to oxygen; an oxygen indicator 206, a spacer material 110, and about 80 grams of an oxygen sorbent 103 in between an outer receptacle 101 and a collapsible blood container 102 prepared from PVDF having a 0.2 μm pore size. The present disclosure provides for methods to prepare blood for storage comprising: providing an oxygen depletion device 10 and flowing blood into the inner collapsible blood container 102, agitating the oxygen depletion device 10 for up to 3 hours, producing oxygen-reduced blood having less than 20% oxygen saturation, and transferring the oxygen-reduced blood to a blood storage device 20. The method further provides for the production of oxygen-reduced blood having less than 20% oxygen saturation in less than 8 hours after collection from a donor. In a further embodiment, the agitating is nutating.

The present disclosure provides for, and includes a method of reducing oxygen from whole blood, or a component thereof, comprising placing the whole blood, or a component thereof in a device 20 comprising a sorbent 207 that has an absorption rate of at least 1.86 cubic centimeters per gram sorbent per hour ($cc \cdot g^{-1} \cdot hr^{-1}$), incubating the blood filled device 20 for up to four hours at ambient temperature while agitating at least once per second by translation of at least 3 cm; transferring the blood filled device 20 to storage at 4 to 6° C. In a further aspect, the blood filled device 20 is stored at 4 to 6° C. for up to 42 days.

BRIEF DESCRIPTION OF THE DRAWINGS

Some aspects of the disclosure are herein described, by way of example only, with reference to the accompanying drawings. With specific reference now to the drawings in detail, it is stressed that the particulars shown are by way of example and are for purposes of illustrative discussion of embodiments of the disclosure. In this regard, the description, taken with the drawings, makes apparent to those skilled in the art how aspects of the disclosure may be practiced.

Figures 1A, 1B:
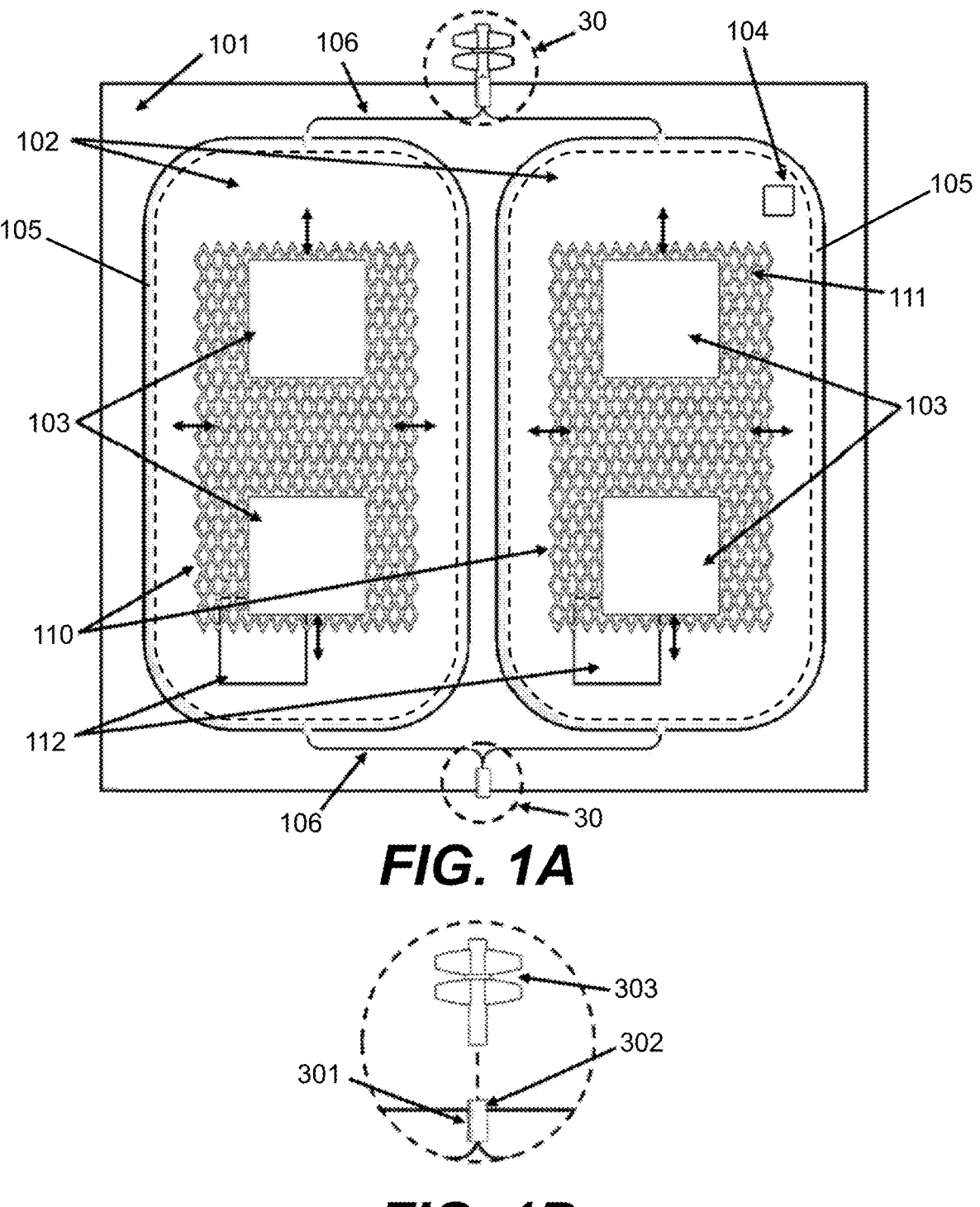
Figure 1C:
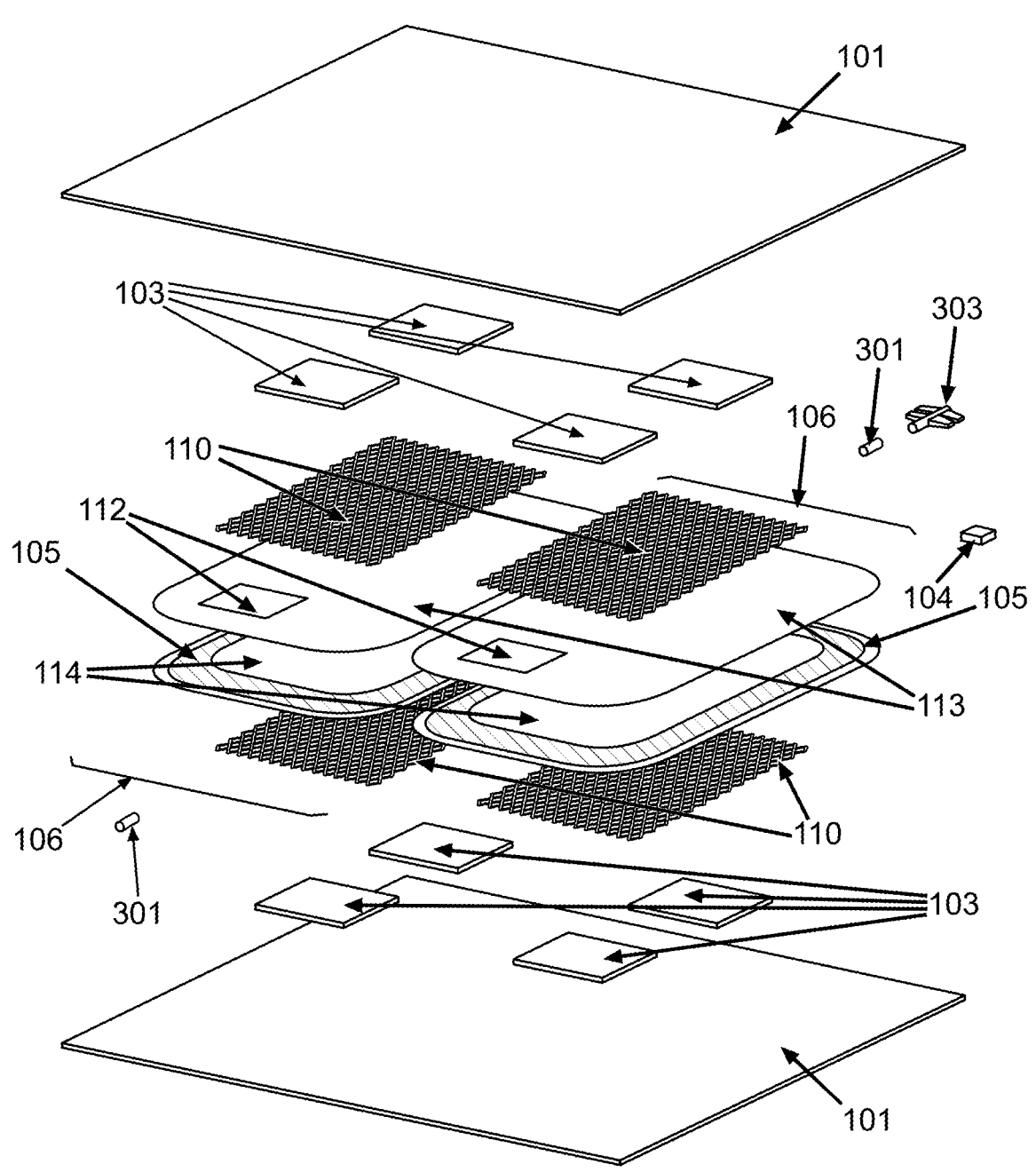

FIGS. 1A-C illustrate an exemplary embodiment of an oxygen depletion device according to the present disclosure having two compartments arranged side by side.

Figure 2A:
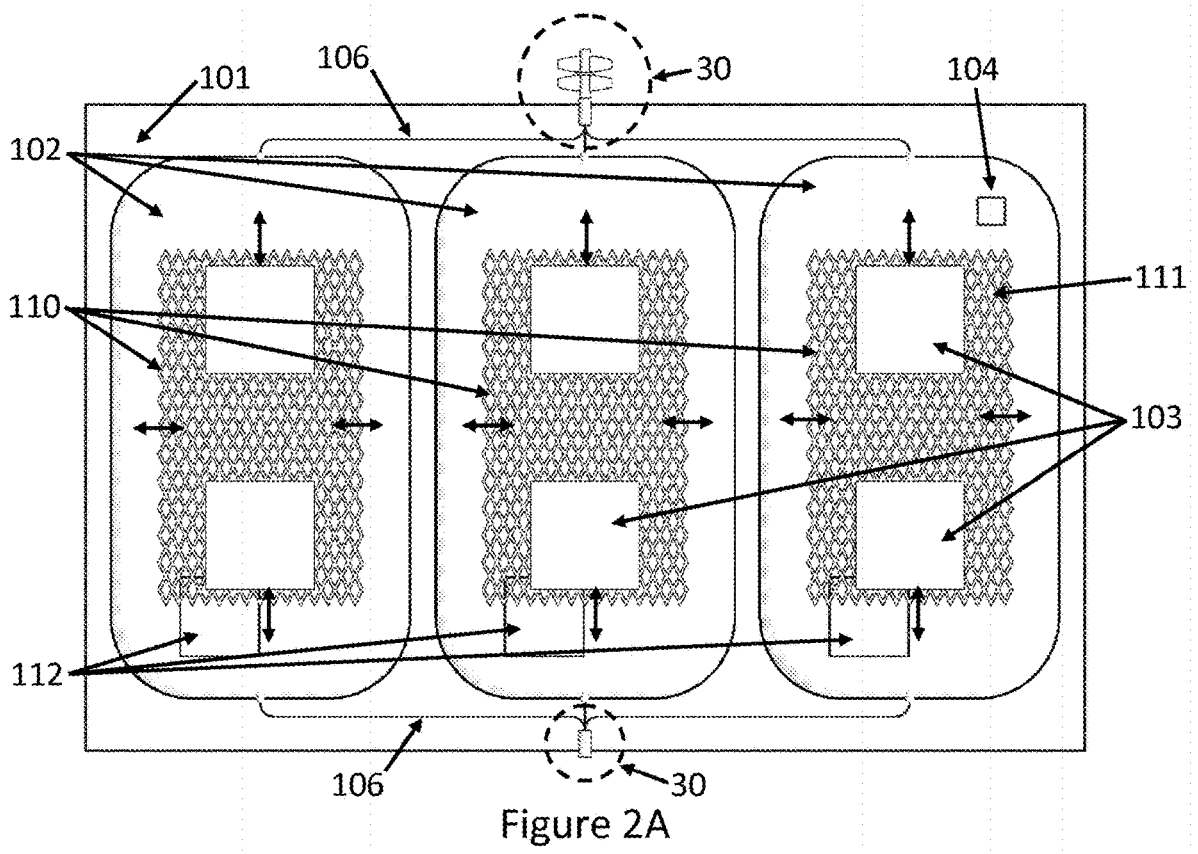
Figure 2B:
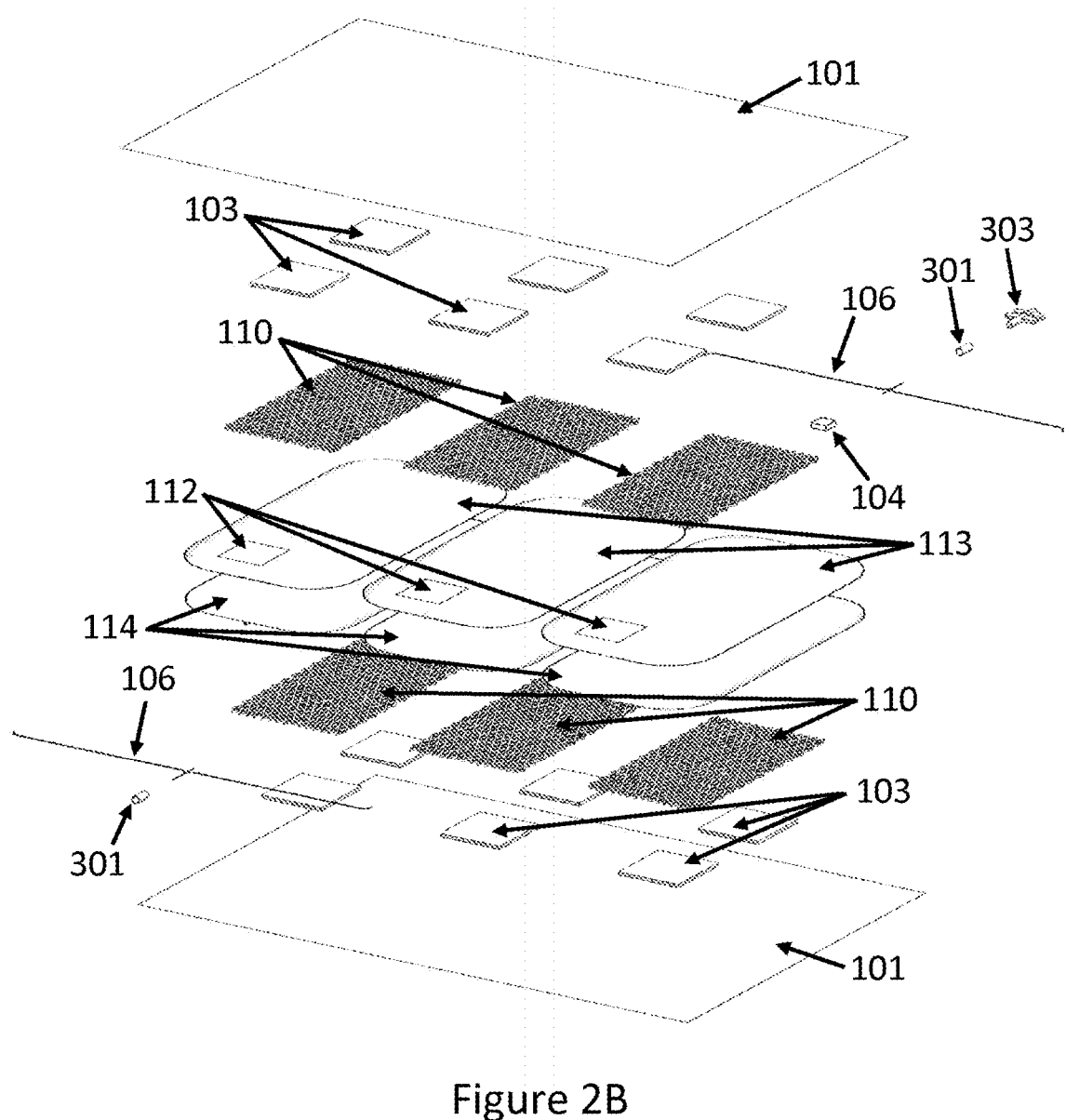

FIGS. 2A and 2B illustrate an exemplary embodiment of an oxygen depletion device according to the present disclosure having three compartments arranged side by side.

Figure 3A:
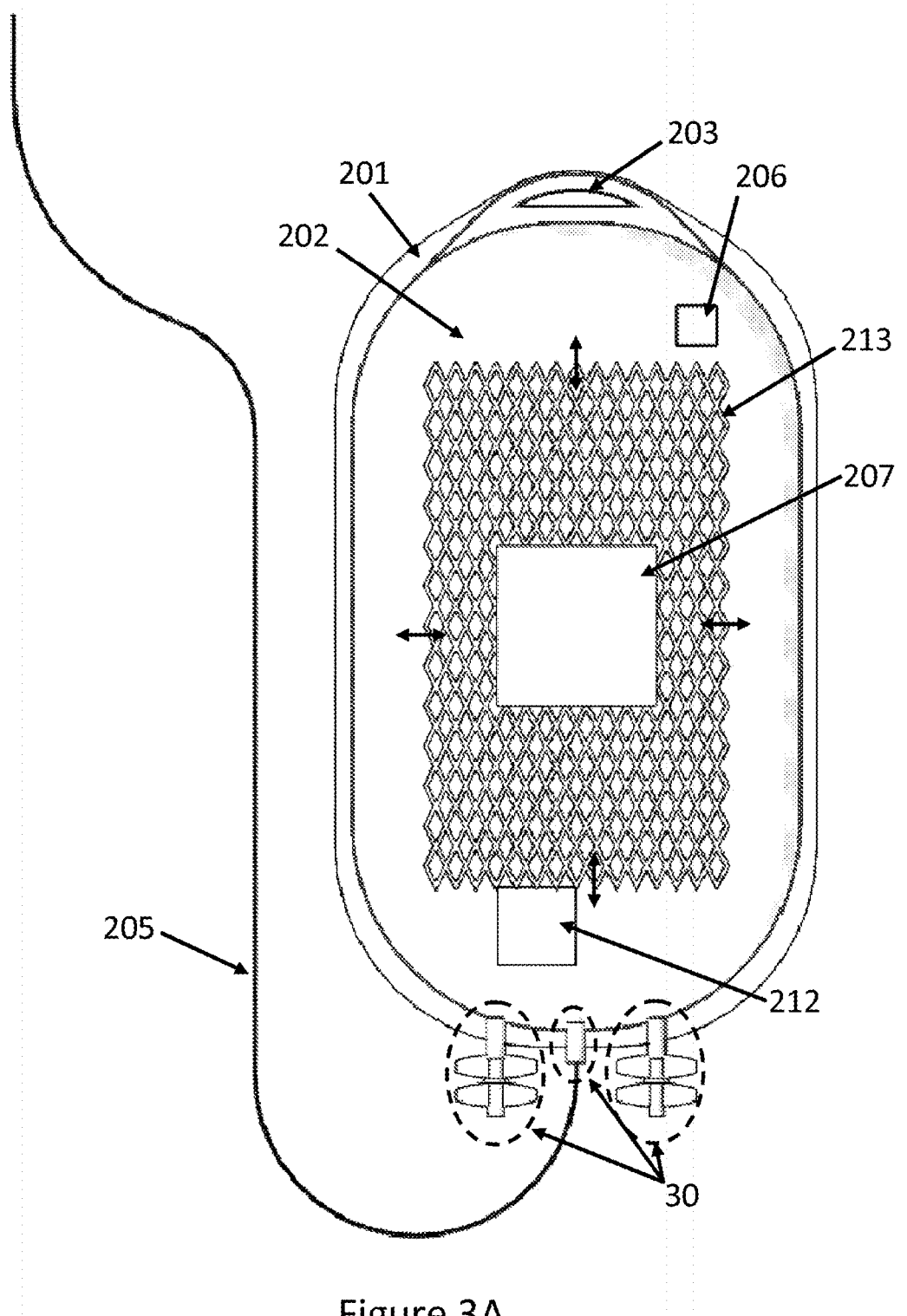
Figure 3B:
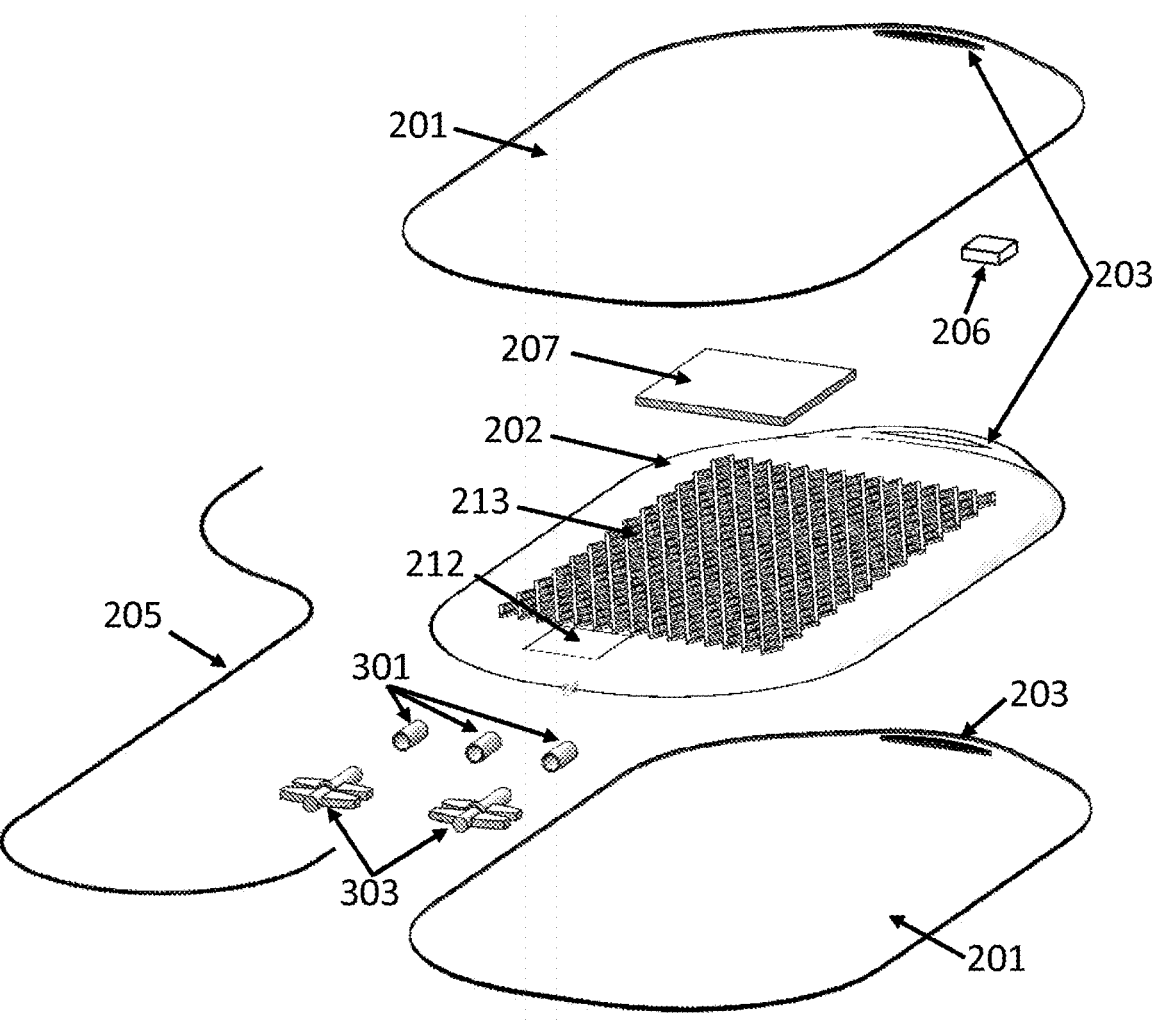

FIGS. 3A and 3B illustrate an exemplary embodiment of an anaerobic storage bag according to the present disclosure.

Figure 4A:
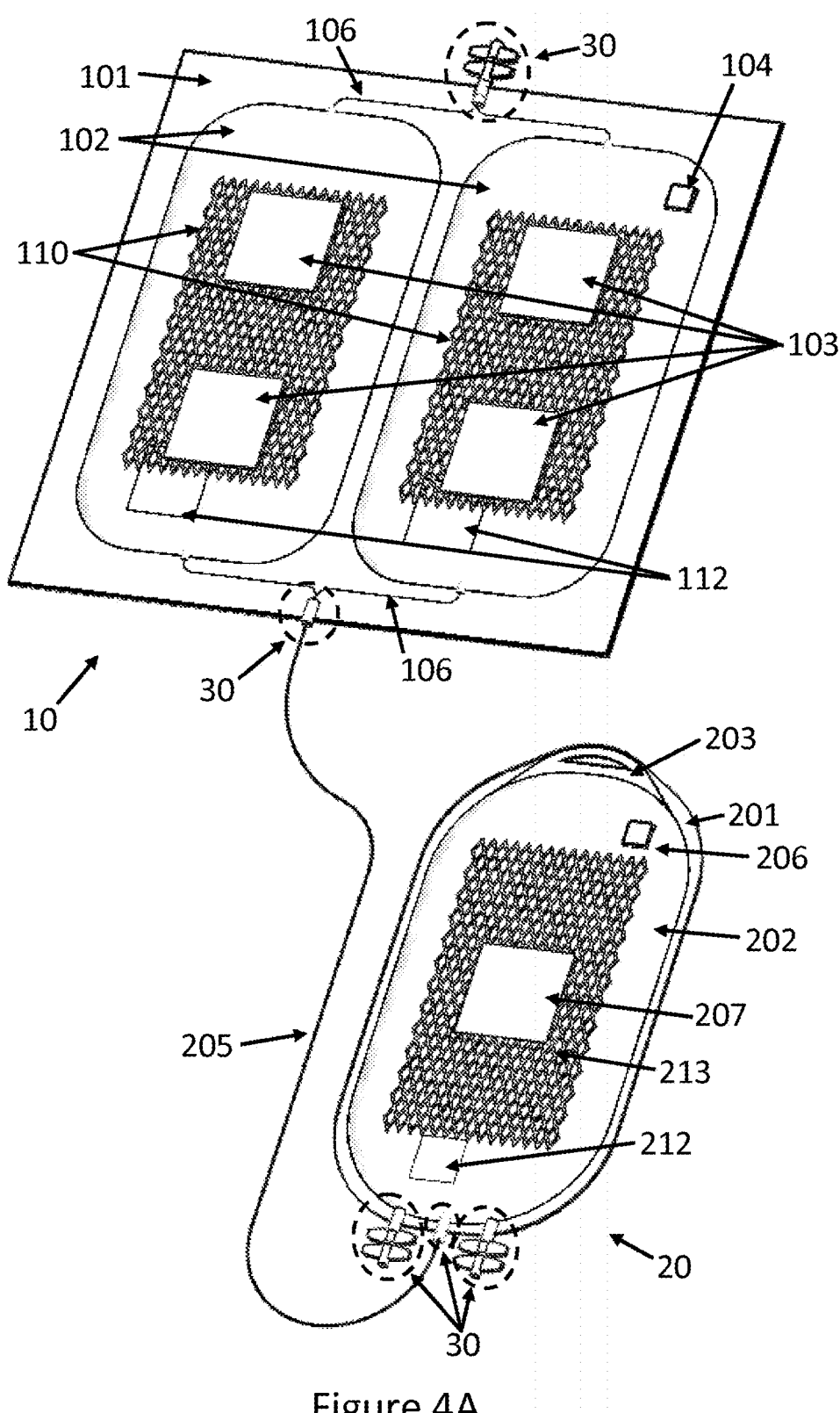
Figure 4B:
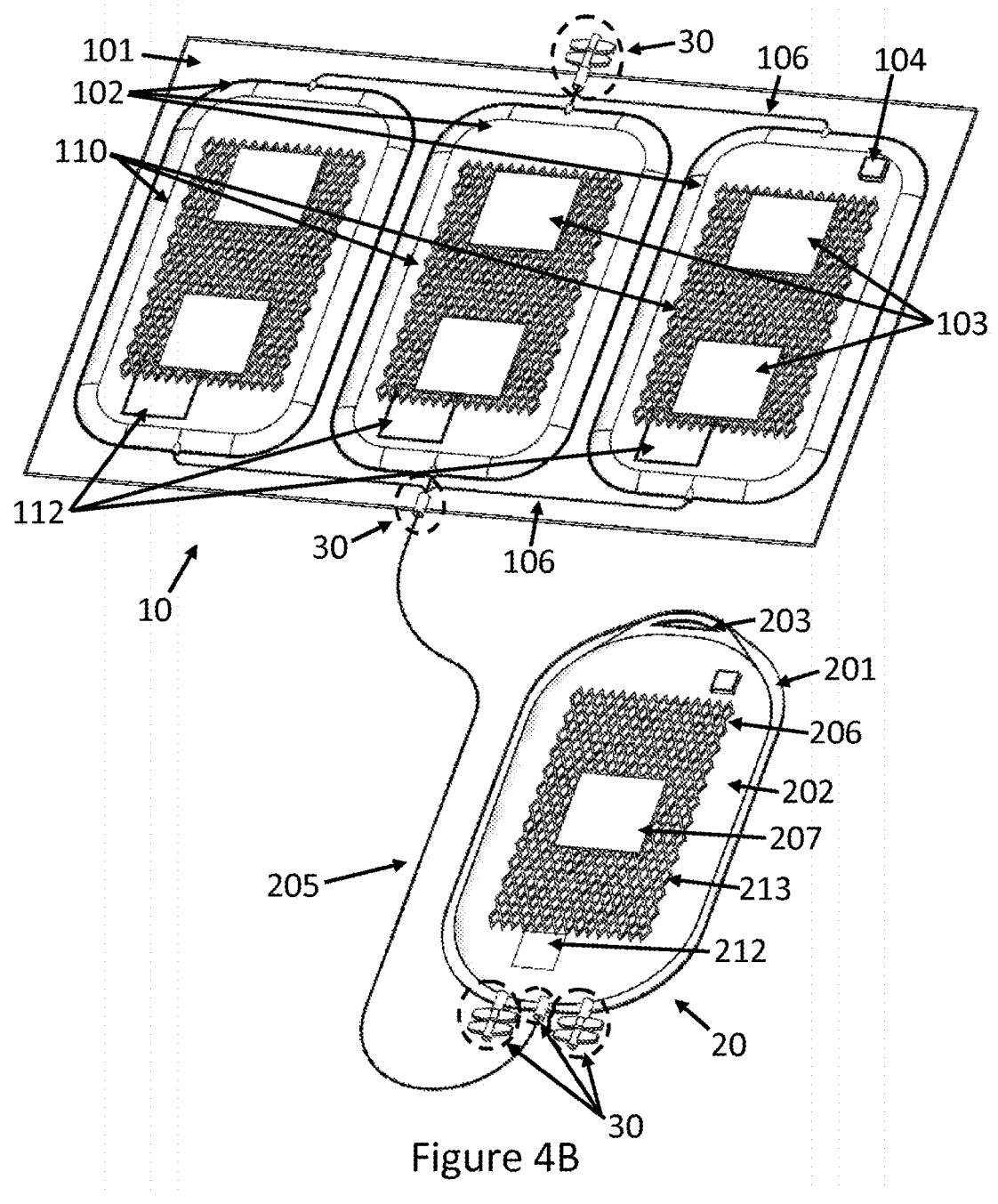

FIGS. 4A and 4B illustrate an exemplary embodiment of an oxygen reduction disposable storage system having a blood depletion device having two or three compartments, respectively, and an anaerobic storage bag according to the present disclosure.

Figure 5:
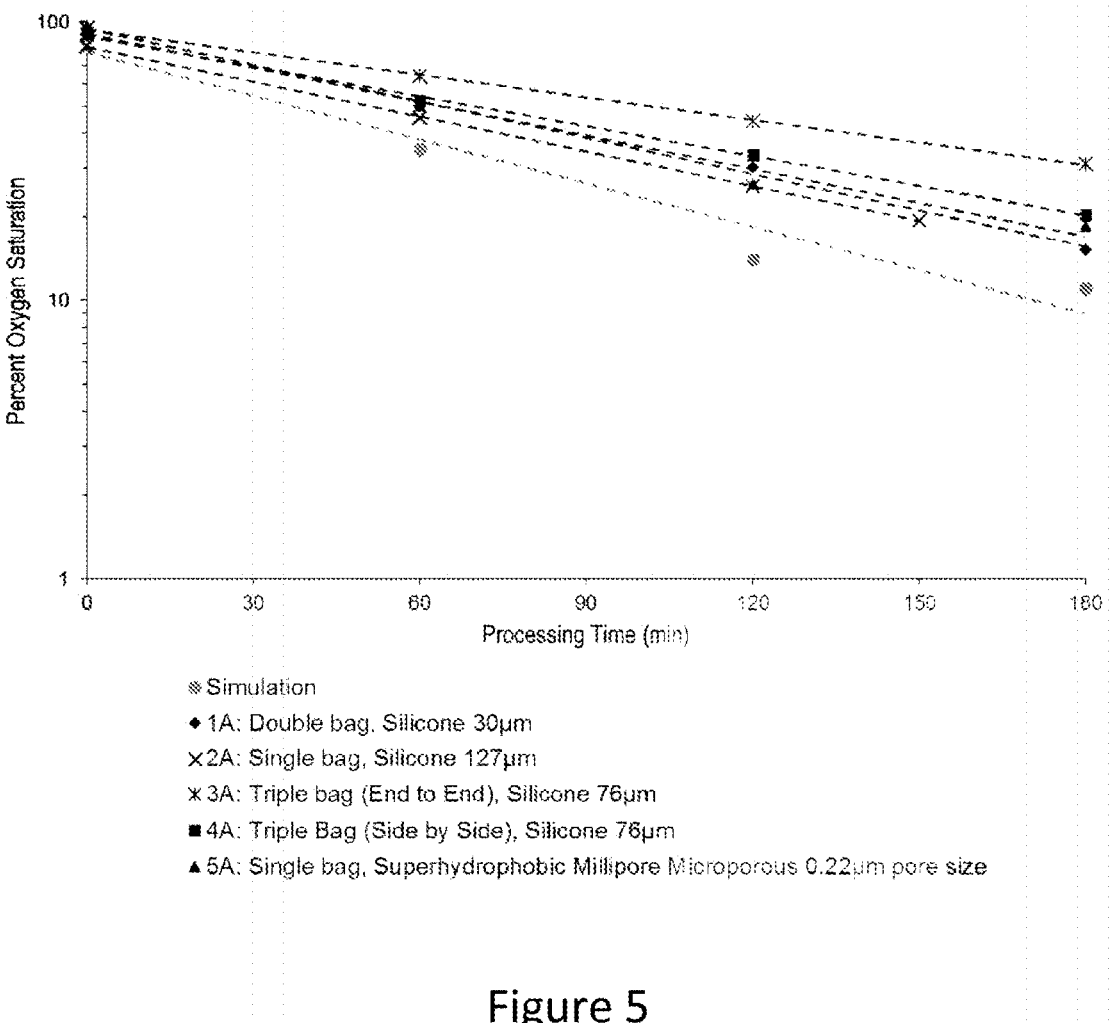

FIG. 5 is a graph of $sO_2$ reduction in exemplary oxygen depletion devices according to the methods of the present disclosure.

Figure 6A:
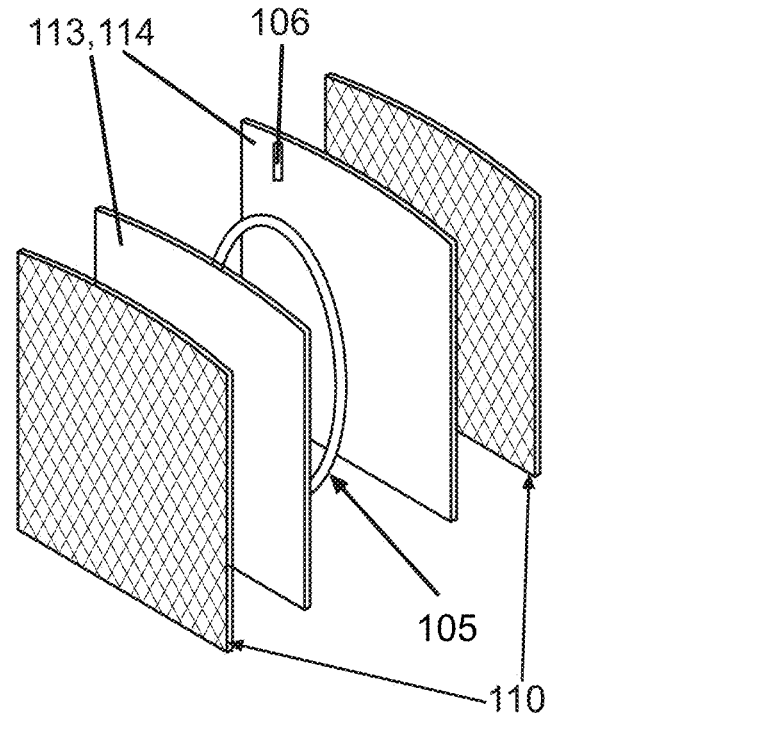
Figure 6A:
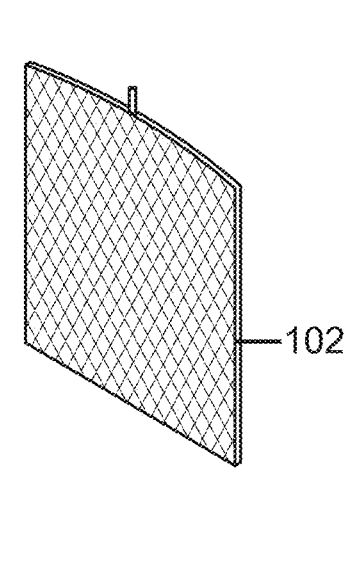
Figure 6B:
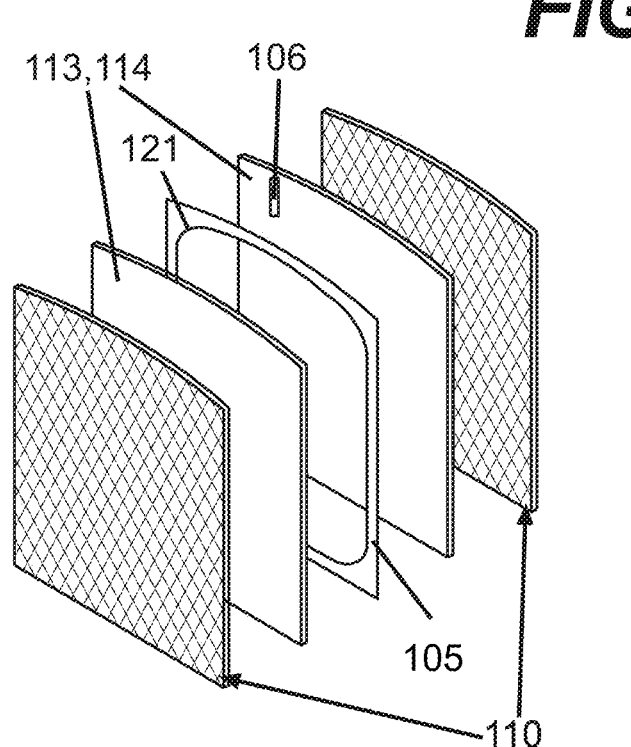
Figure 6B:
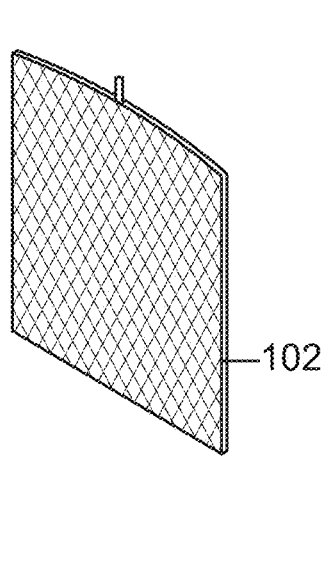

FIGS. 6A and 6B illustrates exemplary embodiments of an anaerobic storage bag according to the present disclosure.

Figure 7:
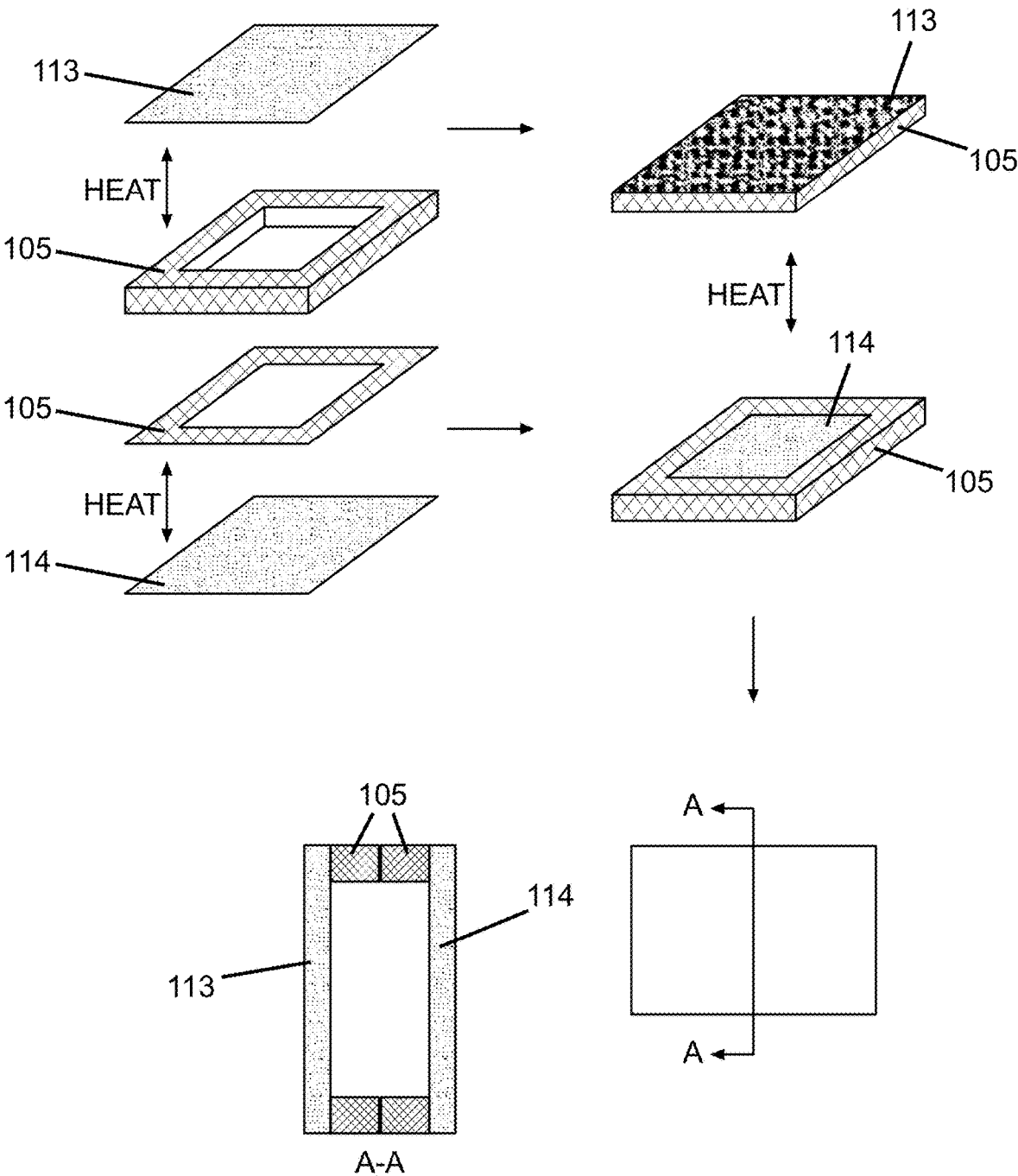

FIG. 7 illustrates an exemplary embodiment of tie layers 105 joining membranes 113 and 114 in a two-step process according to the present disclosure.

Figure 8A:
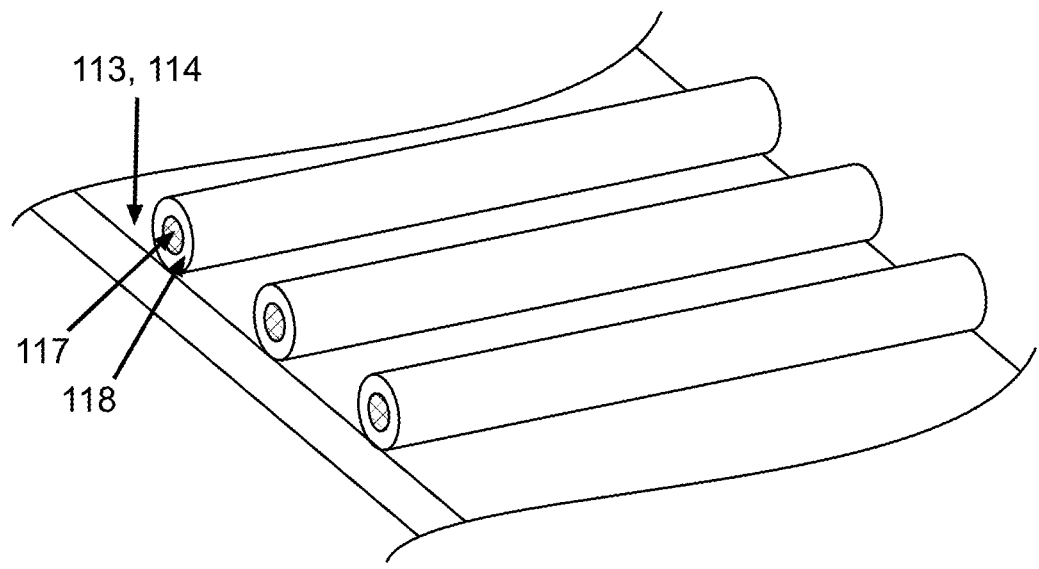
Figure 8B:
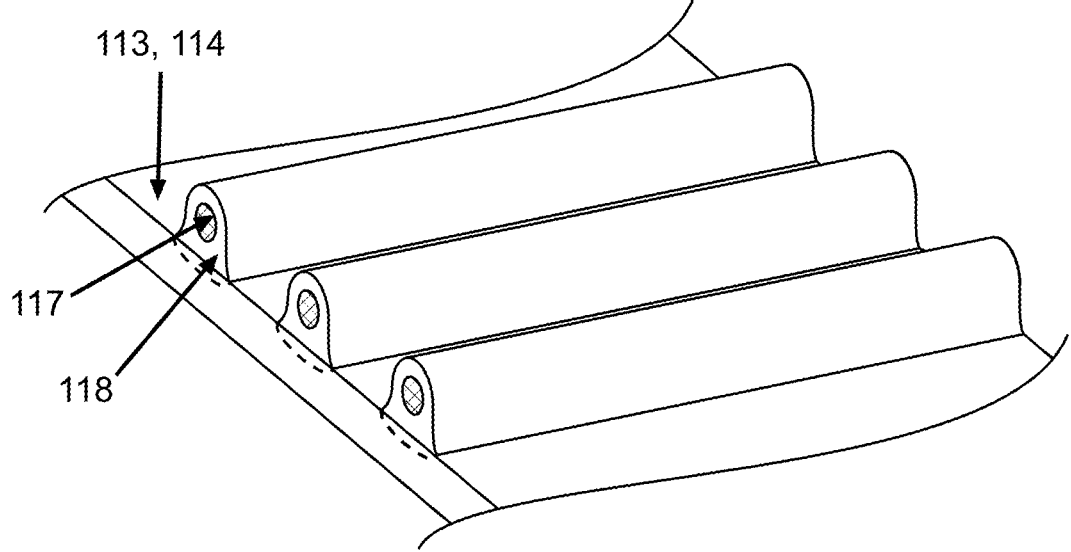

FIGS. 8A and 8B illustrate an exemplary embodiment of a spacer 110 comprising inner mesh 117 coextruded with binder mesh 118 and joined to a membrane 113 (114) according to the present disclosure.

Figure 9A:
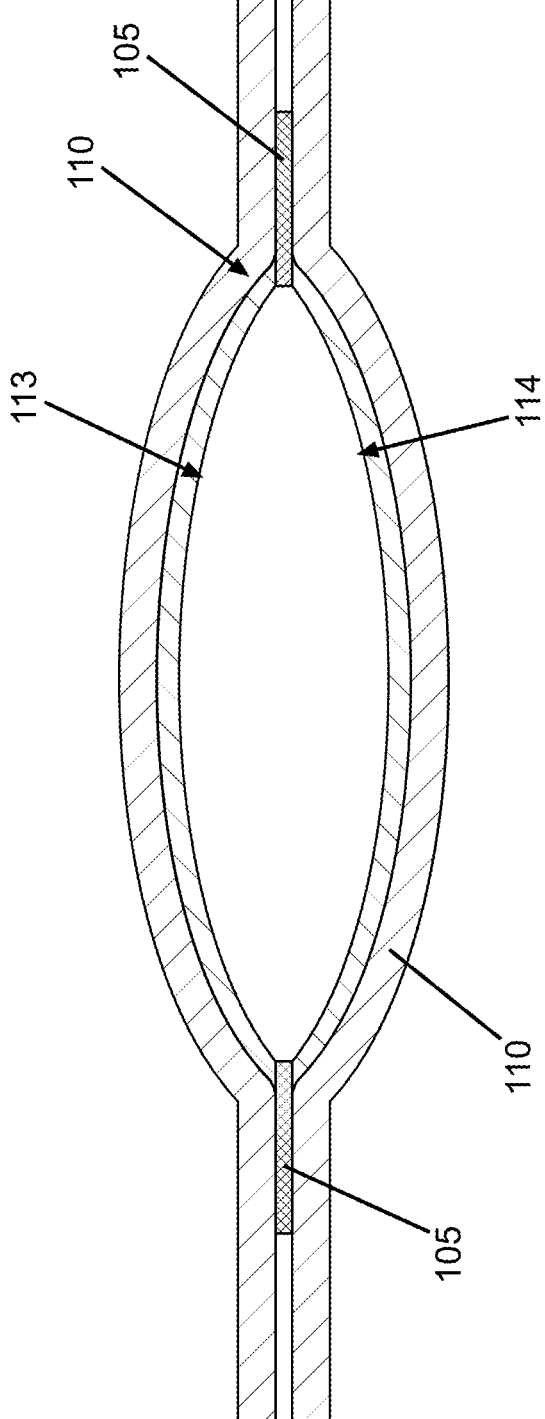
Figure 9B:
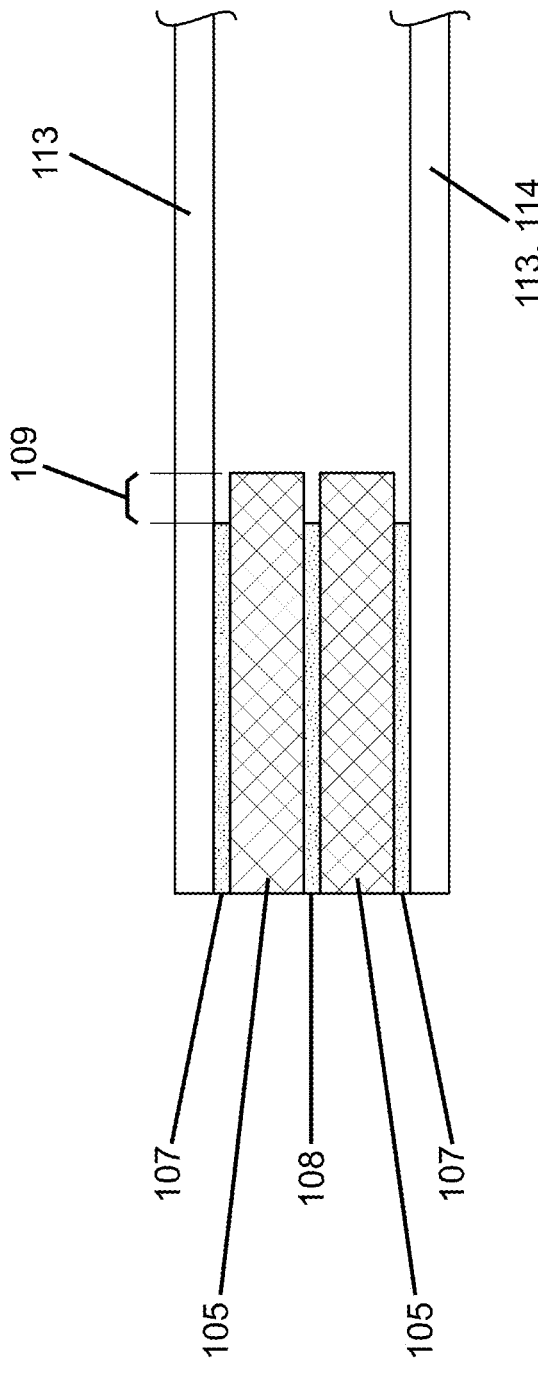

FIGS. 9A and 9B illustrate an exemplary embodiment of an anaerobic storage bag having a tie layer 105 joining membranes 113 and 114 (9A) and tie layers 105 applied to membranes 113 and 114 providing a seal 108 wherein the tie layers 105 extend beyond the seal 108 by a distance 109 (9B) according to the present disclosure.

FIGS. 10A to 10D illustrate exemplary embodiments of a tie layer 105 having geometric features 121 according to the present disclosure and further comprising a mixing structure 109 as shown in 10C and 10D.

Figure 11:
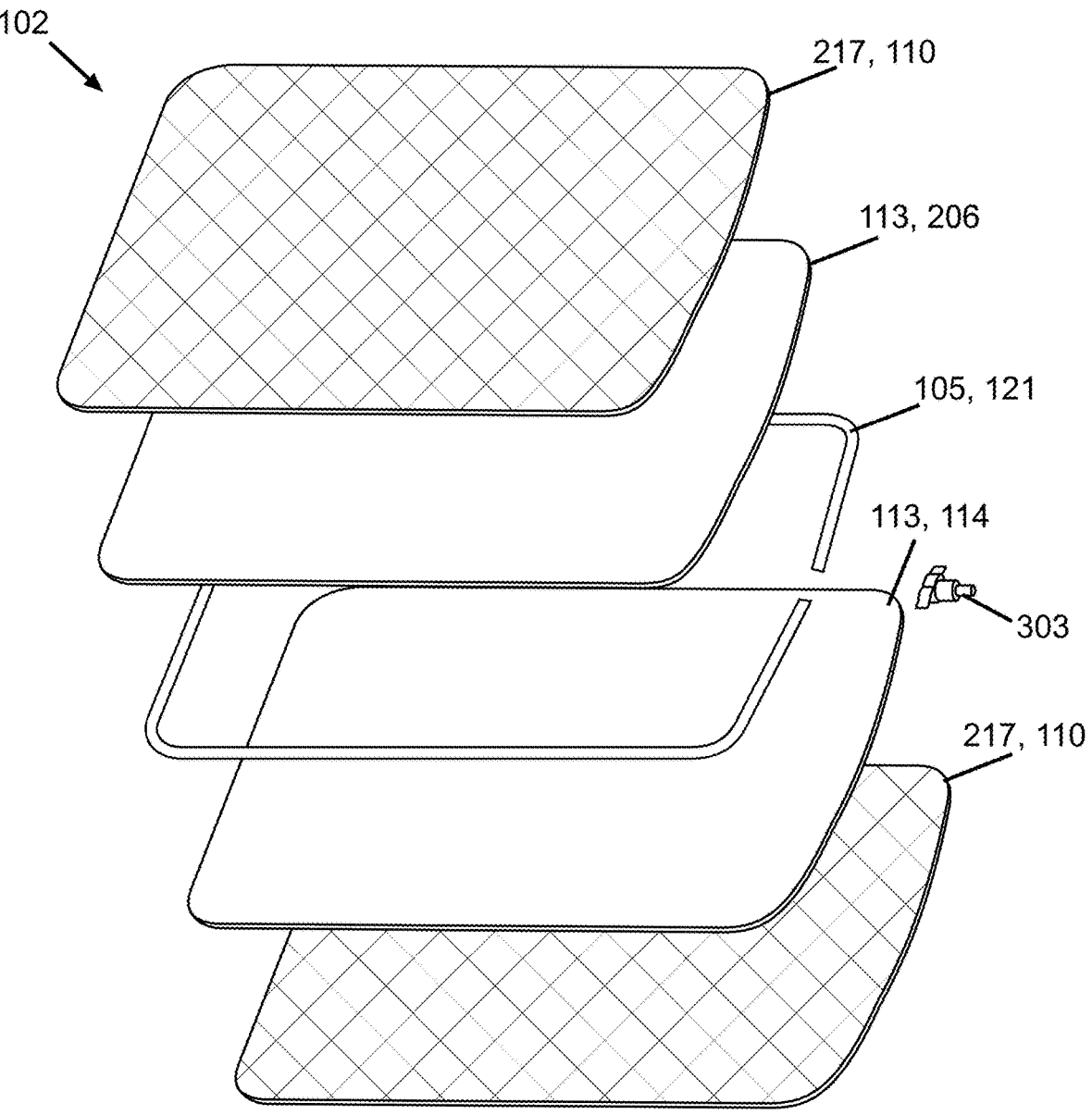

FIG. 11 illustrates an exemplary embodiment of a collapsible blood container having a spacer 110, a tie layer 105, and a geometric feature 121 according to the present disclosure.

Figure 12:
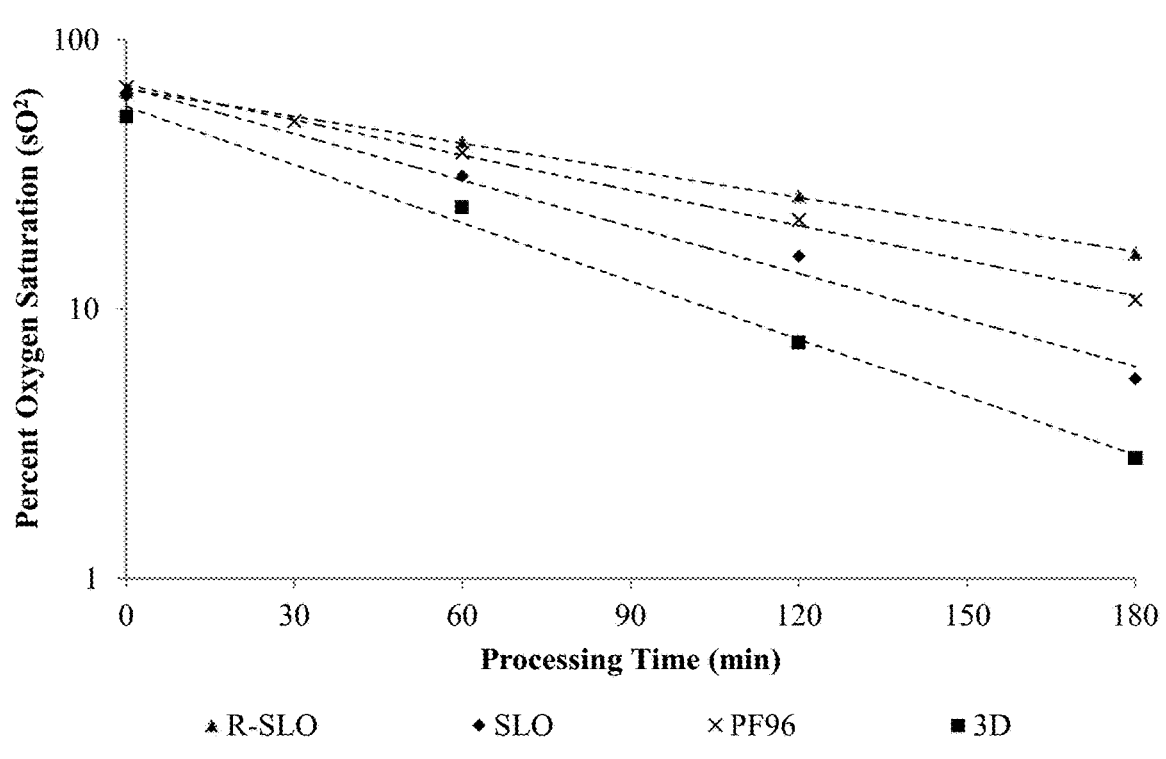

FIG. 12 is a graph of $sO_2$ reduction in an exemplary oxygen depletion device according to the methods of the present disclosure.

Figure 13:
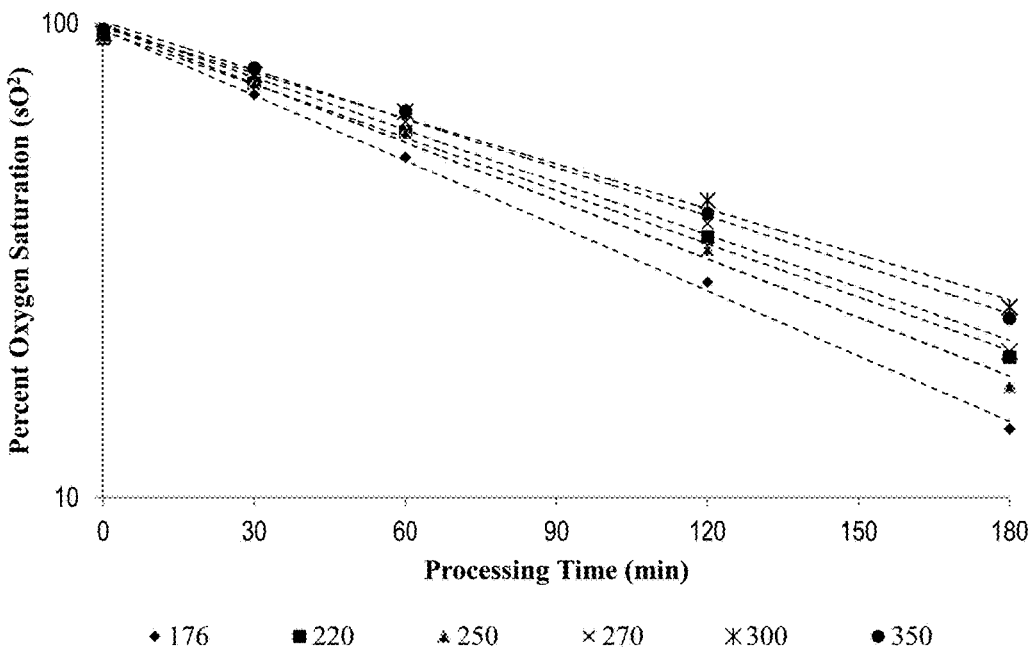

FIG. 13 is a graph of $sO_2$ reduction in an exemplary inner collapsible blood container 102 with various blood volumes, according to the methods of the present disclosure.

Figure 14:
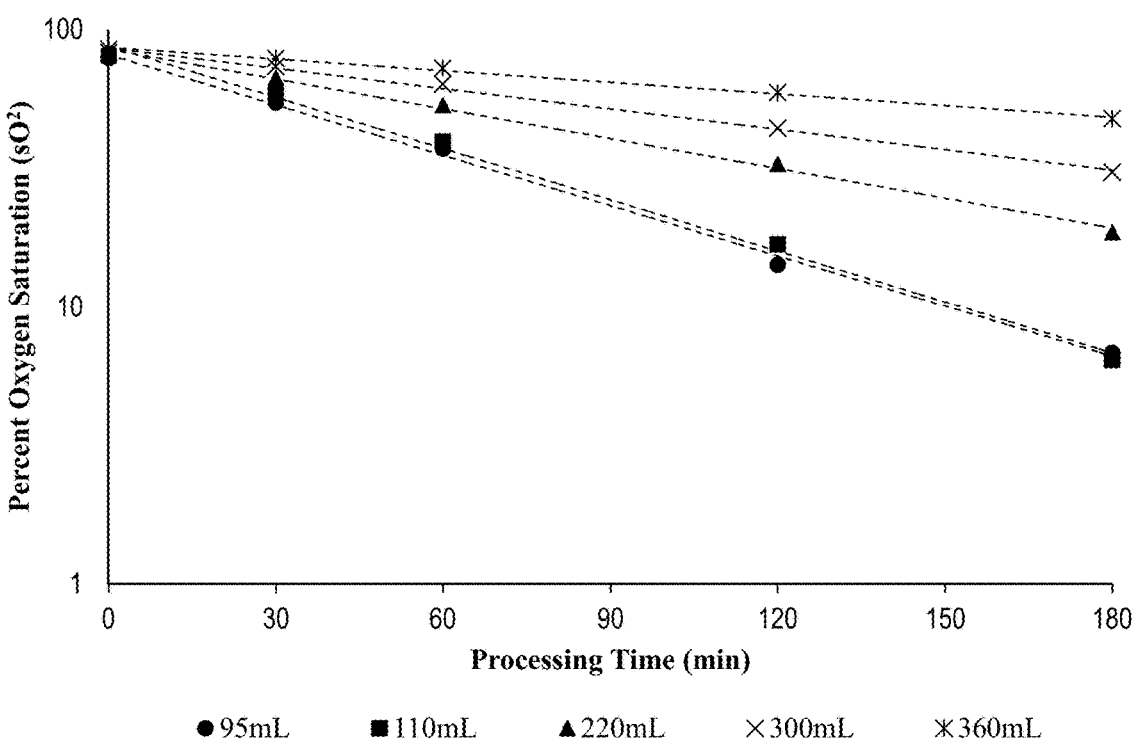

FIG. 14 is a graph of $sO_2$ reduction in an exemplary oxygen depletion device according to the methods of the present disclosure.

Figure 15:
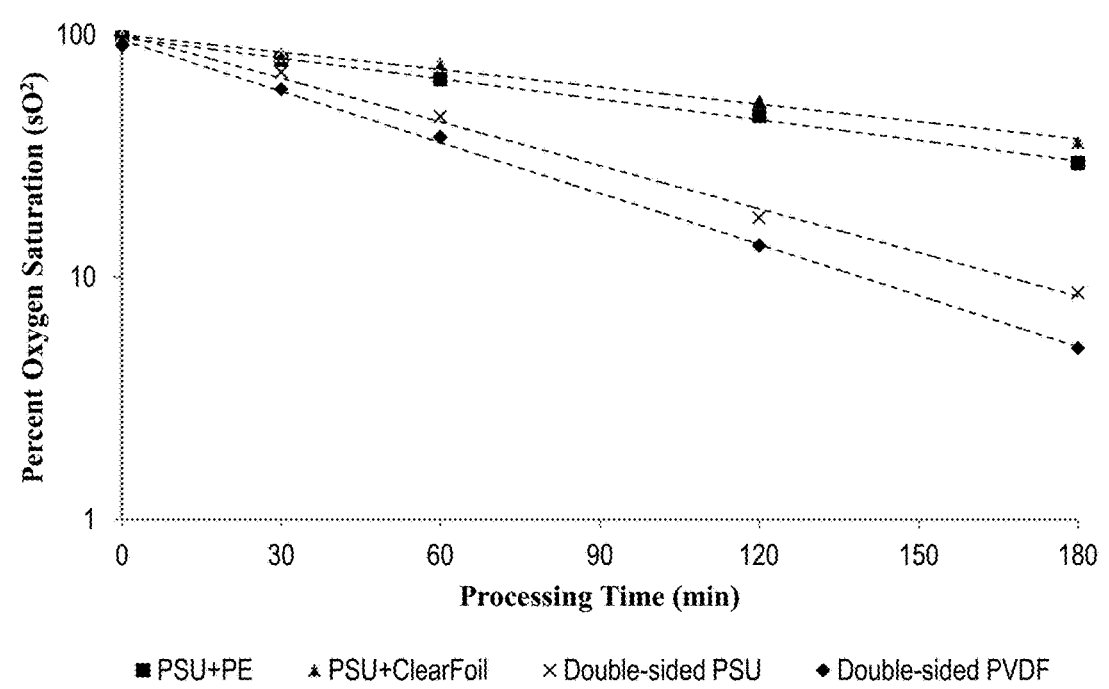

FIG. 15 is a graph of $sO_2$ reduction in an exemplary oxygen depletion device having different surface areas according to the methods of the present disclosure.

Figure 16:
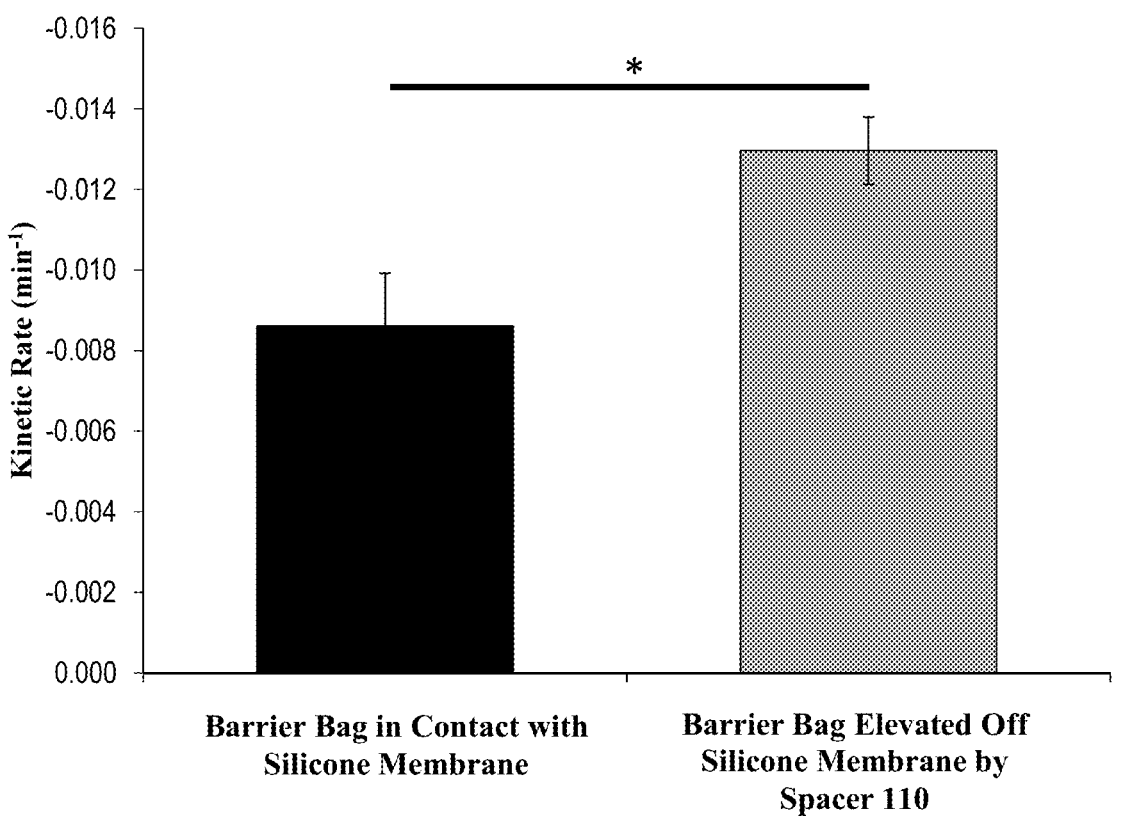

FIG. 16 is a graph showing the effect of spacer 110 on $sO_2$ reduction in an exemplary oxygen depletion device according to the present disclosure.

Corresponding reference characters indicate corresponding parts throughout the several views. The examples set out herein illustrate several embodiments of the invention but should not be construed as limiting the scope of the invention in any manner.

In light of current technology, there is a need to improve the quality of blood and blood components such as red blood cells that are to be stored and to extend the storage life of such blood and blood components in advance of transfusion to help minimize morbidity associated with transfusions. In order to conform with regulatory requirements and to ensure reliability, the preparation and processing of the red blood cells must be completed within a limited time period. Further, the process of preparing reduced oxygen blood and blood components must not introduce lesions, including but not limited to, hemolysis of the blood. Finally, there is a need for methods and devices that are compatible with existing anticoagulant and additive solutions to yield improved quality blood and blood components.

DETAILED DESCRIPTION

To address such needs and others, the present disclosure includes and provides devices and methodology for the preservation of blood and blood components in which the preparation of oxygen reduced blood and blood components is initiated at the donor collection stage.

Before explaining at least one aspect of the disclosure in detail, it is to be understood that the disclosure is not necessarily limited in its application to the details set forth in the following description or exemplified by the Examples. The disclosure is capable of other aspects or of being practiced or carried out in various ways.

As used herein, the term "bag" refers to collapsible containers prepared from a flexible material and includes pouches, tubes, and gusset bags. As used herein, and included in the present disclosure, the term includes folded bags having one, two, three, or more folds and which are sealed or bonded on one, two, three, or more sides. Bags may be prepared using a variety of techniques known in the art including bonding of sheets of one or more materials. Methods of bonding materials to form bags are known in the art. Also included and provided for in the present disclosure are containers prepared by injection and blow molding. Methods to prepare blow molded and injection molded containers are known in the art. Preferred types of blow molded or injection molded containers are flexible containers that can be reduced in size for efficient packing and shipping while being capable of expanding to accommodate blood or blood components for reduction of oxygen. They also may be designed to conform to the volume of the blood until they are fully expanded. As used throughout the present disclosure, the bags are a form of collapsible container and the two terms are used interchangeably throughout the present disclosure.

As used herein, the term "collapsible container" includes bags, containers, enclosures, envelopes, pouches, pockets, receptacles, and other devices that can contain and retain a liquid or fluid. In certain aspects, the collapsible container may be manufactured by conventional means such as injection molding or insert molding. In other aspects, the collapsible container may be prepared from sheets of polymer materials that are bonded together using methods known in the art to prepare containers capable of holding a volume. Such collapsible containers are well known in the art. See, for example, U.S. Pat. No. 3,942,529 issued to Waage; U.S. Pat. No. 4,131,200 issued to Rinfret; and U.S. Pat. No. 5,382,526 issued to Gajewski et al. Suitable methods for bonding polymer materials to prepare collapsible containers according to the present disclosure include heat welding, ultrasonic welding, radio frequency (RF) welding, and solvent welding. In certain aspects, multiple bonding methods may be used to prepare collapsible containers according to the present disclosure. Collapsible containers according to the present disclosure include enclosures having one or more pleats, folds, diaphragms, bubbles, and gussets. Methods for preparing collapsible containers are known in the art. See, for example, U.S. Pat. No. 3,361,041 issued to Grob; U.S. Pat. No. 4,731,978 issued to Martensson; U.S. Pat. No. 4,998,990 issued to Richter et al.; and U.S. Pat. No. 4,262,581 issued to Ferrell. Also included and provided for in the present disclosure are containers having combinations of both flexible and inflexible parts, wherein the flexible parts allow for the expansion of the volume through, for example, pleats, folds or gussets and other similar geometric features in the packaging shape, whereas the inflexible parts may provide rigidity and geometry definition to the container. Methods and designs for preparing collapsible containers having both flexible and inflexible parts are known in the art, such as described by Randall in U.S. Pat. No. 6,164,821 and by LaFleur in U.S. Pat. No. 5,328,268.

As used herein the term "about" refers to +10%.

The terms "comprises," "comprising," "includes," "including," "having," and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques, and procedures for accomplishing a given task including, but not limited to, those manners, means, techniques, and procedures either known to or readily developed from known manners, means, techniques, and procedures by practitioners of the chemical, pharmacological, biological, biochemical, and medical arts.

The present disclosure provides for, and includes, an oxygen depletion device 10 for depleting oxygen from blood comprising an outer receptacle 101 substantially impermeable to oxygen, inner collapsible blood container 102 that is permeable to oxygen, and an oxygen sorbent 103 situated within outer receptacle 101.

The present disclosure also provides for, and includes, oxygen depletion devices 10 configured to be a blood collection and oxygen depletion device 10. Oxygen depletion devices configured to collect and reduce blood oxygen differ from the oxygen depletion device 10 as described throughout this specification in that a blood collection and oxygen depletion device 10 further includes an anticoagulant to prevent coagulation of the whole blood during the collection process. In certain aspects, the anticoagulant solution of a blood collection and oxygen depletion device 10 is provided in the blood collection and oxygen depletion device 10. Accordingly, included anticoagulant solutions are also oxygen depleted anticoagulant solutions. In the alternative, anticoagulant solutions may be included separately, either as oxygen depleted solutions or solutions having oxygen. A blood collection and oxygen depletion device 10 is intended to be used with whole blood collected from a donor. As used throughout the present disclosure, the oxygen and depletion device 10 includes and provides for blood collection and oxygen depletion device 10. The two terms can be, and are, used interchangeably.

As used herein, the outer receptacles are prepared from materials that are substantially impermeable to oxygen and optionally impermeable to carbon dioxide. In certain aspects, an outer receptacle 101 is prepared from flexible film materials. In other aspects, an outer receptacle 101 is prepared from a stiff, or inflexible film material.

The present disclosure provides for, and includes, an outer receptacle 101 substantially impermeable to oxygen. As used herein, an outer receptacle 101 that is substantially impermeable to oxygen is sufficiently impermeable to oxygen to allow no more than 10 cc of oxygen inside the receptacle over a period of 3 months, and more preferably no more than 5 cc of oxygen over 6 months. As used herein, the term substantially impermeable to oxygen (SIO) refers to materials and compositions that provide a barrier to the passage of oxygen from one side of the barrier to the other, sufficient to prevent significant increases in the partial pressure of oxygen.

It is notable that few materials provide complete impermeability and that even the high impermeability of materials can be compromised when joining, welding, folding, and otherwise assembling an outer receptacle 101. As will be discussed below, oxygen depletion device 10 may further incorporate one or more inlets/outlets 30 comprising a tube 301 and a bond 302 to the outer receptacle 101 (or outer receptacle 201 described below). The outer receptacle 101 must also be designed to accommodate changes in volume of the inner collapsible blood container 102. Accordingly, special care is taken to incorporate specific design elements and manufacturing methods to ensure the integrity of the impermeable barrier.

The present disclosure also provides for, and includes, an outer receptacle 101 that is substantially impermeable to oxygen having a permeability to oxygen of less than about 1.0 cc of oxygen per square meter per day. In certain aspects, a film suitable for use in the preparation of an outer receptacle and other elements of the present disclosure are materials characterized by a Barrer value of less than about 0.140 Barrer.

Materials and methods to prepare an outer receptacle 101 are known in the art. See, for example, U.S. Pat. No. 7,041,800 issued to Gawryl et al., U.S. Pat. No. 6,007,529 issued to Gustafsson et al., and U.S. Patent Application Publication No. 2013/0327677 by McDorman, each of which are hereby incorporated by reference in their entireties. Impermeable materials are routinely used in the art and any suitable material can be used. In the case of molded polymers, additives are routinely added to enhance the oxygen (and $CO_2$) barrier properties. See, for example, U.S. Pat. No. 4,837,047 issued to Sato et al. For example, U.S. Pat. No. 7,431,995 issued to Smith et al. describes an oxygen- and carbon dioxide-impermeable receptacle composed of layers of ethylene vinyl alcohol copolymer and modified ethylene vinyl acetate copolymer, impermeable to oxygen and carbon dioxide ingress. In another aspect, the outer receptacle 101 is impermeable to oxygen and carbon dioxide.

In certain aspects, films that are substantially impermeable to oxygen may be laminated films. In an aspect, a laminated film that is substantially impermeable to oxygen is a laminated foil film. Film materials can be polymers or foil materials or multilayer constructions that are combinations of foils and polymers. In an aspect, a laminated film may be a polyester membrane laminated with aluminum. An example of suitable aluminum laminated film, also known as a laminated foil, that is substantially impermeable to oxygen is known in the art. For example, U.S. Pat. No. 4,798,728 to Sugisawa discloses aluminum laminated foils of nylon, polyethylene, polyester, polypropylene, and vinylidene chloride. Other laminated films are known in the art. For example, U.S. Pat. No. 7,713,614 to Chow et al. discloses multilayer containers comprising an ethylene-vinyl alcohol copolymer (EVOH) resin that is substantially impermeable to oxygen. In an aspect, an outer receptacle 101 may be a barrier bag constructed by sealing three or four sides by means of heat sealing. The bag is constructed of a multilayer construction that includes materials that provide enhancement to $O_2$ and $CO_2$ barrier properties. The bag is constructed of a multilayer construction that includes materials that provide enhancement to $O_2$ and $CO_2$ barrier properties. Such materials include the Rollprint Clearfoil® V2 film, having an oxygen transmission rate of 0.01 cc/100 in$^2$/24 hrs., Rollprint Clearfoil® X film, having an oxygen transmission rate of 0.004 cc/100 in$^2$/24 hrs. and Clearfoil® Z film having an oxygen transmission rate of 0.0008 cc/100 in$^2$/24 hrs. (Rollprint Packaging Products, Addison, IL). Other manufacturers make similar products with similar oxygen transmission rates, such as Renolit Solmed Wrapflex® films (American Renolit Corp., City of Commerce, CA). An example of suitable aluminum laminated film, also known as a laminated foil, that is substantially impermeable to oxygen is obtainable from Protective Packaging Corp. (Carrollton, TX).

Another approach applicable to the preparation of SIO materials includes multilayer graphitic films made by gentle chemical reduction of graphene oxide laminates with hydroiodic and ascorbic acids. See Su et al., "Impermeable barrier films and protective coatings based on reduced graphene oxide," Nature Communications 5, Article number: 4843 (2014), hereby incorporated by reference in its entirety. Nanoparticles to enhance oxygen barrier properties are also known in the art, for example, the multilayer barrier stack films provided by Tera-Barrier (Tera-Barrier Films Pte, Ltd, The Aries, Singapore) and described by Rick Lingle in Packaging Digest Magazine on Aug. 12, 2014.

In aspects according to the present disclosure, an outer receptacle 101 may be prepared from a gas impermeable plastic. In an embodiment, the gas impermeable plastic may be a laminate. In certain embodiments, the laminate may be a transparent barrier film, for example, a nylon polymer. In embodiment, the laminate may be a polyester film. In an embodiment, the laminate may be Mylar®. In certain embodiments, the laminate may be a metalized film. In an embodiment, the metalized film may be coated with aluminum. In another embodiment, the coating may be aluminum oxide. In another embodiment, the coating may be an ethylene vinyl alcohol copolymer (EVOH) laminated between layers of low density polyethylene (LDPE).

An outer receptacle 101 of the present disclosure may be formed of one or more parts prepared from a gas impermeable material including a plastic or other durable lightweight material. In some embodiments, an enclosure may be formed of more than one material. In an embodiment, an outer receptacle 101 may be formed of a material and coated with a gas impermeable material to prepare a gas impermeable enclosure. In an embodiment, a rigid or flexible outer receptacle 101 may be prepared from a plastic that may be injection molded. In embodiments according to the instant disclosure, the plastic may be selected from polystyrene, polyvinyl chloride, or nylon. In an embodiment, outer receptacle 101 materials may be selected from the group consisting of polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA) (e.g., nylon), acrylonitrile butadiene styrene (ABS), polycarbonate (PC), polycarbonate/acrylonitrile butadiene styrene (PC/ABS), polyurethanes (PU), melamine formaldehyde (MF), plastarch material, phenolics (PF), polyetheretherketone (PEEK), polyetherimide (PEI) (Ultem), polylactic acid (PLA), polymethyl methacrylate (PMMA), polytetrafluoroethylene (PTFE), urea-formaldehyde, and ethylene vinyl alcohol copolymer (EVOH). In certain embodiments, the outer receptacle 101 may be polyethylene. In some embodiments, the polyethylene outer receptacle 101 may comprise one or more polyethylene components that are welded together. In certain aspects, the outer receptacle is comprised of a multilayer film having a polyethylene outer layer, a polyester inner layer, and an aluminum oxide barrier layer dispersed between the inner and outer layers, for example, the Clearfoil® Z film having an oxygen transmission rate of 0.0008 cc/100 in$^2$/24 hrs. (Rollprint Packaging Products, Addison, IL).

The present disclosure provides for, and includes, the preparation of outer receptacles 101 from a film and inner collapsible blood container 102 from a membrane. As used herein, membranes generally refer to materials used to prepare an inner collapsible blood container 102 and films are used to refer to materials used to prepare outer receptacle 101. While it is understood that certain materials may be referred by the manufacturer as a "membrane" or may be generally known as a "membrane", for clarity, unless otherwise indicated a film is considered substantially impermeable. A membrane comprises one or more layers of materials in the form of a sheet that allows one or more substances to pass through from one side of the sheet to the other side of the sheet. As used herein, membranes may also be prepared as tubes suitable for connecting together components of oxygen depletion devices 10, blood collection kits, or connecting together elements of blood collection devices, additive solution bags, leukocyte reduction filters, and anaerobic storage bags. As used throughout, it is understood that a membrane of the present disclosure may be formed as a sheet or a tube depending on the application. Also as previously provided, films to prepare outer receptacles 101 are substantially impermeable to oxygen while an inner collapsible blood container 102 is permeable to oxygen. As used herein, films may also be prepared as tubes suitable for connecting together components of oxygen depletion devices 10, blood collection kits, or connecting together elements of blood collection devices, additive solution bags, leukocyte reduction filters, and anaerobic storage bags. As used herein the outer receptacles 101 contain all embodiments of 102 as further described.

As used herein, an inner collapsible blood container 102 is permeable to oxygen. In certain aspects, an inner collapsible blood container 102 is permeable to oxygen and carbon dioxide. In other aspects, an inner collapsible blood container 102 is impermeable to oxygen and permeable to carbon dioxide.

The present disclosure provides for and includes the preparation of outer receptacles 101 using heat sealing, blow molding, and injection molding techniques. Suitable materials for preparing outer receptacles 101 using heat sealing, blow molding, and injection molding include PET, standard and multilayer, polypropylene, polyethylene, polycarbonate, ABS, and other polymers known to those skilled in the art. Methods to prepare blow molded and injection molded outer receptacles 101 are known in the art, for example, a multilayer structure comprised of a barrier layer of ethylvinyl alcohol (EVOH) or ethylvinylacetate (EVA) situated between two layers of polypropylene (PP) and offered by Kortec (Kortec, Inc., Rowley, MA) and also as described in U.S. Pat. No. 5,906,285 issued to Slat. Additives that strengthen the oxygen and $CO_2$ barrier properties of the polymers prior to molding or during their formulation or during setup are known in the art. One example is multilayer polymer co-injection resulting in a multilayer PET. Such a barrier resin is typically incorporated at the preform stage as an inner layer with PET on both sides, making PET the liquid contact layer as well as the outside layer. As provided below, suitable blow molded or injection molded outer receptacles 101 are impermeable to oxygen. In certain aspects, suitable heat sealed, blow molded, or injection molded outer receptacles 101 are substantially impermeable to both oxygen and carbon dioxide.

The present disclosure provides for, and includes, two types of materials for the preparation of either permeable membranes or substantially impermeable films. In an aspect, permeable membranes according to the present disclosure provide for the passage of substances through the material, specifically but not necessarily exclusively, oxygen. In certain aspects, membranes are selected to permit the passage of oxygen and carbon dioxide while preventing the passage of water, proteins, salts (e.g., plasma components) and cells (e.g., red blood cells, white blood cells, and platelets). The rate of passage through a material depends on one or more properties including particle size, phase of material (liquid vs. gas), hydrophilicity, hydrophobicity, or solubility. The rate of passage, or flux, through a material also depends on the presence or absence of a driving force such as a difference in pressure (or partial pressure), differences in temperature, or differences in concentration between one side of the membrane and the other. The flux through a membrane is known as the membrane permeation flux. The membrane permeation flux of substances through a membrane is inversely proportional to the thickness of the membrane.

Membrane permeation flux, for a gas, is defined as the volume flowing through the membrane per unit area per unit time. The SI unit used is $m^3/m^2 \cdot s$. For gases and vapors, the volume is strongly dependent on pressure and temperature. Accordingly, permeation fluxes for gases are often given in terms of standard temperature and pressure (STP) which is defined as 0° C. and 1 atmosphere (1.0013 bar) (e.g., 273° K and 760 torr). As noted above, the rate of passage depends on a driving force or difference between the two sides of the membrane, and this dependence is incorporated in the permeability coefficient, P, or simply the permeability.

Permeability (P) is defined as the permeability flux per unit of driving force per unit of membrane thickness. The SI unit for the permeability coefficient P is provided in Table 1. A common unit for gas separation, as in the present disclosure, is the Barrer and is also presented in Table 1. The term $cm^3$ gas (STP)/$cm^2s$ refers to the volumetric trans-membrane flux of the diffusing species in terms of standard conditions of 0° C. and 1 atmosphere pressure, the term cm refers to the membrane thickness, and cm-Hg refers to the trans-membrane partial pressure driving force for the diffusing species. Permeability must be experimentally determined.

TABLE 1

| Permeability Units | | |
| --- | --- | --- |
| | Units of Permeability | |
| "Volumetric" permeability | $1 \text{ Barrer} = \dfrac{10^{-10} \cdot cm^3 \text{ gas(STP)} \cdot (cm \text{ membrane thickness})}{(cm^2 \text{ membrane area}) \cdot s \cdot (cmHg \text{ pressure})}$ | |
| "Molar" permeability | $\dfrac{mol}{m \cdot Pa \cdot s}\text{(SI units)} = \dfrac{(mol_i \text{ permeating}) \cdot (m \text{ membrane thickness})}{(m^2 \text{ membrane area}) \cdot s \cdot (Pa \text{ pressure})}$ | |

Membranes suitable for the methods and devices according to the present disclosure include dense membranes, porous membranes, asymmetric membranes, and composite membranes. In certain aspects, suitable membranes may be multilayered membranes. In other aspects, suitable membranes are prepared from inorganic materials. Dense membranes are membranes prepared from solid materials that do not have pores or voids. Materials permeate dense membranes by processes of solution and diffusion. Examples of dense membranes include silicone membranes (polydimethyl siloxane, or PDMS). Also included and provided for in the present disclosure are porous membranes that have pores of a particular range of sizes that separate on the basis of size exclusion. Examples of porous membranes suitable for use according to the present disclosure include PVDF and polysulfone membranes.

Included and provided for by the present disclosure are composite membranes that are made of more than one material, often as laminates, wherein a dense material is applied to a porous support layer. Examples of composite membranes suitable for use according to the present disclosure are EMD Millipore's GVHP hydrophobic PVDF having 1.0 μm or 0.22 μm pore sizes.

TABLE 2

| | Silicone | PTFE | PFA | FEP | ETFE | CTFE | ECTFE | PVDF | PVF | THV |
|---|---|---|---|---|---|---|---|---|---|---|
| Permeability of Fluoropolymers (100 μm thick; 23° C.) | | | | | | | | | | |
| Water vapor (g/m$^2$ · d · bar) | 36000 | 5 | 8 | 1 | 2 | 1 | 2 | 2 | 7 | 1.73 |
| Oxygen (cm$^3$/m$^2$ · d · bar) | 500 | 1500 | n/a | 2900 | 350 | 60 | 100 | 20 | 12 | 696 |
| Nitrogen (cm$^3$/m$^2$ · d · bar) | 280 | 500 | n/a | 1200 | 120 | 10 | 40 | 30 | 1 | 217 |
| CO$_2$ (cm$^3$/m$^2$ · d · bar) | 2700 | 15000 | 7000 | 4700 | 1300 | 150 | 400 | 100 | 60 | 2060 |

From Kunststoffe "Fluorocarbon films-Present situation and Future Outlook" available at kynar.com The present disclosure provides for, and includes, inner collapsible blood containers 102 prepared from membranes 113 that are characterized primarily by their permeability to oxygen. Unless indicated otherwise, a "substantially impermeable membrane" refers to membranes that are substantially impermeable to oxygen. However, in certain devices and methods, the membranes may be further characterized by the permeability or impermeability to carbon dioxide. For certain applications, the membrane material is substantially impermeable to oxygen and provides a barrier to the introduction of oxygen to the blood, blood component, or a blood collection kit comprised of multiple components. Such substantially impermeable membranes are generally used to prepare outer receptacles of the present disclosure. Suitable substantially impermeable membranes may also be used to prepare tubing for connective components of the devices and kits. Substantially impermeable membranes may comprise a monolayer or be laminated sheets or tubes having two or more layers.

The present disclosure also provides for, and includes, membranes 113 that are substantially permeable to oxygen. Membranes 113 that are substantially permeable to oxygen are used in the present disclosure for the preparation of inner collapsible blood containers 102. In certain aspects, the membranes 113 that are permeable to oxygen are also biocompatible membranes, approved and suitable for extended contact with blood that is to be transfused into a patient. Like substantially impermeable membranes, substantially permeable membranes 113 may comprise a monolayer or may comprise a laminated structure having two or more layers.

In an aspect, oxygen permeable membranes 113 having a permeability to oxygen of greater than about $2.5 \times 10^{-9}$ cm$^3$ O$_2$ (STP)/((cm$^2$ s)*(cm Hg cm$^{-1}$)) is used for the preparation of a collapsible blood container 102. In another aspect, oxygen permeable membranes 113 having a permeability to oxygen greater than about $5.0 \times 10^{-9}$ cm$^3$ O$_2$ (STP)/((cm$^2$ s)*(cm Hg cm$^{-1}$)) is used for the preparation of a collapsible blood container 102. In yet another aspect, oxygen permeable membranes 113 have a permeability to oxygen of greater than about $1.0 \times 10^{-8}$ cm$^3$ O$_2$ (STP)/((cm$^2$ s)*(cm Hg cm$^{-1}$)). In certain aspects, oxygen permeable membranes 113 suitable for use in the preparation of a collapsible blood container 102 are characterized by a Barrer value of greater than about 25. In other aspects, oxygen permeable membranes 113 suitable for use in the preparation of a collapsible blood container 102 are characterized by a Barrer value of greater than about 50. In certain other aspects, oxygen permeable membranes 113 suitable for use in the preparation of a collapsible blood container 102 are characterized by a Barrer value of greater than about 100.

In an aspect, a membrane 113 that is substantially permeable to oxygen can be dense membranes prepared from non-porous materials. Examples of suitable materials that are capable of high oxygen permeability rates include silicones, polyolefins, epoxies, and polyesters. In another aspect, membranes that are substantially permeable to oxygen can be porous membranes prepared from organic polymers. A membrane 113 that is substantially permeable to oxygen may be prepared from a material selected from the group consisting of PVDF rendered hydrophobic, nylon, cellulose esters, polysulfone, polyethersulfone, polypropylene rendered hydrophobic, and polyacrylonitrile.

The present disclosure provides for, and includes, preparing membranes 113 that are substantially permeable to oxygen, not only by selecting the material, but also by selecting and controlling the thickness. As provided above, permeability is proportional to the thickness of the membrane. Accordingly, improved permeability may be achieved by decreasing the thickness of the membrane. In certain aspects, the minimum thickness is determined by its strength and resistance to puncture and tearing.

The present disclosure also provides for, and includes, membranes 113 that are substantially permeable to oxygen that are prepared using blow molding and injection molding techniques. Suitable materials for preparing inner collapsible blood containers 102 using blow molding and injection molding include silicone materials such as Bluestar 4350, 50 durometer, Silbione grade liquid silicone rubber and Shin-Etsu KEG-2000-40A/B Liquid Silicone. The silicone durometer choice is carefully chosen for collapsibility and permeability, followed by a well-controlled wall thickness. Thinner materials will have a higher permeability. Methods to prepare blow molded and injection molded collapsible blood containers 102 are known in the art, for example, U.S. Pat. No. 4,398,642 issued to Okudaira et al.; U.S. Pat. No. 7,666,486 issued to Sato et al.; U.S. Pat. No. 8,864,735 issued to Sano et al.; and U.S. Patent Application Publication No. 2012/0146266 by Oda et al. In an aspect, a blow molded collapsible blood container 102 can be prepared using LDPE used in the manufacture of collapsible water containers. As provided below, suitable blow molded or injection molded collapsible blood containers 102 have a permeability to oxygen of at least about 25 Barrer.

In an aspect according to the present disclosure, the collapsible blood container 102 can be manufactured from microporous membrane 113 by various sealing methods such as heat sealing, thermal staking, and adhesive bonding. In one aspect according to the present disclosure, a pair of PVDF microporous membranes are bonded together around the periphery with a section of PVC inlet tubing in place in the seam using an adhesive such as Loctite 4011 in conjunction with an adhesive primer such as Loctite 770. In another aspect according to the present disclosure, a collapsible blood container can be manufactured from a pair of microporous membranes by heat sealing the 4 edges of the pair of membranes together with a section of multilayer tubing sealed into the seam to provide for fluid connectivity.

The present disclosure provides for, and includes, a collapsible blood container 102 that is prepared from more than one type of membrane 113. In an aspect, a collapsible blood container 102 comprises a first membrane 113 and a second membrane 114 suitably bonded to prepare a container. As used herein, a membrane 114 generally refers to a membrane that is identical to membrane 113. That is, a collapsible blood container 102 is generally made of two joined membranes 113. The present disclosure provides for, and includes, a collapsible blood container 102 that is prepared from a membrane 113 and a membrane 114 comprising a different material. As shown in FIG. 1C, a collapsible blood container 102 is shown to be prepared with a membrane 113 and a membrane 114. Unless indicated otherwise, it is understood that a membrane 113 and a membrane 114 may be exchanged. In another aspect, a collapsible blood container 102 comprises a membrane 113 combined with a second membrane 114 that has a permeability of less than about 30% of the permeability of first membrane 113. In certain aspects, a second membrane 114 comprises a membrane that is relatively impermeable or insufficiently permeable to provide sufficient deoxygenation on its own, but can be combined with a suitable membrane 113. In certain aspects, the second membrane 114 is relatively impermeable. In further aspects, the second membrane 114 comprises a molded membrane that incorporates ridges, baffles, or other structures to facilitate mixing. In an aspect, the second membrane 114 may comprise a rigid structure joined to an oxygen permeable membrane 113. In aspects according to the present disclosure, the second membrane 114 is heat sealed to membrane 113.

In certain aspects, the inner collapsible blood container 102 contains flow baffles located internal or external to the blood contact area that provide an increase in the turbulence inside the collapsible blood container 102 when agitated. In an aspect, baffles are located 1 to 2 inches from each other and comprise 10 to 45% of the inner collapsible blood container 102 area.

The present disclosure provides for, and includes, a collapsible blood container 102 that is substantially permeable to oxygen and is a microporous membrane prepared from polyvinylidene fluoride, or polyvinylidene difluoride (PVDF). In certain aspects, the PVDF membrane is a hydrophobic microporous membrane that is substantially permeable to oxygen.

In aspects according to the present disclosure, the microporous PVDF membrane comprises pores having a range of between 0.01 μm and 2.0 μm. In other aspects, the microporous PVDF membrane 113 comprises pores having a range of between 0.01 μm and 1.0 μm. In some aspects, a microporous PVDF membrane 113 has a pore size of between 0.03 μm and 1.0 μm in diameter. In other aspects, a microporous PVDF membrane 113 has a pore size of between 0.03 μm and 0.45 μm in diameter.

In aspects according to the present disclosure, the void fraction of a PVDF membrane 113 used to prepare a collapsible blood container 102 is between 20 and 80%. In another aspect, the void fraction of a PVDF membrane 113 used to prepare a collapsible blood container 102 is between 35 and 50%.

In certain aspects, the permeability of PVDF membranes having micropores greater than about 1.0 μm may allow fluid to permeate through the membrane, compromising both the fluid containment as well as the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic PVDF materials is not recommended as the surface tension of the material is lower and allows for fluid to seep through the pores even at the ranges stated above.

In certain aspects according to the present disclosure, the collapsible blood container 102 is prepared from a PVDF permeable membrane 113 having a pore size of between 0.1 and 0.8 μm in diameter. In other aspects, micropores of porous PVDF membranes may be from 0.22 to 0.8 μm in diameter. In an aspect, the micropores of porous PVDF membranes are from 0.2 to 1.0 μm. In another aspect, the micropores of porous PVDF membranes may be greater than 0.1 and less than 1.0 μm. In a further aspect, the micropore of the porous PVDF membrane ranges from about 0.05 to about 1.0 μm. In some aspects, the micropores of porous PVDF membranes may be greater than 0.3 or 0.4 μm. In other aspects, the micropores of porous PVDF membranes may be greater than 0.5 or 0.6 μm.

In aspects according to the present disclosure, an oxygen depletion device 10 comprises an inner collapsible blood container 102 comprising a PVDF membrane 113 having a micropore size of less than 1.0 μm. In another aspect according to the present disclosure, an oxygen depletion device 10 comprises an inner collapsible blood container 102 comprising a PVDF membrane 113 having a micropore size of less than 0.8 μm. In certain aspects according to the present disclosure, an oxygen depletion device 10 comprises an inner collapsible blood container 102 comprising a PVDF membrane 113 having a micropore size of less than 0.65 μm. In another aspect according to the present disclosure, an oxygen depletion device 10 comprises an inner collapsible blood container 102 comprising a PVDF membrane 113 having a micropore size of less than 0.45 μm.

In an aspect according to the present disclosure, an oxygen depletion device 10 comprises an inner collapsible blood container 102 comprising a PVDF membrane 113 having a micropore size of 0.1 μm. In another aspect, an oxygen depletion device 10 comprises an inner collapsible blood container 102 comprising a PVDF membrane 113 having a micropore size of 0.22 μm. In another aspect, an oxygen depletion device 10 comprises an inner collapsible blood container 102 comprising a PVDF membrane 113 having a micropore size of 0.20 μm. In a further aspect according to the present disclosure, an oxygen depletion device 10 comprises an inner collapsible blood container 102 comprising a PVDF membrane 113 having a micropore size of 0.45 μm. In yet a further aspect, an oxygen depletion device 10 comprises an inner collapsible blood container 102 comprising a PVDF membrane 113 having a micropore size of 0.65 μm. In another aspect according to the present disclosure, an oxygen depletion device 10 comprises an inner collapsible blood container 102 comprising a PVDF membrane 113 having a micropore size of 0.8 μm.

In aspects according to the present disclosure, the PVDF membrane may be less than 250 μm thick. In certain aspects, the membrane is greater than 10 μm thick. In some aspects, the PVDF membrane may be between 10 and 250 μm thick. In other aspects, the PVDF membrane may be between 10 and 125 μm thick or between 25 and 150 μm thick. In an aspect, the PVDF membrane may be between 50 and 125 μm thick, 75 and 125 μm thick, 50 and 150 μm thick, 75 and 150 μm thick, 100 and 125 μm thick, 150 and 250 μm thick, or between 25 and 150 μm thick. In an aspect, the membrane 113 of inner collapsible blood container 102 is about 20 μm thick. In another aspect, the membrane 113 of inner collapsible blood container 102 is about 30 μm thick. In yet another aspect, the membrane 113 of inner collapsible blood container 102 is about 50 μm thick. In a further aspect, the membrane 113 of inner collapsible blood container 102 is about 76 μm thick. In an aspect, the membrane 113 of inner collapsible blood container 102 is about 120 μm thick.

In certain aspects according to the present disclosure, the collapsible blood container 102 is prepared from a PVDF permeable membrane 113 that is between 100 and 125 μm thick. In certain aspects according to the present disclosure, the collapsible blood container 102 is prepared from a PVDF permeable membrane 113 having a pore size of between 0.1 μm and 0.8 μm in diameter and that is between 100 and 125 μm thick. In certain aspects according to the present disclosure, the collapsible blood container 102 is prepared from a PVDF permeable membrane 113 having a pore size of between 0.1 μm and 0.8 μm in diameter and that is between 50 and 150 μm thick.

Examples of suitable PVDF membranes for the preparation of inner collapsible blood containers that are permeable to oxygen according to the present disclosure include VVSP 115 μm thick/0.1 μm pore; GVSP 115 μm thick/0.22 μm pore; HVSP 115 μm thick/0.45 μm pore; DVSP 115 μm thick/0.65 μm pore; BVSP 115 μm thick/1.0 μm pore; VVHP 107 μm thick/0.1 μm pore; GVHP 125 μm thick/0.22 μm pore; HVHP 115 μm thick/0.45 μm pore; or DVHP 115 μm thick/0.65 μm pore.

Suitable PVDF membranes include commercially available membranes. Non-limiting examples of PVDF membranes are available from Millipore Corporation, Bedford, MA In an aspect, the PVDF membrane may be obtained from Millipore Corporation, Bedford, MA An example of such a PVDF membrane is the VVSP, GVSP, HVSP, DVSP, BVSP, VVHP, GVHP, HVHP, or DVHP.

The present disclosure provides for, and includes, a collapsible blood container 102 that is substantially permeable to oxygen and is a microporous membrane prepared from polysulfone. In certain aspects, the polysulfone membrane is a hydrophobic microporous membrane that is substantially permeable to oxygen.

In aspects according to the present disclosure, the microporous polysulfone membrane comprises pores having a range of between 0.01 μm and 2.0 μm. In other aspects, the microporous polysulfone membrane 113 comprises pores having a range of between 0.01 μm and 1.0 μm. In some aspects, a microporous polysulfone membrane 113 has a pore size of between 0.03 μm and 1.0 μm in diameter. In other aspects, a microporous polysulfone membrane 113 has a pore size of between 0.03 μm and 0.45 μm in diameter.

In aspects according to the present disclosure, the void fraction of a polysulfone membrane 113 used to prepare a collapsible blood container 102 is between 20 and 80%. In another aspect, the void fraction of a polysulfone membrane 113 used to prepare a collapsible blood container 102 is between 35 and 50%.

In certain aspects, the permeability polysulfone membranes having micropores greater than about 0.2 μm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic polysulfone materials is not recommended as the surface tension of the material is lower and allows for fluid to seep through the pores even at the ranges stated above.

In certain aspects according to the present disclosure, the collapsible blood container 102 is prepared from a polysulfone permeable membrane 113 having a pore size of between 0.3 μm and 0.8 μm in diameter. In other aspects, micropores of porous polysulfone membranes may be from 0.22 μm to 0.8 μm in diameter. In an aspect, the micropores of porous polysulfone membranes are from 0.2 μm to 1.0 μm. In another aspect, the micropores of porous polysulfone membranes may be greater than 0.1 μm and less than 1.0 μm. In a further aspect, the micropore of the porous polysulfone membrane ranges from about 0.05 μm to about 1.0 μm. In some aspects, the micropores of porous polysulfone membranes may be greater than 0.3 μm or 0.4 μm. In other aspects, the micropores of porous polysulfone membranes may be greater than 0.5 μm or 0.6 μm.

In aspects according to the present disclosure, an oxygen depletion device 10 comprises an inner collapsible blood container 102 comprising a polysulfone membrane 113 having a micropore size of less than 1.0 μm. In another aspect according to the present disclosure, an oxygen depletion device 10 comprises an inner collapsible blood container 102 comprising a polysulfone membrane 113 having a micropore size of less than 0.8 μm. In certain aspects according to the present disclosure, an oxygen depletion device 10 comprises an inner collapsible blood container 102 comprising a polysulfone membrane 113 having a micropore size of less than 0.65 μm. In another aspect according to the present disclosure, an oxygen depletion device 10 comprises an inner collapsible blood container 102 comprising a polysulfone membrane 113 having a micropore size of less than 0.45 μm.

In an aspect according to the present disclosure, an oxygen depletion device 10 comprises an inner collapsible blood container 102 comprising a polysulfone membrane 113 having a micropore size of 0.1 μm. In another aspect, an oxygen depletion device 10 comprises an inner collapsible blood container 102 comprising a polysulfone membrane 113 having a micropore size of 0.22 μm. In another aspect, an oxygen depletion device 10 comprises an inner collapsible blood container 102 comprising a polysulfone membrane 113 having a micropore size of 0.20 μm. In a further aspect according to the present disclosure, an oxygen depletion device 10 comprises an inner collapsible blood container 102 comprising a polysulfone membrane 113 having a micropore size of 0.45 μm. In yet a further aspect, an oxygen depletion device 10 comprises an inner collapsible blood container 102 comprising a polysulfone membrane 113 having a micropore size of 0.65 μm. In another aspect according to the present disclosure, an oxygen depletion device 10 comprises an inner collapsible blood container 102 comprising a polysulfone membrane 113 having a micropore size of 0.8 μm. In another aspect according to the present disclosure, an oxygen depletion device 10 comprises an inner collapsible blood container 102 comprising a polysulfone membrane 113 having a micropore size of 0.03 μm. In another aspect according to the present disclosure, an oxygen depletion device 10 comprises an inner collapsible blood container 102 comprising a polysulfone membrane 113 having a micropore size of 0.05 μm. In another aspect according to the present disclosure, an oxygen depletion device 10 comprises an inner collapsible blood container 102 comprising a polysulfone membrane 113 having a micropore size of 1.2 μm.

In aspects according to the present disclosure, the polysulfone membrane may be less than 250 μm thick. In certain aspects, the membrane is greater than 10 μm thick. In some aspects, the polysulfone membrane may be between 10 and 250 μm thick. In other aspects, the polysulfone membrane may be between 10 and 125 μm thick or 25 and 150 μm thick. In an aspect, the polysulfone membrane may be between 50 and 125 μm thick, 75 and 125 μm thick, 50 and 150 μm thick, 75 and 150 μm thick, 100 and 125 μm thick, 150 and 250 μm thick, or between 25 and 150 μm thick. In an aspect, the membrane 113 of inner collapsible blood container 102 is about 20 μm thick. In another aspect, the membrane 113 of inner collapsible blood container 102 is about 30 μm thick. In yet another aspect, the membrane 113 of inner collapsible blood container 102 is about 50 μm thick. In a further aspect, the membrane 113 of inner collapsible blood container 102 is about 76 μm thick. In an aspect, the membrane 113 of inner collapsible blood container 102 is about 120 μm thick.

In certain aspects according to the present disclosure, the collapsible blood container 102 is prepared from a polysulfone permeable membrane 113 that is between 100 and 125 μm thick. In certain aspects according to the present disclosure, the collapsible blood container 102 is prepared from a polysulfone permeable membrane 113 having a pore size of between 0.1 μm and 0.8 μm in diameter and that is between 100 and 125 μm thick. In certain aspects according to the present disclosure, the collapsible blood container 102 is prepared from a polysulfone permeable membrane 113 having a pore size of between 0.1 μm and 0.8 μm in diameter and that is between 50 and 150 μm thick.

Examples of suitable polysulfone membranes for the preparation of inner collapsible blood containers that are permeable to oxygen according to the present disclosure include SS003AH 10-250 μm thick/0.03 μm pore; SS005AH 10-250 μm thick/0.05 μm pore; SS010AH 10-250 μm thick/ 0.1 μm pore; SS020AH 10-250 μm thick/0.2 μm pore; SS045AH 10-250 μm thick/0.45 μm pore; SS065AH 10-250 μm thick/0.65 μm pore; SS080AH 10-250 μm thick/0.8 μm pore; or SS120AH 10-250 μm thick/1.2 μm pore.

Suitable polysulfone membranes include commercially available membranes. Non-limiting examples of polysulfone membranes are available from Pacific Membranes. In an aspect, the polysulfone membrane may be SS120AH, SS080AH, SS065AH, SS045AH, SS020AH, SS010AH, SS005AH, or SS003AH.

The present disclosure provides for, and includes, a collapsible blood container 102 that is substantially permeable to oxygen and is a microporous membrane prepared from polyolefin. In certain aspects, the polyolefin membrane is a hydrophobic microporous membrane that is substantially permeable to oxygen.

In aspects according to the present disclosure, the microporous polyolefin membrane comprises pores having a range of between 0.01 μm and 2.0 μm. In other aspects, the microporous polyolefin membrane 113 comprises pores having a range of between 0.01 μm and 1.0 μm. In some aspects, a microporous polyolefin membrane 113 has a pore size of between 0.03 μm and 1.0 μm in diameter. In other aspects, a microporous polyolefin membrane 113 has a pore size of between 0.03 μm and 0.45 μm in diameter.

In aspects according to the present disclosure, the void fraction of a polyolefin membrane 113 used to prepare a collapsible blood container 102 is between 20 and 80%. In another aspect, the void fraction of a polyolefin membrane 113 used to prepare a collapsible blood container 102 is between 35 and 50%.

In certain aspects, the permeability polyolefin membranes having micropores greater than about 1.0 μm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic polyolefin materials is not recommended as the surface tension of the material is lower and allows for fluid to seep through the pores even at the ranges stated above.

In certain aspects according to the present disclosure, the collapsible blood container 102 is prepared from a polyolefin permeable membrane 113 having a pore size of between 0.1 μm and 0.8 μm in diameter. In other aspects, micropores of porous polyolefin membranes may be from 0.22 μm to 0.8 μm in diameter. In an aspect, the micropores of porous polyolefin membranes are from 0.2 μm to 1.0 μm. In another aspect, the micropores of porous polyolefin membranes may be greater than 0.1 and less than 1.0 μm. In a further aspect, the micropore of the porous polyolefin membrane ranges from about 0.05 μm to about 1.0 μm. In some aspects, the micropores of porous polyolefin membranes may be greater than 0.3 or 0.4 μm. In other aspects, the micropores of porous polyolefin membranes may be greater than 0.5 or 0.6 μm.

In aspects according to the present disclosure, an oxygen depletion device 10 comprises an inner collapsible blood container 102 comprising a polyolefin membrane 113 having a micropore size of less than 1.0 μm. In another aspect according to the present disclosure, an oxygen depletion device 10 comprises an inner collapsible blood container 102 comprising a polyolefin membrane 113 having a micropore size of less than 0.8 μm. In certain aspects according to the present disclosure, an oxygen depletion device 10 comprises an inner collapsible blood container 102 comprising a polyolefin membrane 113 having a micropore size of less than 0.65 μm. In another aspect according to the present disclosure, an oxygen depletion device 10 comprises an inner collapsible blood container 102 comprising a polyolefin membrane 113 having a micropore size of less than 0.45 μm.

In an aspect according to the present disclosure, an oxygen depletion device 10 comprises an inner collapsible blood container 102 comprising a polyolefin membrane 113 having a micropore size of 0.1 μm. In another aspect, an oxygen depletion device 10 comprises an inner collapsible blood container 102 comprising a polyolefin membrane 113 having a micropore size of 0.22 μm. In another aspect, an oxygen depletion device 10 comprises an inner collapsible blood container 102 comprising a polyolefin membrane 113 having a micropore size of 0.20 μm. In a further aspect according to the present disclosure, an oxygen depletion device 10 comprises an inner collapsible blood container 102 comprising a polyolefin membrane 113 having a micropore size of 0.45 μm. In yet a further aspect, an oxygen depletion device 10 comprises an inner collapsible blood container 102 comprising a polyolefin membrane 113 having a micropore size of 0.65 μm. In another aspect according to the present disclosure, an oxygen depletion device 10 comprises an inner collapsible blood container 102 comprising a polyolefin membrane 113 having a micropore size of 0.8 μm.

In aspects according to the present disclosure, the polyolefin membrane may be less than 250 μm thick. In certain aspects, the membrane is greater than 10 μm thick. In some aspects, the polyolefin membrane may be between 10 and 250 μm thick. In other aspects, the polyolefin membrane may be between 10 and 125 μm thick or between 25 and 150 μm thick. In an aspect, the polyolefin membrane may be between 50 and 125 μm thick, 75 and 125 μm thick, 50 and 150 μm thick, 75 and 150 μm thick, 100 and 125 μm thick, 150 and 250 μm thick, or between 25 and 150 μm thick. In an aspect, the membrane 113 of inner collapsible blood container 102 is about 20 μm thick. In another aspect, the membrane 113 of inner collapsible blood container 102 is about 30 μm thick. In yet another aspect, the membrane 113 of inner collapsible blood container 102 is about 50 μm thick. In a further aspect, the membrane 113 of inner collapsible blood container 102 is about 76 μm thick. In an aspect, the membrane 113 of inner collapsible blood container 102 is about 120 μm thick.

In certain aspects according to the present disclosure, the collapsible blood container 102 is prepared from a polyolefin permeable membrane 113 that is between 100 and 125 μm thick. In certain aspects according to the present disclosure, the collapsible blood container 102 is prepared from a polyolefin permeable membrane 113 having a pore size of between 0.1 μm and 0.8 μm in diameter and that is between 100 μm and 125 μm thick. In certain aspects according to the present disclosure, the collapsible blood container 102 is prepared from a polyolefin permeable membrane 113 having a pore size of between 0.1 μm and 0.8 μm in diameter and that is between 50 μm and 150 μm thick.

Examples of suitable polyolefin membranes for the preparation of inner collapsible blood containers that are permeable to oxygen according to the present disclosure include those described in U.S. Pat. No. 4,440,815 issued to Zomorodi et al.

The present disclosure provides for, and includes, a collapsible blood container 102 that is substantially permeable to oxygen and is a microporous membrane prepared from polytetrafluoroethylene (PTFE). In certain aspects, the PTFE membrane is a hydrophobic microporous membrane that is substantially permeable to oxygen.

In aspects according to the present disclosure, the microporous PTFE membrane comprises pores having a range of between 0.01 μm and 2.0 μm. In other aspects, the microporous PTFE membrane 113 comprises pores having a range of between 0.01 μm and 1.0 μm. In some aspects, a microporous PTFE membrane 113 has a pore size of between 0.03 μm and 1.0 μm in diameter. In other aspects, a microporous PTFE membrane 113 has a pore size of between 0.03 μm and 0.45 μm in diameter.

In aspects according to the present disclosure, the void fraction of a PTFE membrane 113 used to prepare a collapsible blood container 102 is between 20 and 80%. In another aspect, the void fraction of a PTFE membrane 113 used to prepare a collapsible blood container 102 is between 35 and 50%.

In certain aspects, the permeability PTFE membranes having micropores greater than about 1.0 μm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°.

As used herein and known in the art, the contact angle quantifies the wettability of a solid surface and is theoretically described by Young's equation. In certain aspects according to the present disclosure, the use of non-hydrophobic PTFE materials is not recommended as the surface tension of the material is lower and allows for fluid to seep through the pores even at the ranges stated above.

In certain aspects according to the present disclosure, the collapsible blood container 102 is prepared from a PTFE permeable membrane 113 having a pore size of between 0.1 μm and 0.8 μm in diameter. In other aspects, micropores of porous PTFE membranes may be from 0.22 μm to 0.8 μm in diameter. In an aspect, the micropores of porous PTFE membranes are from 0.2 μm to 1.0 μm. In another aspect, the micropores of porous PTFE membranes may be greater than 0.1 and less than 1.0 μm. In a further aspect, the micropore of the porous PTFE membrane ranges from about 0.05 μm to about 1.0 μm. In some aspects that micropores of porous PTFE membranes may be greater than 0.3 or 0.4 μm. In other aspects, the micropores of porous PTFE membranes may be greater than 0.5 or 0.6 μm.

In aspects according to the present disclosure, an oxygen depletion device 10 comprises an inner collapsible blood container 102 comprising a PTFE membrane 113 having a micropore size of less than 1.0 μm. In another aspect according to the present disclosure, an oxygen depletion device 10 comprises an inner collapsible blood container 102 comprising a PTFE membrane 113 having a micropore size of less than 0.8 μm. In certain aspects according to the present disclosure, an oxygen depletion device 10 comprises an inner collapsible blood container 102 comprising a PTFE membrane 113 having a micropore size of less than 0.65 μm. In another aspect according to the present disclosure, an oxygen depletion device 10 comprises an inner collapsible blood container 102 comprising a PTFE membrane 113 having a micropore size of less than 0.45 μm.

In an aspect according to the present disclosure, an oxygen depletion device 10 comprises an inner collapsible blood container 102 comprising a PTFE membrane 113 having a micropore size of 0.1 μm. In another aspect, an oxygen depletion device 10 comprises an inner collapsible blood container 102 comprising a PTFE membrane 113 having a micropore size of 0.22 μm. In another aspect, an oxygen depletion device 10 comprises an inner collapsible blood container 102 comprising a PTFE membrane 113 having a micropore size of 0.20 μm. In a further aspect according to the present disclosure, an oxygen depletion device 10 comprises an inner collapsible blood container 102 comprising a PTFE membrane 113 having a micropore size of 0.45 μm. In yet a further aspect, an oxygen depletion device 10 comprises an inner collapsible blood container 102 comprising a PTFE membrane 113 having a micropore size of 0.65 μm. In another aspect according to the present disclosure, an oxygen depletion device 10 comprises an inner collapsible blood container 102 comprising a PTFE membrane 113 having a micropore size of 0.8 μm.

In aspects according to the present disclosure, the PTFE membrane 113 may be less than 250 μm thick. In certain aspects, the membrane is greater than 10 μm thick. In some aspects the PTFE membrane 113 may be between 10 and 250 μm thick. In other aspects, the PTFE membrane 113 may be between 10 and 125 or 25 and 150 μm thick. In an aspect, the PTFE membrane 113 may be between 50 and 125 μm thick, 75 and 125 μm thick, 50 and 150 μm thick, 75 and 150 μm thick, 100 and 125 μm thick, 150 and 250 μm thick or between 25 and 150 μm thick. In another aspect, the membrane 113 of inner collapsible blood container 102 is about 30 μm. In yet another aspect, the membrane 113 of inner collapsible blood container 102 is about 50 μm. In a further aspect, the membrane 113 of inner collapsible blood container 102 is about 76 μm. In an aspect, the membrane 113 of inner collapsible blood container 102 is about 120 μm thick, 100 and 125 μm thick, 150 and 250 μm thick or between 25 and 150 μm thick.

In certain aspects according to the present disclosure, the collapsible blood container 102 is prepared from a PTFE permeable membrane 113 that is between 100 and 125 μm thick. In certain aspects according to the present disclosure, the collapsible blood container 102 is prepared from a PTFE permeable membrane 113 having a pore size of between 0.1 μm and 0.8 μm in diameter and that is between 100 and 125 μm thick. In certain aspects according to the present disclosure, the collapsible blood container 102 is prepared from a PTFE permeable membrane 113 having a pore size of between 0.1 μm and 0.8 μm in diameter and that is between 50 and 150 μm thick.

Examples of suitable PTFE membranes for the preparation of inner collapsible blood containers that are permeable to oxygen according to the present disclosure include the Poreflon® FP, WP, and HP series PTFE membranes from Sumitomo Electric Interconnect Products, San Marcos, CA, and Tetratex® 2 from Donaldson Membranes, Ivyland, PA Suitable PTFE membranes include commercially available membranes. Non-limiting examples of PTFE membranes are available from Sumitomo Electric Interconnect Products, San Marcos, CA, and Donaldson Membranes, Ivyland, PA In an aspect, the PTFE membrane may be FP-010 from Sumitomo Electric Interconnect Products, San Marcos, CA In certain aspects, suitable membranes that are substantially permeable to oxygen may be multilayered membranes. In certain aspects, the multilayered membranes are hydrophobic microporous membranes that are substantially permeable to oxygen. Suitable multilayered membranes include multilayered membranes having two or more materials selected from the group consisting of PVDF rendered hydrophobic, nylon, cellulose esters, polysulfone, polyethersulfone, polypropylene rendered hydrophobic, and polyacrylonitrile.

The present disclosure provides for, and includes, a collapsible blood container 102 that is substantially permeable to oxygen and is a microporous membrane prepared from an extruded, woven, non-woven single layer or multilayered membrane. In certain aspects, the multilayered membrane is a hydrophobic microporous membrane that is substantially permeable to oxygen.

In aspects according to the present disclosure, the microporous multilayered membrane comprises pores having a range of between 0.01 micrometer (μm) and 2.0 μm. In other aspects, the microporous multilayered membrane 113 comprises pores having a range of between 0.01 μm and 1.0 μm. In some aspects, a microporous multilayered membrane 113 has a pore size of between 0.03 μm and 1.0 μm in diameter. In other aspects, a microporous multilayered membrane 113 has a pore size of between 0.03 μm and 0.45 μm in diameter.

In aspects according to the present disclosure, the void fraction of a multilayered membrane 113 used to prepare a collapsible blood container 102 is between 20 and 80%. In another aspect, the void fraction of a multilayered membrane 113 used to prepare a collapsible blood container 102 is between 35 and 50%.

In certain aspects, the permeability of multilayered membranes having micropores greater than about 1.0 μm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic multilayered materials is not recommended as the surface tension of the material is lower and allows for fluid to seep through the pores even at the ranges stated above.

In certain aspects according to the present disclosure, the collapsible blood container 102 is prepared from a multilayered permeable membrane 113 having a pore size of between 0.1 μm and 0.8 μm in diameter. In other aspects, micropores of porous multilayered membranes may be from 0.22 μm to 0.8 μm in diameter. In an aspect, the micropores of porous multilayered membranes are from 0.2 and to 1.0 μm. In another aspect, the micropores of porous multilayered membranes may be greater than 0.1 and less than 1.0 μm. In a further aspect, the micropore of the porous multilayered membrane ranges from about 0.05 μm to about 1.0 μm. In some aspects, the micropores of porous multilayered membranes may be greater than 0.3 or 0.4 μm. In other aspects, the micropores of porous multilayered membranes may be greater than 0.5 or 0.6 μm.

In aspects according to the present disclosure, an oxygen depletion device 10 comprises an inner collapsible blood container 102 comprising a multilayered membrane 113 having a micropore size of less than 1.0 μm. In another aspect according to the present disclosure, an oxygen depletion device 10 comprises an inner collapsible blood container 102 comprising a multilayered membrane 113 having a micropore size of less than 0.8 μm. In certain aspects according to the present disclosure, an oxygen depletion device 10 comprises an inner collapsible blood container 102 comprising a multilayered membrane 113 having a micropore size of less than 0.65 μm. In another aspect according to the present disclosure, an oxygen depletion device 10 comprises an inner collapsible blood container 102 comprising a multilayered membrane 113 having a micropore size of less than 0.45 μm.

In an aspect according to the present disclosure, an oxygen depletion device 10 comprises an inner collapsible blood container 102 comprising a multilayered membrane 113 having a micropore size of 0.1 μm. In another aspect, an oxygen depletion device 10 comprises an inner collapsible blood container 102 comprising a multilayered membrane 113 having a micropore size of 0.22 μm. In another aspect, an oxygen depletion device 10 comprises an inner collapsible blood container 102 comprising a multilayered membrane 113 having a micropore size of 0.20 μm. In a further aspect according to the present disclosure, an oxygen depletion device 10 comprises an inner collapsible blood container 102 comprising a multilayered membrane 113 having a micropore size of 0.45 μm. In yet a further aspect, an oxygen depletion device 10 comprises an inner collapsible blood container 102 comprising a multilayered membrane 113 having a micropore size of 0.65 μm. In another aspect according to the present disclosure, an oxygen depletion device 10 comprises an inner collapsible blood container 102 comprising a multilayered membrane 113 having a micropore size of 0.8 μm.

In aspects according to the present disclosure, the multilayered membrane 113 may be less than 250 μm thick. In certain aspects, the membrane is greater than 10 μm thick. In some aspects the multilayered membrane 113 may be between 10 and 250 μm thick. In other aspects, the multilayered membrane may be between 10 and 125 μm thick or 25 and 150 μm thick. In an aspect, the multilayered membrane 113 may be between 50 and 125 μm thick, 75 and 125 μm thick, 50 and 150 μm thick, 75 and 150 μm thick, 100 and 125 μm thick, 150 and 250 μm thick or between 25 and 150 μm thick, 100 and 125 μm thick, 150 and 250 μm thick or between 25 and 150 μm thick. In another aspect, the membrane 113 of inner collapsible blood container 102 is about 30 μm. In yet another aspect, the membrane 113 of inner collapsible blood container 102 is about 50 μm. In a further aspect, the membrane 113 of inner collapsible blood container 102 is about 76 μm. In an aspect, the membrane 113 of inner collapsible blood container 102 is about 120 μm thick In certain aspects according to the present disclosure, the collapsible blood container 102 is prepared from a multilayered permeable membrane 113 that is between 100 and 125 μm thick. In certain aspects according to the present disclosure, the collapsible blood container 102 is prepared from a multilayered permeable membrane 113 having a pore size of between 0.1 μm and 0.8 μm in diameter and that is between 100 μm and 125 μm thick. In certain aspects according to the present disclosure, the collapsible blood container 102 is prepared from a multilayered permeable membrane 113 having a pore size of between 0.1 μm and 0.8 μm in diameter and that is between 50 μm and 150 μm thick.

The present disclosure provides for, and includes, a collapsible blood container 102 that is substantially permeable to oxygen and is a membrane prepared from polyvinyl chloride (PVC). In aspects according the present disclosure, the collapsible blood container 102 can be prepared from a PVC membrane having a thickness of between 5 μm and 250 μm, and more preferably between about 10 μm and about 100 μm.

The use of PVC in the manufacture of collapsible blood containers is well known in the art. The use of various plasticizers in various PVC formulations is also well known in the art, and includes the use of diethylhexyl phthalate (DEHP) for long term storage of red blood cells. Typical manufacture of collapsible blood containers from PVC-DEHP utilizes radiofrequency (RF) welding of a pair of films to conveniently fabricate a bag structure, with such individual films having a thickness of about 350 μm to about 400 μm. An exemplary PVC-DEHP film is the Renolit ES-3000 film (American Renolit Corp., City of Commerce, CA).

Due to the relatively low oxygen permeability of such films and the need for higher oxygen permeability for platelet storage, other plasticizers for PVC have found utility in the fabrication of collapsible blood containers and include the use of citrate, among others (see, for example, "The Role of Poly(Vinyl Chloride) in Healthcare" by Colin R. Blass, copyright 2001 Rapra Technology, Ltd., ISBN:1-85957-258-8). A suitable example of a PVC-citrate film is the Renolit ES-4000 film (American Renolit Corp., City of Commerce, CA).

The present disclosure provides for suitable PVC materials for use in a collapsible blood container 102 that is substantially permeable to oxygen. The use of a PVC-citrate film such as Renolit ES-4000 having a thickness of from about 5 μm to about 250 μm, and more preferably from about 10 μm to about 100 μm is suitable for providing a collapsible blood container having the desired characteristics of high oxygen permeability, RF welding and joining, and high tensile strength.

The present disclosure provides for, and includes, a collapsible blood container 102 that is substantially permeable to oxygen and is a membrane prepared from silicone. In aspects according to the present disclosure, the collapsible blood container 102 can be prepared from a silicone membrane having a thickness of between 15 μm and 100 μm. In aspects according the present disclosure, the collapsible blood container 102 can be prepared from a silicone membrane having a thickness of between 5 μm and 500 μm. In other aspects, the collapsible blood container 102 can have a thickness of between 5 μm and 200 μm. In other aspects, the collapsible blood container 102 can have a thickness of between 20 μm and 120 μm. In another aspect the collapsible blood container 102 is between 30 μm and 120 μm thick. In yet another aspect, the collapsible blood container 102 is between 50 μm and 120 μm thick. In a further aspect, the thickness of the collapsible blood container 102 can be between 76 μm and 120 μm. In another aspect the collapsible blood container 102 is between 20 μm and 50 μm thick. The present disclosure provides for, and includes, a collapsible blood container 102 that is 20 μm in thickness. In another aspect, the collapsible blood container 102 is 15 μm thick. In another aspect, the collapsible blood container 102 is 30 μm thick. In yet another aspect, the collapsible blood container 102 is 50 μm thick. In an additional aspect, the collapsible blood container 102 is 120 μm thick.

In aspects according the present disclosure, the collapsible blood container 102 can be prepared from a silicone membrane having a thickness of between 20 μm and 400 μm. In other aspects, the collapsible blood container 102 can have a thickness of between 20 μm and 200 μm. In other aspects, the collapsible blood container 102 can have a thickness of between 40 μm and 300 μm. In another aspect, the collapsible blood container 102 is between 40 μm and 400 μm thick. In yet another aspect, the collapsible blood container 102 is between 300 μm and 450 μm thick. In a further aspect, the thickness of the collapsible blood container 102 can be between 350 μm and 450 μm. The present disclosure provides for, and includes, a collapsible blood container 102 that is about 450 μm in thickness. In another aspect, the collapsible blood container 102 is 425 μm thick. In yet another aspect, the collapsible blood container 102 is 400 μm thick. In an additional aspect, the collapsible blood container 102 is 350 μm thick.

Suitable silicone membranes include commercially available membranes. Non-limiting examples of silicone membranes are available from Wacker Silicones, such as the Silpuran® brand of medical grade silicone sheet membranes (Wacker Silicones, Adrian, MI) and Polymer Sciences PS-1033 P-Derm® silicone elastomer membrane (Polymer Sciences, Inc., Monticello, IN). In an aspect, the silicone membrane may be Polymer Sciences PS-1033 or Wacker Silpuran® 6000 silicone. Silicone membranes can be prepared from various liquid silicone rubber (LSR) materials, which are available from a number of silicone suppliers, such as Wacker Silicones (Adrian, MI), Shin-Etsu Silicones of America (Akron, OH), NuSil Technology (Carpenteria, CA), and Blue Star Silicones (East Brunswick, NJ), to name a few.

In an aspect according to the present disclosure, a collapsible blood container 102 can be manufactured from silicone by various molding methods such as compression molding, injection molding, and insert molding, and also adhesive bonding of silicone sheets using silicone adhesives. In one aspect according to the present disclosure, a pair of silicone sheets are bonded together around the periphery with a section of silicone inlet tubing in place in the seam using silicone adhesive. In another aspect according to the present disclosure, a silicone liquid rubber is injection molded over a form to create a three-sided shape, which is then further bonded to closure on the remaining fourth side around a silicone inlet tube using a silicone adhesive. In another aspect according to the present disclosure, a silicone liquid rubber is injection molded over a form to create a three-sided shape, which is then insert molded onto a closure shape on the remaining fourth side that incorporates an inlet tubing into the closure shape.

The present disclosure provides for, and includes, a collapsible blood container 102 having resistance to tearing. As used herein, "tear resistance" or "tear strength" is measured in kN/m. In aspects according the present disclosure, the collapsible blood container 102 should be prepared from oxygen permeable materials that are also resistant to tearing. Measures of tear resistance are known in the art, for example, ASTM D-412, which can also be used to measure tensile strength, modulus, and elongations. In certain aspects, collapsible blood container 102 should be prepared from oxygen permeable materials that are resistant to the formation of a tear (e.g., tear initiation). Methods of measuring tear initiation and tear propagation are known in the art, for example ASTM D-624. Other methods include measuring the tensile strength and the elongation at break according to DIN 53 504-S1.

In an aspect according to the present disclosure, a collapsible blood container 102 should be prepared from oxygen permeable materials having a tensile strength of at least 2.4 N/mm$^2$.

The present disclosure provides for, and includes, sorbents capable of binding to and removing oxygen from an environment. Unless provided otherwise, the term "sorbent" refers to oxygen sorbents and scavengers. As used herein, "oxygen scavenger" or "oxygen sorbent" is a material that binds irreversibly to or combines with $O_2$ under the conditions of use. The term "oxygen sorbent" may be used interchangeably herein with "oxygen scavenger." In certain aspects according the present disclosure, a material may bind to or combines with oxygen irreversibly. In other aspects, oxygen may bind to a sorbent material and have a very slow rate of release, $k_{off}$. In an aspect, the oxygen may chemically react with some component of the material and be converted into another compound. Any material where the off-rate of bound oxygen is much less than the residence time of the blood can serve as an oxygen scavenger.

As used herein, the amount of sorbent is provided as having a certain binding capacity of oxygen as measured by volume (e.g., cubic centimeters (cc) or milliliters (ml)) at standard temperature and pressure (e.g., 0° C. (273.15 Kelvin) and $1.01 \times 10^5$ pa (100 kPa, 1 bar, 0.986 atm, 760 mmHg) of pressure). In other aspects, oxygen sorbents and scavengers are further capable of binding to and removing carbon dioxide from an environment. In certain aspects, sorbent 103 may be a mixture of non-toxic inorganic and/or organic salts and ferrous iron or other materials with high reactivity toward oxygen, carbon dioxide, or oxygen and carbon dioxide. In certain aspects, an oxygen sorbent or scavenger is combined with a carbon dioxide sorbent. In other aspects, the presence or absence of carbon dioxide binding capabilities of an oxygen sorbent is not necessary.

Suitable oxygen sorbents or scavengers are known in the art. Suitable oxygen sorbents according to the present disclosure have minimum oxygen adsorption rates of 0.44 ml/min. Sorbents having suitable adsorption profiles bind at least 45 ml $O_2$ within 60 minutes, 70 ml $O_2$ within 120 minutes, and 80 ml $O_2$ within 180 minutes. Suitable sorbents may have both higher capacity and binding rates.

Non-limiting examples of oxygen scavengers or sorbents include iron powders and organic compounds. Examples of $O_2$ sorbents include chelates of cobalt, iron, and Schiff bases. Additional non-limiting examples for $O_2$ sorbents may be found in U.S. Pat. No. 7,347,887 issued to Bulow et al., U.S. Pat. No. 5,208,335, issued to Ramprasad et al., and U.S. Pat. No. 4,654,053 issued to Sievers et al.; each of which is hereby incorporated by reference in their entireties. Oxygen sorbent materials may be formed into or incorporated in fibers, microfibers, microspheres, microparticles, and foams.

In certain aspects, suitable sorbents include those obtainable from Multisorb Technologies (Buffalo, NY), Sorbent Systems/Impak Corporation (Los Angeles, CA) or Mitsubishi Gas Chemical America (MGC) (New York, NY). Exemplary oxygen sorbents include Multisorb Technologies StabilOx® packets, Sorbent Systems P/N SF100PK100 100 cc oxygen absorber, and Mitsubishi Gas Chemical America Ageless® SS-200 oxygen absorber. MGC also provides sorbents suitable for the methods and devices of the present disclosure. Such suitable oxygen sorbents include the MGC Ageless® and SS-200 oxygen absorber.

In aspects according to the present disclosure, a sorbent may be an oxidizable organic polymer having a polymeric backbone and a plurality of pendant groups. Examples of sorbents with a polymeric backbone include a saturated hydrocarbon (<0.01% carbon-carbon double bonds). In some aspects, the backbone can contain monomers of ethylene or styrene. In an aspect, a polymeric backbone may be ethylenic. In another aspect, an oxidizable organic compound may be ethylene/vinyl cyclohexene copolymer (EVCH). Additional examples of substituted moieties and catalysts are provided in U.S. Patent Publication No. 2003/0183801 by Yang et al., hereby incorporated by reference in its entirety. In additional aspects, an oxidizable organic polymer can also comprise substituted hydrocarbon moieties. Examples of oxygen scavenging polymers include those described by Ching et al., International Patent Publication WO99/48963, hereby incorporated by reference in its entirety. Oxygen scavenging materials may include those provided in U.S. Pat. No. 7,754,798 issued to Ebner et al., U.S. Pat. No. 7,452,601 issued to Ebner et al., or U.S. Pat. No. 6,387,461 issued to Ebner et al., each of which are hereby incorporated by reference in their entireties.

As used herein, sorbents of the present disclosure may be either free or contained in a permeable enclosure, container, envelope, etc. In certain aspects, sorbent is provided in one or more sachets made of materials having high porosity and essentially no resistance to the transport of gases. Examples of such materials include spun polyester films, perforated metallic foils, and combinations thereof.

The present disclosure further includes, and provides for, sorbent incorporated as one or more laminated layers of an outer article substantially impermeable to oxygen. Polymeric sorbents such as those described above may be laminated to sheets used to prepare an outer receptacle using methods known in the art, including soft contact lamination, thermal lamination, or solvent lamination.

The present disclosure further includes, and provides for, sorbents formed inside the pores of porous micro-glass fibers or encapsulated in other inert materials. The encapsulation of transition-metal complexes within the pores of a porous material may be achieved by using a ship-in-a-bottle synthesis in which the final molecule is prepared inside the pores by reacting smaller precursors. Examples of such encapsulated sorbents are known in the art, for example, as described by Kuraoka, et al., "Ship-in-a-bottle synthesis of a cobalt phthalocyanine/porous glass composite membrane for oxygen separation," *Journal of Membrane Science,* 286(1-2):12-14 (2006), herein incorporated by reference in its entirety. In some aspects, porous glass fibers may be manufactured as provided in U.S. Pat. No. 4,748,121 issued to Beaver et al., herein incorporated by reference in its entirety. In another aspect, a sorbent can formed as a porous sheet product using papermaking/non-woven wet-laid equipment. Sheets with $O_2$ scavenging formulations may be as described in U.S. Pat. No. 4,769,175 issued to Inoue, herein incorporated by reference in its entirety, which can be formed and then encapsulated with a silicone film.

As used herein, "carbon dioxide scavenger" is a material that binds to or combines with carbon dioxide under the conditions of use. The term "carbon dioxide sorbent" may be used interchangeably herein with "carbon dioxide scavenger." In certain aspects, carbon dioxide sorbents may be non-reactive, or minimally reactive with oxygen. In other embodiments, oxygen sorbents may exhibit a secondary functionality of carbon dioxide scavenging. Carbon dioxide scavengers include metal oxides and metal hydroxides. Metal oxides react with water to produce metal hydroxides. The metal hydroxide reacts with carbon dioxide to form water and a metal carbonate. In certain aspects according the present disclosure, a material may bind to or combine with $CO_2$ irreversibly. In aspects according to the present disclosure, a material may bind $CO_2$ with higher affinity than hemoglobin. In other aspects, a sorbent material may bind $CO_2$ with high affinity such that the carbonic acid present in the blood or RBC cytoplasm is released and absorbed by the sorbent. In other aspects, $CO_2$ binds to a sorbent material and has a very slow rate of release, $k_{off}$. In an aspect, the carbon dioxide can chemically react with some component of the material and be converted into another compound.

Carbon dioxide scavengers are known in the art. In certain aspects according to the present disclosure, a carbon dioxide scavenger may be calcium oxide. Reaction of calcium oxide with water produces calcium hydroxide that may react with carbon dioxide to form calcium carbonate and water. In certain aspects according the present disclosure, the water for the production of calcium hydroxide is obtained via diffusion of blood derived water vapor through the inner oxygen permeable container. In another aspect, the water may be provided by the environment through the outer receptacle that is substantially impermeable to oxygen. In yet another aspect, the water may be included with the outer receptacle of the oxygen depletion device.

Non-limiting examples of $CO_2$ scavengers include oxygen scavengers and carbon dioxide scavengers provided by Multisorb Technologies (Buffalo, NY). Oxygen scavengers may exhibit a secondary functionality of carbon dioxide scavenging.

In aspects according to the present disclosure, $O_2$ depletion media and $CO_2$ depletion media may be blended to a desired ratio to achieve desired results.

The present disclosure further includes and provides for sorbents contained in sachets. As used herein, a "sachet" is any enclosure that encloses and contains an oxygen sorbent, a carbon dioxide sorbent, or a combination of oxygen and carbon dioxide sorbent(s). Sachets according the present disclosure are contained within overwrap material that is both oxygen and carbon dioxide permeable. In certain embodiments, the overwrap material may be a combination of two or more materials, at least one of the materials being oxygen and carbon dioxide permeable. Suitable overwrap materials have a known biocompatible profile or meet ISO 10993.

Sachets are sealed so that the sorbent contents are wholly contained within the overwrap material and do not allow the sorbent to leak or otherwise exit its overwrap package. Sachets may take any shape, though typically take a rectangular or square shape. In an aspect, the sachet is about 50×60 mm. In an aspect, the oxygen sorbent 103 binds 30 cc oxygen per sachet at STP. In an aspect, the oxygen sorbent 103 binds 60 cc oxygen per sachet at STP. In an aspect, the oxygen sorbent 103 binds 120 cc oxygen per sachet at STP. In an aspect, the oxygen sorbent 103 binds from 30 to 120 cc oxygen per sachet at STP. In an aspect, the oxygen sorbent 103 binds from 30 to 120 cc oxygen per sachet at STP. In an aspect, the oxygen sorbent 103 binds from 50 to 200 cc oxygen per sachet at STP. In certain aspects according to the present disclosure, a sachet has a total oxygen adsorption capacity of 100 cc $O_2$ at STP. In certain other aspects of the present disclosure, a sachet has a total oxygen absorption capacity of at least 200 cc $O_2$ at STP.

In aspects according to the present disclosure, the oxygen sorbent 103 may be provided in one or more sachets. In another aspect, the oxygen sorbent 103 is provide in a single larger sachet. In other aspects, the oxygen sorbent 103 is provided in two sachets distributed within the headspace between the inner collapsible container 102 and the outer receptacle 101. In yet other aspects, the oxygen sorbent 103 is provided in four sachets distributed within the headspace between the inner collapsible container 102 and the outer receptacle 101. In aspects according to the present disclosure, an oxygen depletion device 10 may comprise 2 to 20 sorbent packages.

In aspects according to the present disclosure, oxygen depletion device 10 includes from 1 to 50 grams of sorbent 103 contained in one or more sachets. In an aspect, an oxygen depletion device 10 includes from 1 to 100 grams of sorbent 103 contained in one or more sachets. In an aspect, an oxygen depletion device 10 includes from 25 to 75 grams of sorbent 103 contained in one or more sachets. In a further aspect, an oxygen depletion device 10 includes about 25 grams of sorbent 103. In yet another aspect, oxygen depletion device 10 includes about 50 grams of sorbent 103. In an aspect, an oxygen depletion device 10 includes about 35 or 45 grams of sorbent 103 contained in one or more sachets. In an aspect, an oxygen depletion device 10 includes about 10 or 15 grams of sorbent 103 contained in one or more sachets. The sachets can be square, rectangular, circular, or elliptical and have a perimeter of 40 to 150 mm.

Sachets according to the present disclosure may further include a carbon dioxide sorbent. In an aspect, an oxygen sorbent 103 also provides for carbon dioxide adsorption. In an aspect, the oxygen sorbent 103 binds 30 cc carbon dioxide at STP. In an aspect, the oxygen sorbent 103 binds at least 170 cc oxygen and at least 30 cc carbon dioxide, where both gases are measured at STP.

The present disclosure provides for, and includes, an outer receptacle 101 that is substantially impermeable to oxygen. As discussed above, the integrity of the oxygen barrier should be maintained when joining, welding, folding, or otherwise assembling an outer receptacle 101. Failures in assembly of the outer receptacle 101 compromises the shelf life of an oxygen depletion device 10 or renders it unable to perform its intended purpose of depleting oxygen from blood. Importantly, blood that is inadequately depleted of oxygen does not realize the benefits of depletion during storage and may have significant negative consequences when transfused into a patient. In addition to satisfying the requirements for blood collection and depletion, it is routine for blood to be sampled through standardized ports 303 as well as for various additives to be introduced into the collected blood. More specifically, nearly all collected blood is provided with an anticoagulant at or during collection.

To address the need to introduce materials into the collected blood, and to provide for the transfer of blood that has been depleted of oxygen to an appropriate anaerobic storage bag, an oxygen depletion device 10 may further include one or more inlets/outlets 30. As provided herein, special care in the assembly of the outer receptacle 101 (and outer receptacle 201) is necessary to ensure that when the oxygen impermeable outer receptacle 101 (and outer receptacle 201) is traversed, the inlet/outlet 30 does not become a source of unwanted oxygen ingress.

In aspects according to the present disclosure, the outer receptacle 101 includes one or more inlets/outlets 30. In certain aspects, the one or more inlet/outlets 30 further comprise a spike port 303.

It is notable that few materials provide complete impermeability and that even the high impermeability of materials can be compromised when joining, welding, folding, or otherwise assembling an outer receptacle 101. As will be discussed below, oxygen depletion device 10 may further incorporate optional spike ports 303 and inlets/outlets 30 and must also be designed to accommodate changes in volume of the inner collapsible blood container 102. Accordingly, special care is taken to incorporate specific design elements and manufacturing methods to ensure the integrity of the impermeable barrier.

Spike ports 303 for use in blood collection kits and systems are commonly known in the art and include products such as Vitalmed #20391 (Vitalmed, Inc., Lakeville, MA) and Qosina 65842 (Qosina Corp., Edgewood, NY). These ports are typically molded from PVC and have a removable cap that provides for a sterile barrier before use, and also provides for some degree of oxygen impermeability to the contents. In some aspects, a spike port 303 is covered by a sealed, frangible section of the outer receptacle film, thereby providing for a sterile barrier and also providing an additional degree of oxygen impermeability. Improved oxygen impermeability is desirable as it increases the shelf life of kits and systems having an oxygen depletion device 10.

As will be appreciated, conventional ports, inlets, and outlets are potential sources of unwanted oxygen ingression that depend both on the selection of the material and the methods used to bond the port, inlet, or outlet to the outer receptacle 101. Methods of bonding materials are well known in the art. As provided herein, inlet/outlet 30 comprises a tube 301 joined to the outer receptacle 101 (or outer receptacle 201) using bond 302 which creates an oxygen impermeable seal to the outer receptacle 101 (or outer receptacle 201). In an aspect, bond 302 is achieved by using constant heat sealing dies heated to and maintained at about 210° F. In an aspect, films are placed between heated dies and clamped together for about to achieve a thermally welded seam. In certain aspects, a heat seal is created in about 5 seconds. In certain aspects, the sealing dies have a grooved section machined out of them to accommodate an intermediary component. In some aspects tube 301 comprises an intermediary component that may be a length of multilayer tubing as discussed below or a small block of machined polymer or molded device. In certain aspects, a molded device is prepared from a polyolefin, such as polyethylene. In aspects according to the present disclosure, the groove is dimensioned about 10% smaller than the features of the component, thereby providing for compression during sealing.

In some aspects, an oxygen impermeable bond is comprised of a section of multilayer tube that is heat sealed into the seam of the outer receptacle 101. In certain aspects, the multilayer tube is comprised of an outer layer of polyethylene, and inner layer of PVC (polyvinyl chloride), and an intermediary layer of EVA (ethyl-vinyl-alcohol) (Pexco, Inc. Athol, MA). In some aspects, additional sections of PVC tubing are solvent bonded into the multilayer tube using, for example, cyclohexanone.

In some aspects, an inlet/outlet 30 is comprised of a tube 301 prepared from a small diamond shaped block of polyethylene with a hole through the center, such that the diamond shaped block is heat sealed into the seam of the outer receptacle to provide an oxygen impermeable bond 302 while the center through-hole provides for fluid connectivity with the contents. In an aspect, a section of PVC tubing is bonded into the center hole of the diamond shaped block using an oxygen impermeable adhesive capable of bonding to polyethylene, such as Loctite 4310, Masterbond X17, or 3M Scothweld 4693, thereby providing for fluid connectivity through the oxygen impermeable outer receptacle to the contents therein. In other aspects, a multilayered tubing can be bonded to the center hole of the diamond shaped block using methods known in the art. In other aspects, a multilayered tubing can be utilized in place of standard PVC intravenous tubing to provide for enhanced oxygen barrier properties.

The users of the collapsible container require convenient filling and removal of the contents, and must be able to empty the contents within 2 minutes per the ISO 3826 standard for blood containers. The outer receptacle can reduce the filling time by constraining the collapsible container and preventing it from expanding. Thus, in some embodiments, the blood storage device is further comprised of an expansion feature to allow for unrestricted filling of the collapsible container. In some embodiments the expansion feature is comprised of a gusseted fold along one or more edges of the outer receptacle. Typically, a fold of about inch is adequate to provide for expansion of the inner container, and the pleats of the fold are sealed into the seams at the ends. In some embodiments, the expansion feature is comprised of a third panel of barrier film sealed along the bottom of the outer receptacle, providing for a three-dimensional bag.

During the development of the oxygen depletion device 10, it was discovered that the size, shape, and number of chambers of an inner collapsible blood container 102 needed to be controlled in order to obtain suitable depletion kinetics. More particularly, even using highly permeable materials, using standard blood bag configurations proved inadequate and had significantly slower reaction kinetics. Not to be limited by theory, it is hypothesized that deoxygenation is a multistep process including release of dissolved oxygen from hemoglobin, diffusion of the dissolved oxygen within the red blood cell cytoplasm, and diffusion of the dissolved oxygen through the red blood cell membrane. Also not to be limited by theory, it is hypothesized that the high concentration of hemoglobin, having very high affinity for oxygen, greatly decreases the diffusion rate of the dissolved oxygen within the cytoplasm. Similarly, the diffusion of dissolved oxygen once it passes through the plasma membrane to the plasma is further limited by absorption and binding to other red cells. Again, not to be limited by theory, it is hypothesized that an additional diffusion barrier for the dissolved oxygen occurs at the gas permeable membrane where it not only needs to pass through the membrane, but also changes state from the dissolved phase to the gaseous phase. Subsequent diffusion and adsorption by the sorbent occurs in a gaseous state and is maximized by incorporating and maintaining a headspace within the outer receptacle 101. Accordingly, it is believed that the diffusion of the gaseous oxygen is maximized by maintaining the concentration gradient within the headspace from the surface of the inner collapsible blood container 102 to the oxygen sorbent 103. Also not to be limited by theory, it is thought that by selecting sorbents that have high absorption kinetics, high binding capacity, and combinations of both, a suitable diffusion gradient for the gaseous oxygen is maintained to drive the rapid kinetics of oxygen depletion in oxygen depletion device 10.

The present disclosure provides for, and includes, an oxygen depletion device 10 for depleting oxygen from blood that comprises an inner collapsible blood container 102 having a surface to volume ratio of between 4.75 centimeters$^2$/milliliter (cm$^2$/ml) and 6.9 cm$^2$/ml enclosed within an outer receptacle 101. In certain aspects, an oxygen depletion device 10 for depleting oxygen from blood comprises an inner collapsible blood container 102 having a surface to volume ratio of between 4.84 cm$^2$/ml and 6.9 cm$^2$/ml enclosed within an outer receptacle 101 when filled with blood for oxygen depletion. In certain aspects, an oxygen depletion device 10 for depleting oxygen from blood comprises an inner collapsible blood container 102 having a surface to volume ratio of between 5.0 cm$^2$/ml and 6.9 cm$^2$/ml enclosed within an outer receptacle 101 when filled with blood for oxygen depletion. In some aspects, an oxygen depletion device 10 for depleting oxygen from blood comprises an inner collapsible blood container 102 having a surface to volume ratio of between 5.0 cm$^2$/ml and 6.5 cm$^2$/ml enclosed within an outer receptacle 101 when filled with blood for oxygen depletion. In some aspects, an oxygen depletion device 10 for depleting oxygen from blood comprises an inner collapsible blood container 102 having a surface to volume ratio of between 5.5 cm$^2$/ml and 6.5 cm$^2$/ml enclosed within an outer receptacle 101 when filled with blood for oxygen depletion.

As used herein, surface to volume and surface area to volume are used interchangeably throughout the present disclosure. A used herein, surface to volume ratios are defined with respect to a standard unit of whole blood, about 1 pint or 450-500 ml. As is evident to a person of skill in the art, collection of less than a unit of blood results in an even higher surface to volume ratio and the oxygen depletion device 10 is suitable for collecting a fraction of a unit of blood without modification. For the collection of more than a unit of blood, the size of the collapsible blood container 102 would need to be adjusted to provide for the desirable rapid kinetics of blood depletion. Modifications of the sort necessary to adapt an oxygen depletion device 10 for the collection of more than a unit of blood is within the level of ordinary skill in the art.

The present disclosure further includes and provides for oxygen depletion device 10 for the collection and depletion of packed red blood cells. A full unit of packed red blood cells in an additive solution comprises about 280±60 ml.

In an aspect according to the present disclosure, the surface to volume ratio of a collapsible blood container 102 is at least 4.84 centimeters$^2$/milliliter (cm$^2$/ml) when filled with blood for oxygen depletion. Not to be limited by theory, it is believed that by increasing the surface to volume ratio, the diffusion limitations imposed by blood itself, particularly by the red blood cells and hemoglobin, can be overcome by decreasing the diffusion distance of the dissolved oxygen within the inner collapsible blood container 102. In an aspect, the surface to volume ratio of a blood container 102 is at least 5.0 cm$^2$/ml when filled with blood for oxygen depletion. In another aspect, the surface to volume ratio of a collapsible blood container 102 is at least 5.5 cm$^2$/ml when filled with blood for oxygen depletion. In a further aspect, the surface to volume ratio of a collapsible blood container 102 is at least 6.0 cm$^2$/ml when filled with blood for oxygen depletion. In some aspects, the surface to volume ratio of a collapsible blood container 102 is at least 6.5 cm$^2$/ml when filled with blood for oxygen depletion.

The present disclosure also includes and provides for increasing the kinetics of deoxygenation of blood by modifying the dimensions of the inner collapsible blood container 102. Not to be limited by theory, the average diffusion distance of a red blood cell in blood minimized as the height is decreased leading to increased deoxygenation kinetics. In certain aspects according the present disclosure, the collapsible blood container 102 is 25.4 cm by 30.5 cm by 0.02 cm before filling with blood, and about 1.5 cm in height after filling with blood. In other aspects according the present disclosure, the collapsible blood container 102 is 17.5 cm by 28.0 cm (7×11 inches) by 0.04 cm before filling with blood, and about 2.0 cm in height after filling with blood. In other aspects according the present disclosure, the collapsible blood container 102 is 25.0 cm by 60.0 (10×23 inches) cm by 0.04 cm before filling with blood, and about 0.3 cm in height after filling with blood.

In certain aspects, the height of a collapsible blood container 102 is no greater than 0.005 cm when empty. In an aspect the height of a collapsible blood container 102 is no greater than 0.1 cm. In certain aspects, the height of a collapsible blood container 102 is between 0.002 and 0.1 cm. When filled with blood, the height of a collapsible blood container 102 is no greater than 0.3 cm. In an aspect the height of a collapsible blood container 102 when filled with blood is no greater than 1.5 cm. In certain aspects, the height of a collapsible blood container 102 when filled with blood is between 0.2 cm and 2.5 cm.

The present disclosure also includes and provides for an oxygen depletion device 10 having dimensions suitable for incorporation of existing blood collection protocols using existing equipment. Design of an oxygen depletion device 10 with recognition to existing technologies reduces capital costs in centralized processing centers and further provides for increased consistency and reliability. As used herein, the dimensions of an oxygen depletion device 10 is primarily limited to the length and width of the outer receptacle 101 where the height of the bag is determined by the requirements of the collapsible blood container 102 to contain about a pint or 450 to 500 ml of whole blood, which is equivalent to a "unit of blood". In another aspect, the dimensions of a collapsible blood container 102 are provided to contain about 220 to 380 ml of packed red blood cells, which is equivalent to a unit of packed red blood cells. The height of an oxygen depletion device 10 is further constrained by the presence of one or more sorbent packets and devices included to maintain an appropriate headspace. In view of these considerations, it become apparent that constraints on the dimension of the outer receptacle 101 of an oxygen depletion device 10 necessarily limits the dimensions of a collapsible blood container 102. Accordingly, a collapsible blood container 102 may be divided into one or more chambers in fluid communication with each other.

In aspects according to the present disclosure, an oxygen depletion device 10 is designed to be incorporated into existing blood agitation equipment. In certain aspects, an oxygen depletion device 10 is dimensioned to efficiently utilize the space available in agitator and mixing tables. In an aspect, an oxygen depletion device 10 is dimensioned to maximally utilize the area available in a platelet agitator, for example a Helmer Labs Platelet Agitator, Model PF96. Suitable dimensions of an oxygen depletion device 10 include those that allow for 1, 2, 4, 6, 8, 10 or more bags to be placed on a flat agitator or mixer surface.

The area of a collapsible blood container 102, within an oxygen depletion device 10 has an area of between about 900 to 1800 cm². Accordingly, an oxygen depletion device 10 that further comprises a spacer 110 effectively doubles the surface area available for gas exchange. In the absence of a spacer 110, the exchange rate of membrane 113 of the collapsible blood container 102 on the lower surface is significantly reduced and the permeable membrane is contacted by the impermeable film.

The present disclosure provides for, and includes, collapsible blood containers 102 further comprising a tie layer 105, for example as illustrated in FIGS. 1A, 1C, 6, 7, 9A, 9B, 10 and 11. As used herein a tie layer 105 comprises an intermediate material that bonds (joins) the membranes 113 (114) together. In certain aspects, the tie layer 105 comprises a solid material having a defined shape. As discussed below, tie layers having a defined shape provide for the incorporation of geometric features 121 including rounded corners and other mixing enhancing shapes. In certain aspects, a tie layer 105 comprises a liquid or gel that can be dried or cured to provide a joining bond between the membranes 113. Accordingly, a collapsible blood container 102 comprising a silicone membrane 113 can be joined by a liquid silicone tie layer 105. In certain aspects, the silicone rubber tie layer 116 can be liquid silicone rubber (LSR).

The present disclosure provides for, and includes, collapsible blood containers 102 further comprising a tie layer 105 prepared from a solid material that has a lower melting point than the membranes 113. By providing a tie layer 105 having a lower melting temperature, the membranes 113 can be heat joined via the tie layer 105 without damaging the structure of the microporous membranes, including melting and/or crystallization. In an aspect, the tie layer 105 is selected to have a melting temperature at least 3° C. below the melting temperature of the microporous membranes 113. In other aspect, the tie layer 105 has a melting temperature at least 10° C. below the melting temperature of the microporous membranes 113. In other aspects, a suitable tie layer 105 is selected to maximize the difference in temperature between the tie layer and the microporous membranes 113 (114) to be joined.

In aspects according to the present disclosure, the tie layer 105 is selected from LDPE and the microporous membrane 113 is selected from the group consisting of polysulfone, hydrophobic polyvinylidene fluoride (PVDF), cellulose ester, mixed esters of cellulose (MCE), polyethersulfone (PES), polypropylene rendered hydrophobic, and polyacrylonitrile. In an aspect, the tie layer 105 is LDPE and the microporous membrane 113 is polysulfone or hydrophobic polyvinylidene fluoride (PVDF). The present disclosure provides for and includes the selection of suitable microporous membranes and further includes multilayer membranes 113.

The present disclosure provides for and includes, construction of collapsible blood containers 102 having a tie layer wherein the tie layer extends beyond the seal indicated as gap 109, for example as illustrated in FIG. 9B.

The present disclosure provides for and includes a gap 109 of space between where the seal ends and the tie layer ends. In certain aspects, gap 109 is between 0.05 and 2.5 cm. In other aspects, gap 109 is at least 0.1 cm wide. In other aspects, gap 109 is at least 0.5 cm wide. In other aspects, gap 109 is at least 1 cm wide. In other aspects, gap 109 is at least 1.5 cm wide. In some aspects, gap 109 is between 0.5 and 1.5 cm wide. In other aspects, gap 109 is at least 2 cm wide. In other aspects, gap 109 is between 2 and 2.5 cm wide. In other aspects, gap 109 is at least 2.5 cm wide.

As shown in FIG. 9B, seals 107 are laminated to the membranes 113 and are in turn laminated to each other as seal 108. As illustrated in FIG. 7, the lamination of the tie layer 105 can be accomplished in two steps, first to the separate membranes 113, then a second step to join the prelaminated membranes 113 together. In the alternative, the lamination steps can be combined into a single step wherein a single tie layer 105 is used to join membranes together.

As shown in FIG. 9B, seal 107 may extend beyond the width of seal 108. By extending seal 107 beyond the width of seal 108, seal 107 provides for strengthening of flexure point 115, as indicated in FIG. 9A. Without being limited to a specific mechanism, it is believed that the tie layer 105 acts as a reinforcing strain relief inboard of the seal and allows for flexure of the bag at the seal as it is filled and drained of blood product.

The present disclosure provides for, and includes, collapsible blood containers 102 having geometric features that improve the mixing of blood during the deoxygenation process. The improved geometries of the present disclosure further include geometries to enhance the filling and draining of the collapsible blood containers 102. Improved geometries reduce or eliminate 'dead' spots in the bag. Not to be limited by theory, dead spot arise in the corners of bags with square geometries. Prior to the present disclosure, methods and blood depletion devices were not time limited and the gas exchange methods typically employed resulted in sufficient mixing. Accordingly, the deficiencies of earlier designs were not revealed.

In aspects according to the present disclosure, a collapsible blood containers 102 includes one or more geometric features 121. In an aspect, the geometric features comprise rounded corners in the collapsible blood container 102 and provide for the elimination of 'dead' spots during mixing. The present disclosure provides for the geometric features 121 to be incorporated directly into a tie layer 105. In other aspects, the geometric features 121 can be incorporated into the collapsible blood container 102 using an external die or plate. In other aspects the geometric features of the collapsible blood container 102 can be provided by a suitable mold having the shape of the geometric feature 121. In certain aspects, the geometric feature 121 provides a round or oval shape to a collapsible blood container 102, for example as shown in FIG. 10.

In certain aspects, the geometric feature 121 can be an ellipse with a first radius from about 0.1 cm to about 7.6 cm and a second radius from about 1 cm to about 7.6 cm. In an aspect, the geometric feature 121 can be an ellipse with a first radius of about 2.5 cm and a second radius of about 5 cm. In an aspect, the geometric feature 121 can be an ellipse with a first radius of about 5 cm and a second radius of about 7.6 cm. In an aspect the geometric feature 121 can be a circle with a diameter of about 5 cm. In an aspect the geometric feature 121 can be a circle with a diameter of about 7.6 cm.

As is evident, an oxygen depletion device 10 having a defined size necessarily constrains the dimensions of a collapsible blood container 102 according to the present disclosure. In certain aspects, a collapsible blood container 102 is further limited by a specified surface to volume ratio. In accordance with these limitations, the present disclosure provides for, and includes, a collapsible blood container 102 having two or more chambers in fluid communication with each other.

The oxygen depletion container device can be constructed in such a manner that allows for the blood volume to area of bag to be optimized against the overall size of the oxygen depletion container device, while exposing more of the blood volume to the material with oxygen permeability in the utilized space. The blood volume can be contained in a collapsible blood container 102 having two or more chambers that allow for their specific arrangement within the outer receptacle 101. In certain aspects, the oxygen depletion device 10 height, when placed onto a surface, does not occupy impractical space in the intended mixing apparatus. The chambers can be arranged side to side, stacked on top of one another, partially stacked onto each other, staggered in a row, or saddled on top of each other onto one or more stacking heights. Sorbent 103 can be positioned over or between chambers as needed. Chambers may be filled and drained individually or in unison when such chambers are connected via tubing or fluid conduits that allow for easy filling and draining. It would be understood that the arrangement and interconnection of collapsible blood containers 102 having two or more chambers can be performed by a person of skill in the art.

In certain aspects, a collapsible blood container 102 comprises two or more chambers. In an aspect, a collapsible blood container 102 can have two chambers placed side by side or end to end depending on the dimensions. In another aspect, a collapsible blood container 102 can have three chambers placed side by side or end to end depending on the dimensions. In yet another aspect, a collapsible blood container 102 can have three chambers placed side by side or end to end depending on the dimensions. A person of ordinary skill could prepare additional configurations of a collapsible blood container 102 having multiple chambers placed in adjacent positions and orientations to maximize the utilization of space.

In other aspects provided for and included in the present disclosure, a collapsible blood container 102 may comprise two or more chambers that are stacked. When in a stacked configuration, to maintain optimal gas diffusion rates, spacers 110 or meshes 110 are included to ensure the separation of adjacent chambers. In certain aspects, the space between a stacked chamber further includes one or more sorbent sachets in order to maintain optimal gas diffusion rates. In certain aspects, two chambers may be stacked. In another aspect, three chambers may be stacked. In yet another aspect, four chambers may be stacked.

The present disclosure provides for, and includes, a collapsible blood container 102 comprising a combination of stacked and adjacent chambers. As provided herein, the number and stacking of chambers of a collapsible blood container 102 further comprises a surface to volume ratio of the combined chambers of at least 0.4 cm²/ml. Additional variations consistent with the present disclosure can be prepared by one of ordinary skill in the art.

The present disclosure provides for, and includes, an oxygen depletion device 10 for depleting oxygen from blood comprising an outer receptacle 101 substantially impermeable to oxygen, inner collapsible blood container 102 that is permeable to oxygen and an oxygen sorbent situated within said outer receptacle wherein the collapsible blood container 102 further comprises one or more mixing structures 119 that increase mixing of the blood during oxygen depletion. In certain aspects, the mixing structures 119 are incorporated into the structure of the collapsible blood container 102. In other aspects, the mixing structures 119 are added to the inside of, but not physically joined to the collapsible blood container 102. In yet other aspects, a mixing structure 119 is a structure outside of the collapsible blood container 102 that restricts or modifies the shape of the container 102 to decrease or disrupt laminar flow. Mixing structures 119 according to the present disclosure are designed to increase blood movement in the collapsible blood container 102, increase turbulent flow within the collapsible blood container 102, or combinations of both. Importantly, mixing structures and mixing should not significantly increase lysis, or damage to, the red blood cells.

Figure 10A:
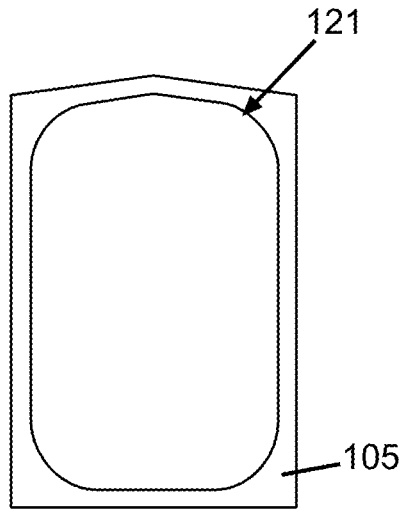
Figure 10A:
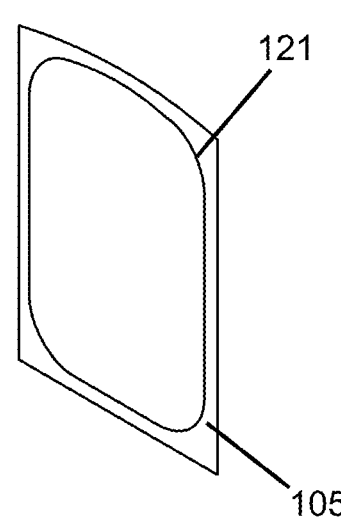
Figure 10B:
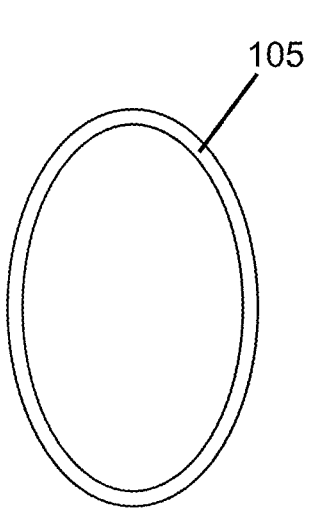
Figure 10B:
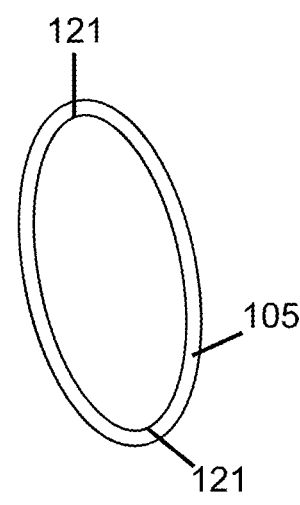
Figure 10C:
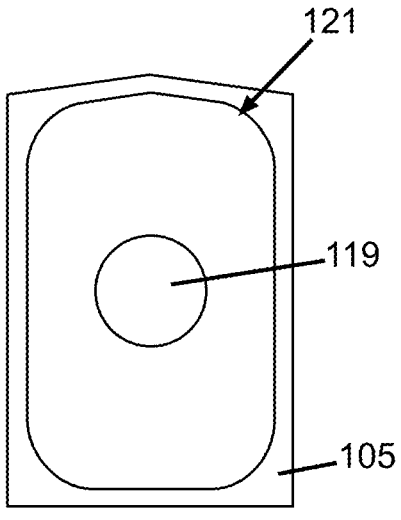
Figure 10C:
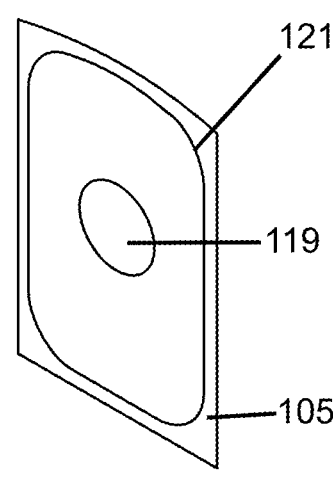
Figure 10D:
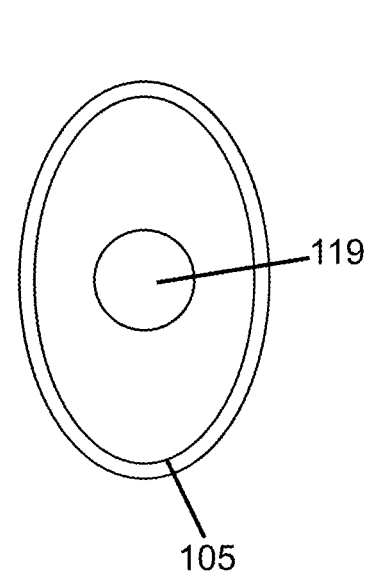
Figure 10D:
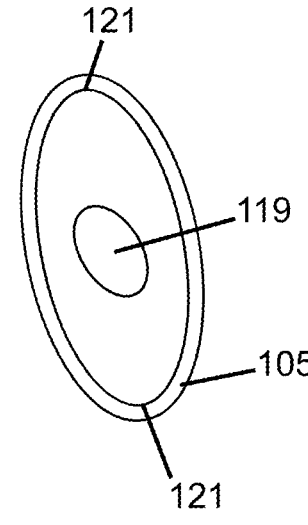

In aspects according to the present disclosure, a mixing structure 119 is included in the structure of membrane 113. In certain aspects, a mixing structure 119 in membrane 113 comprises ridges, bumps, or protrusions on the inside of the collapsible blood container 102 and are in contact with the blood. In an aspect, a mixing structure 119 in membrane 113 comprises one or more ridges. In an aspect, a mixing structure 119 comprises joining the upper and lower membranes 113 (114) together, for example as illustrated in FIGS. 10C and 10D. In an aspect, the one or more ridges extend across the full width or length of the inner surface of collapsible blood container 102. In other aspects, the ridges alternate and may be staggered. In certain aspects, the mixing structure 119 in membrane 113 comprises bumps or other protrusions designed to disrupt laminar flow and induce turbulence. Similarly, in certain aspects, the mixing structure 119 in membrane 113 comprises depressions designed to disrupt laminar flow and induce turbulence. In certain aspects, the mixing structures 119 are baffles incorporated into membrane 113. Baffles are flow directing vanes or panels. In some aspects, a mixing structure 119 comprising one or more baffles may be incorporated into a second membrane 114.

In certain aspects, a mixing structure 119 is contained within the collapsible blood container 102. In an aspect, a mixing structure 119 within the collapsible blood container 102 comprises one or more beads or balls that aid in mixing when the collapsible blood container 102 is agitated. In another aspect, a mixing structure 119 within the collapsible blood container 102 comprises one or more strings or elongated structures that aid in mixing when the collapsible blood container 102 is agitated. In yet another aspect, a mixing structure 119 within the collapsible blood container 102 comprises a mesh that aids in mixing when the collapsible blood container 102 is agitated.

The present disclosure provides for, and includes, an oxygen depletion device 10 having an outer receptacle 101 that is substantially impermeable to oxygen enclosing an inner collapsible blood container 102 and providing a headspace. In an aspect, the oxygen sorbent 103 is disposed within the headspace thereby creating an oxygen depleted state within the headspace. In an aspect, said oxygen sorbent 103 disposed in the headspace further maintains the headspace in an oxygen depleted state by removing oxygen that may enter through the outer receptacle 101 or through the one or more inlets/outlets 30.

Maintaining the headspace in an oxygen depleted state provides for improved shelf life for oxygen depletion device 10. In an aspect, an assembled oxygen depletion device 10 has a shelf life of at least 24 months. In another aspect, the oxygen depletion device 10 has a shelf life of at least 12 months after assembly of the components. In an aspect according to the present disclosure, the assembled oxygen depletion device 10 meets ISTA-2A standards.

In certain aspects of the present disclosure, the headspace provides for improved processing times. For oxygen depletion device 10, removing ambient air present or inert flushing gas from the assembly prior to sealing the outer receptacle 101 reduces the volume of the headspace. Applying a vacuum to the outer receptacle 101 prior to sealing reduces the volume of the headspace and decreases the total volume of the assembled oxygen depletion device. While reduced overall headspace volume provides for reduced shipping volume, it can result in increased filling times by constraining the collapsible blood container 102. In certain aspects, the headspace may be flushed with nitrogen gas and then sealed under slightly less than ambient pressure to provide a reduced headspace volume in the oxygen depletion device 10 without significantly increasing the fill and process time.

In certain aspects, the headspace may be initially depleted of oxygen by flushing the headspace with nitrogen. In an aspect, the headspace of oxygen depletion device 10 is flushed with nitrogen gas prior to sealing the outer receptacle 101. In an aspect, the flushing gas is ≥99.9% nitrogen gas.

The present disclosure includes and provides for oxygen depletion device 10 having inner collapsible blood container 102 divided into two or more compartments. In certain aspects, an oxygen depletion device 10, having a collapsible blood container 102 divided into multiple compartments has a headspace of between 10 and 500 ml per compartment. In an aspect the headspace is between 20 and 400 ml per compartment. In another aspect the headspace volume is between 60 and 300 ml per compartment. In a further aspect, the headspace volume is between 100 and 200 ml per compartment of a collapsible blood container. In an aspect, an oxygen depletion device 10 having inner collapsible blood container 102 divided into compartments has a headspace of about 10 ml per compartment. In another aspect, the headspace is about 100 ml to about 200 ml per compartment. In another aspect the headspace is about 300 ml to about 500 ml per compartment.

The present disclosure includes and provides for oxygen depletion device 10 having inner collapsible blood container 102 divided into two or more compartments. In certain aspects, an oxygen depletion device 10, having a collapsible blood container 102 divided into two compartments has a headspace of between 20 and 1000 ml. In an aspect the headspace is between 100 and 800 ml. In another aspect the headspace volume is between 200 and 700 ml. In a further aspect, the headspace volume is between 300 and 500 ml for a two compartment collapsible blood container. In an aspect, an oxygen depletion device 10 having inner collapsible blood container 102 divided into two compartments has a headspace of about 700 ml. In another aspect, the headspace is about 200 ml to about 700 ml. In another aspect the headspace is about 300 ml to about 500 ml.

The present disclosure includes and provides for oxygen depletion device 10 having inner collapsible blood container 102 divided into two or more compartments. In certain aspects, an oxygen depletion device 10, having a collapsible blood container 102 divided into three compartments has a headspace of between 20 and 1000 ml. In an aspect the headspace is between 100 and 800 ml. In another aspect the headspace volume is between 200 and 700 ml. In a further aspect, the headspace volume is between 400 and 600 ml for a three compartment collapsible blood container. In an aspect, an oxygen depletion device 10 having inner collapsible blood container 102 divided into three compartments has a headspace of about 800 ml. In another aspect, the headspace is about 200 ml to about 700 ml. In another aspect the headspace is about 400 ml to about 600 ml. In an aspect the headspace is about 7000 ml due to full expansion of the headspace area. In another aspect the headspace is between 700 and 7000 ml. In another aspect the headspace is between 800 and 6000 ml. In another aspect the headspace is between 1000 and 5000 ml. In another aspect the headspace is between 2000 and 4000 ml.

The present disclosure includes and provides for an oxygen depletion device 10 having an inner collapsible blood container 102 and further including one or more spacers 110 that ensure the separation of the outer receptacle 101 and the inner collapsible blood container 102. The spacer 110 provides for the maintenance of the headspace in the oxygen depletion device to ensure efficient diffusion of the oxygen from the surface of membrane 113 to the sorbent 103. A spacer 110 can be prepared from one or more of the materials selected from the group consisting of a mesh, a molded mat, a woven mat, a non-woven mat, a strand veil, and a strand mat. In certain aspects, the spacer 110 can be integrated directly into the collapsible blood container 102 as ribs, dimples, or other raised feature that maintains a separation between the outer receptacle 101 and the inner collapsible blood container 102. The present specification also includes and provides for a spacer 110 to be integrated into the outer receptacle 101 as ribs, dimples, or other suitable raised feature capable of maintaining a separation between the outer receptacle 101 and the inner collapsible blood container 102. Mixing is an important aspect of the present disclosure. In one aspect of the present disclosure, spacer 110 is selected to be flexible so as to not interfere with the flow of the blood product.

The present disclosure includes, and provides for, a spacer 110 having open areas, for the free diffusion of gas from the surface of the permeable membranes 113 and 114. In an aspect, the spacer 110 is provided as a mesh 110 having open spaces 111. As used herein, the open area 111 is also referred to as the interstice 111. As provided herein, the interstice 111 may be provided by a regular weave of a mesh 110, such that the interstice 111 is regular and repeating within the spacer 110. In other aspects, the interstice 111 may comprise an irregular open area, for example as provided by a spacer 110 constructed from a non-woven mesh. In an aspect, the interstice 111 has an area of between about 0.5 milimeters$^2$ (mm$^2$) and about 100 mm$^2$. In a further aspect, the interstice 111 has an area of between 1 mm$^2$ and 10 mm$^2$. In other aspects the interstice 111 has an opening that is greater than 0.75 mm$^2$ per opening. In an aspect the open area or interstitial space of a mesh comprise between 30% to 90% of the total area of a spacer 110. In an aspect the open area or interstitial space of a mesh comprise between 50% to 80% of the total area of a spacer 110. In a further aspect, the open area comprises about 60%. In other aspects, the open area comprises up to 75% of the total area.

The present disclosure provides for, and includes, inner collapsible blood containers 102 having a spacer 110 incorporated into the membrane 113, the membrane 114, or both. In aspects according to the present disclosure, the spacer 110 provides for both the separation of the outer receptacle 101 and the inner collapsible blood container 102 but also for the reinforcement of the permeable membranes. In aspects according to the present disclosure, the spacer 110 prevents tearing, puncturing and bursting of the inner collapsible blood container 102 when filled with blood and used in the depletion methods of the present disclosure. In some aspects, the spacer 110 is provided as a mesh 110 that is integrated into a silicone membrane during the manufacturing process. In other aspects, the spacer 110 is applied to, and joined to, a finished silicone membrane. In other aspects, the spacer 110 is provided as an integrated mesh of a porous membrane.

In an aspect, a membrane 113 or 114 having an integrated spacer 110 is prepared from a suspension of liquid silicone rubber (LSR). In an aspect, the LSR is suspended in xylene, hexane, tert butyl acetate, heptane, acetone, or naptha. In aspects according to the present disclosure, the suspension comprises 10 to 30% LSR. As provided herein, a membrane 113 or 114 having an integrated spacer 110 is prepared by providing a 20 to 750 μm layer of an LSR suspension, partially curing the LSR layer and applying a spacer 110 as provided in the present disclosure and performing a second curing step to provide a cured 10 to 100 μm thick silicone membrane 113 having an integrated spacer 110.

The present disclosure also includes and provides for a mesh 110 comprising co-extruded fibers having an inner material 117 and binding material 118. In aspects according to the present disclosure, binding material 118 is integrated into the pores of membrane 113 (114) during application of the mesh 110 to the membrane. In an aspect, the binding material 118 is integrated into the pores of a porous membrane 113 by heating. In aspects according to the present disclosure, binding material 118 may be selected from the group consisting of ethylvinyl alcohol (EVOH), ethylvinylacetate (EVA), or acrylate. In aspects according to the present disclosure co-extruded fibers having an inner material 117 and binding material 118 are meshes 110 that include the DuPont Bynel® series of modified ethyl vinyl acetates and modified ethyl vinyl acrylates.

The present disclosure also includes and provides for inner collapsible blood containers 102 that further comprise a window 112. As used herein, a window 112 is made of a transparent material and is bonded or otherwise incorporated into the inner collapsible blood container 102. In accordance with the present disclosure, suitable materials for window 112 are blood compatible. In certain aspects, materials suitable for a window 112 are oxygen impermeable. In other aspects, materials suitable for a window 112 are oxygen impermeable. The size of a window 112 need only be large enough to provide observation of the blood.

Also included and provided for by the present disclosure are collapsible blood containers having bis(2-ethylhexyl) phthalate (DEHP). DEHP is included in most PVC based blood storage bags as a plasticizer where it has been observed that DEHP provides a protective effect to stored red blood cells. See U.S. Pat. No. 4,386,069 issued to Estep. In certain aspects, an oxygen depletion device 10 may further include DEHP incorporated in the inner collapsible blood container 102. In other aspects, DEHP may be provided separately within the inner collapsible blood container 102.

The present disclosure provides for, and includes, an oxygen depletion device 10 that does not include DEHP. It has been hypothesized that DEHP may act as an endocrine disruptor and certain regulatory agencies are considering ordering the removal of DEHP from blood bags. It has been observed that DEHP may not be necessary when red blood cells are stored anaerobically. See International Patent Publication No. WO 2014/134503, hereby incorporated by reference in its entirety. Accordingly, in certain aspects, oxygen depletion device 10 entirely excludes DEHP from all blood contacting surfaces. In other aspects, oxygen depletion device 10 limits DEHP containing surfaces to tubing, ports, and inlets such as those illustrated in the Figures at, for example, 106 and 205. In an aspect, oxygen depletion device 10 excludes a DEHP containing collapsible blood container 102.

The present disclosure provides for, and includes, an oxygen depletion device 10 having an oxygen indicator 104. Similarly, the present disclosure provides for, and includes, blood storage device 20 having an oxygen indicator 206. In an aspect, the oxygen indicator 206 detects oxygen and indicates that the oxygen depletion device 10 has been compromised and is no longer suitable for its intended purpose. In an aspect, the oxygen indicator 206 provides a visual indication of the presence of oxygen. In certain aspects, the oxygen indicator 206 provides an indication of the amount of oxygen.

In an aspect according to the present disclosure, the outer receptacle may contain an oxygen indicator to notify the user if the oxygen sorbent is no longer active for any reason, such as age, or if the outer receptacle has been compromised, allowing excess oxygen to ingress from ambient air. Such oxygen indicators are readily available and are based on a methylene blue indicator dye that turns blue in the presence of oxygen of about 0.5% or more and pink when the oxygen level is below about 0.1%. Examples of these oxygen indicators are the Tell-Tab oxygen indicating tablet from Sorbent Systems, Inc. (Impak Corp., Los Angeles, CA), and the Oxygen Indicator tablet from Mitsubishi Gas Chemical America (MGCA, NY, NY).

The present disclosure provides for, and includes, methods for preparing blood for storage under oxygen depleted conditions comprising providing blood having red blood cells having oxygen to be removed to an oxygen depletion device 10, incubating the blood for a period of time, and transferring the deoxygenated blood to an anaerobic storage bag. In aspects according to the present disclosure, the method further includes agitating the oxygen depletion device 10 to provide for mixing of the blood for deoxygenation. In other aspects, due to the configuration of the oxygen depletion device 10, agitating is not necessary.

For safety, the collection and processing of blood is regulated by a national or regional governmental agency. In the U.S., the Food and Drug Administration (FDA) has established guidelines for the proper handling of blood and blood products. Similarly in Europe, the European Union has been granted regulatory authority that is binding for member states, and typically follows guidelines provided by the Council of Europe. The key requirements for blood establishments and for hospital blood banks in the United Kingdom (UK), for example, are defined in the Blood Safety and Quality Regulations (Statutory Instrument 2005 No. 50) and are enforced by the Medicines and Healthcare products Regulatory Agency, whose powers are derived from UK legislation, to maintain the safety and quality of blood and blood products for transfusion within the UK.

Generally, the guidelines established by the various authorities fall in to two main groups. In the first group, as exemplified by the U.S., the allowable time period from donor collection to processing for platelets, and thus driving the storage of RBC's at 2 to 6° C., is 8 hours. That is, the various processing steps, currently including plasma separation and collection, leukoreduction, platelet separation and collection and packed red blood cell preparation, need to be completed, and various components stored within 8 hours in order to preserve the viability of the platelets (see Moroff & Holme, "*Concepts about current conditions for the prepa-*

*ration and storage of platelets" in Transfus Med Rev* 1991; 5:48-59). In Europe, the period available for processing is 24 hours. Accordingly the methods and processes provided in the present disclosure are designed to achieve the beneficial, and storage lesion reducing, level of deoxygenation for blood storage within about 8 hours from venipuncture.

In accordance with the methods of the present disclosure, blood may be obtained from a donor and processed to less than 20% oxygen saturation within 12 hours of collection. Beginning the depletion process, at or soon after collection, improves the efficiency of the process by leveraging the increases in reaction rates due to the higher temperatures. In an aspect, the blood is collected from a donor at about 37° C. and collected in an oxygen depletion device 10 having a suitable amount of anticoagulant. In addition to the increased temperature, the whole blood is typically about 35-65% oxygen saturated when collected by venipuncture from a patient. In one aspect of the present disclosure the whole blood is 35-65% oxygen saturated when collected by venipuncture from a patient. In another aspect the whole blood is 40-60% oxygen saturated when collected by venipuncture from a patient. In another aspect the whole blood is 45-55% oxygen saturated when collected by venipuncture from a patient. In another aspect the whole blood is 50-65% oxygen saturated when collected by venipuncture from a patient. Conventional methods do not provide collection kits and bags that prevent the ingress of oxygen. Thus delays in beginning the oxygen reduction process can greatly increase the time necessary to prepare oxygen-reduced blood having less than 20% oxygen saturation.

The methods and devices of the present disclosure further provide for the preparation of oxygen-reduced blood having less than 10% oxygen saturation. In an aspect, the 10% level is achieved within 8 hours or less of collection from a donor. In other aspects, the blood is reduced to less than 10% oxygen saturation in 6 hours or less. In yet other aspects, the blood is reduced to less than 10% oxygen saturation in 4 hours or less.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells (LRpRBC), and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 2° C. and 6° C.

As used herein, the term "whole blood" refers to a suspension of blood cells that contains red blood cells (RBCs), white blood cells (WBCs), platelets suspended in plasma, and includes electrolytes, hormones, vitamins, antibodies, etc. In whole blood, white blood cells are normally present in the range between 4.5 and $11.0 \times 10^9$ cells/L and the normal RBC range at sea level is $4.6\text{-}6.2 \times 10^{12}$/L for men and $4.2\text{-}5.4 \times 10^{12}$/L for women. The normal hematocrit, or percent packed cell volume, is about 40-54% for men and about 38-47% for women. The platelet count is normally $150\text{-}450 \times 10^9$/L for both men and women. Whole blood is collected from a blood donor, and is usually combined with an anticoagulant. Whole blood, when collected is initially at about 37° C. and rapidly cools to about 30° C. during and shortly after collection, but slowly cools to ambient temperature over about 6 hours. Whole blood may be processed according to methods of the present disclosure at collection, beginning at 30-37° C., or at room temperature (typically about 25° C.). As used herein, a "unit" of blood is about 450-500 ml including anticoagulant.

As used herein, a "blood donor" refers to a healthy individual from whom whole blood is collected, usually by phlebotomy or venipuncture, where the donated blood is processed and held in a blood bank for later use to be ultimately used by a recipient different from the donor. A blood donor may be a subject scheduled for surgery or other treatment that may donate blood for themselves in a process known as autologous blood donation. Alternatively and most commonly, blood is donated for use by another in a process known as heterologous transfusion. The collection of a whole blood sample drawn from a donor, or in the case of an autologous transfusion from a patient, may be accomplished by techniques known in the art, such as through donation or apheresis. Whole blood obtained from a donor using venipuncture has an oxygen saturation ranging from about 30% to about 70% saturated oxygen ($sO_2$).

As used herein, "red blood cells" (RBCs) includes RBCs present in whole blood, leukoreduced RBCs, platelet reduced RBCs, and leukocyte and platelet reduced RBCs. Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 50%.

Platelets are small cellular components of blood that facilitate the clotting process by sticking to the lining of the blood vessels, and also facilitate healing by releasing growth factors when activated. The platelets, like the red blood cells, are made by the bone marrow and survive in the circulatory system for 9 to 10 days before they are removed by the spleen. Platelets are typically prepared using a centrifuge to separate the platelets from the buffy coat sandwiched between the plasma layer and the pellet of red cells.

Plasma is a protein-salt solution and the liquid portion of the blood in which red and white blood cells and platelets are suspended. Plasma is 90% water and constitutes about 55 percent of the blood volume. One of the primary functions of plasma is to assist in blood clotting and immunity. Plasma is obtained by separating the liquid portion of the blood from the cells. Typically, plasma is separated from the cells by centrifugation. Centrifugation is the process used to separate the components of the whole blood into the plasma, the white blood cells, the platelets and the packed red blood cells. During centrifugation, the plasma will initially migrate to the top of a vessel during a light spin. The plasma is then removed from the vessel. The white blood cells and platelets are removed during a second centrifugation cycle to produce the packed red blood cells.

The present disclosure includes and provides for methods for preparing oxygen depleted blood for storage. An oxygen reduced blood or blood component suitable for storage and benefiting from the reduced damage from storage lesions, reduced toxicity, and importantly reduced morbidity, is a blood or blood component having an oxygen saturation of less than about 20%. In certain aspects, the oxygen levels in the blood or blood component are reduced to a level of less than 15%. In other aspects, the oxygen saturation of the blood is reduced to 10% or less prior to storage. In yet another aspect, the oxygen saturation of the blood is reduced to less than 5% or less than 3% prior to storage.

According to methods of the present disclosure, the blood or blood component is depleted of oxygen and placed into storage within 4 to 24 hours of collection. In other aspects, the methods provide for the depletion of oxygen and placement into storage within 8 hours of collection. In other aspects, the blood or blood component is depleted of oxygen and placed into storage in less than 6 hours of collection. In yet another aspect, the blood is depleted of oxygen and placed into storage in less than 4 hours of collection.

The present disclosure provides for, and includes, methods for preparing blood for storage under oxygen depleted conditions comprising providing blood having red blood cells having oxygen to be removed to an oxygen depletion device 10, and incubating the blood for a period of time. In certain aspects, the blood is mixed through agitation. In other aspects, the oxygen depletion device provides for sufficient deoxygenation with little or no mixing.

As would be understood, blood for depletion may start with varying levels of oxygen saturation. In certain aspects, the blood is whole blood collected at about 70% saturation and between about 40% to 45% hematocrit. The methods of the present disclosure also provide for the rapid deoxygenation of LRpRBCs that typically have a hematocrit of about 50% and saturation levels of up to 90% or higher.

The devices and methods of the present disclosure are intended to provide oxygen depleted blood for storage within 24 hours or less. In certain aspects, the oxygen is removed using an oxygen depletion device 10 by incubation for a time period with agitation. In other aspects, the oxygen is removed using an oxygen depletion device 10 using methods in which the depletion device is not agitated or otherwise mixed during the incubation period. As would be understood by one of skill in the art, inclusion of an agitation or mixing step in the process allows for an oxygen depletion device 10 to have lower surface to volume ratios. Agitation can also reduce the permeability necessary to achieve a desired level of deoxygenation. To achieve the most rapid depletion kinetics, a combination of an oxygen depletion device 10 having high permeability and a high surface to volume ratio is combined with agitation during the depletion period. Depending on the application and the processing protocols employed, the time necessary to complete processing can vary to between 4 and 24 hours. Thus, the devices and methods of the present disclosure can be incorporated into the protocols of existing blood processing centers and comply with applicable regional regulations by adjusting the devices and methods as provided in the present disclosure.

In aspects according to the present disclosure, to reduce the processing time to achieve a blood saturation of less than 20%, the blood can be agitated or mixed during the depletion period. In most aspects, the blood is agitated or mixed for less than 24 hours. As mixing and agitation of the blood during processing can lead to lysis and degradation, the depletion time period with agitation should be minimized.

In certain aspects, the blood is incubated with agitation for less than 12 hours. In other aspects, the incubation and agitation time is less than 8 hours. Also provided for are methods for reducing oxygen to less than 20% using an oxygen depletion device 10 and incubating with agitation for less than 6 hours or less than 4 hours. In yet other aspects, the incubation time with agitation is 3.5 hours or 3.0 hours. In certain aspects, the blood can be reduced to 20% or less with a 4-hour incubation with agitation in an oxygen depletion device 10. In yet further aspects, the method provides for incubation times of 0.5 or 1.0 hour. In other aspects, blood is incubated for 1.5 hours or 2.0 hours in an oxygen depletion device 10.

It is well understood that reaction rates are temperature dependent, with higher temperatures increasing the reaction rate. The rate constant k varies exponentially with temperature where $k=Ae^{-Ea/RT}$ (the Arrhenius equation). Notably, the dependence on temperature is independent of the concentration of reactants and does not depend on whether the order of the rate is constant (e.g., first order vs. second order). Typically, a 10° C. increase in temperature can result in a two fold increase in reaction rate. Accordingly, a person of skill in the art would recognize that the release of oxygen from hemoglobin as well as the other steps of the deoxygenation process is temperature dependent. Importantly, once the temperature of the blood is lowered to the standard storage temperature of between 2° C. and 6° C., the rate of deoxygenation is significantly reduced. Even further, under current approved protocols for the collection, processing and storage of blood for transfusion purpose conditions, the stored blood is not mixed which further reduces the rate at which oxygen can be removed. Accordingly, the methods and devices of the present disclosure are designed to remove most of the oxygen prior to storage and within the time periods established by the appropriate regulatory agencies. As provided herein, the depletion of oxygen is intended to begin as soon after collection from the donor as possible, and is intended to be largely completed prior to cooling the blood for storage.

As provided herein, the methods can be performed using recently collected blood that is about 37° C., when it is collected from the donor. In other aspects, the blood may be processed prior to depletion, including removing leukocytes, plasma, and platelets. In the alternative, the blood may be further processed after oxygen reduction.

The present disclosure provides for, and includes, processing blood that has cooled from body temperature to ambient temperature, typically about 25° C. Using the methods and devices disclosed here, oxygen reduced blood having less than 20% oxygen saturation can be prepared at ambient temperatures (e.g., about 25° C.). The ability to reduce the oxygen to desired and beneficial levels at ambient temperatures allows for the systems and methods to be incorporated into existing blood collection protocols and blood collection centers.

The present disclosure provides for, and includes, methods for preparing blood for storage under oxygen depleted conditions comprising providing blood having red blood cells having oxygen to be removed to an oxygen depletion device 10, incubating the blood for a period of time and further comprising agitating or mixing during the incubation period. As used herein, the terms "agitating" or "mixing" are used interchangeably and include various mixing methods, including but not limited to rocking, nutating, rotating, stirring, massaging, swinging, linearly-oscillating and compressing the oxygen depletion device.

In a method according to the present disclosure, the incubation period with agitation can be as short as 30 minutes and up to 24 hours. In certain aspects, the method includes an incubation period of between 1 and 3 hours with agitation in an oxygen depletion device 10. In other aspects, the incubation period is between 1 and 4 hours or 1 and 6 hours. In other aspects, the incubation period is about 2 hours or about 4 hours.

In an aspect according to the present disclosure, a method of reducing the oxygen from red blood cells includes placing the red blood cells in a device according to the present disclosure and placing the device on an agitator to enhance the oxygen removal from the red blood cells through a mixing action. The use of agitators in the practice of blood transfusion is well known with respect to preventing clot formation, such as in the use of rocker tables and donation scale mixers, which provide for a gentle rocking motion of about 7 degrees tilt and 1 to about 15 oscillations per minute. Similar devices, already available in oxygen depletion centers and familiar to staff, can be used to ensure proper mixing.

To maximize the kinetics of the oxygen depletion process, both physical and methodological approaches can be applied. As discussed above, physical approaches to reducing the resistance to diffusion of the inner blood compatible bag is achieved by selecting materials with high permeability and by reducing the thickness of the material to decrease the Barrer value. For microporous materials, apparent Barrer values can be decreased by decreasing the size of the micropores and by increasing the number of micropores. It is understood that the size of micropores are necessarily limited by the necessity to prevent the perfusion of water through the barrier which occurs in certain microporous materials at about 1 µm. Also as provided above, the surface to volume ratio is selected to reduce the diffusion distance of the dissolved oxygen as it makes its way to the permeable surface. These limitations and requirements of the materials and design to achieve effective and rapid reduction of oxygen in blood are discussed above.

In addition to minimizing the diffusion barriers and the diffusion distance through design and by appropriate selection of materials, the effective diffusion distance can be further reduced by appropriate mixing. As would be understood, complete and efficient mixing effectively eliminates the effect of diffusion distance on the blood reduction process as oxygen containing red blood cells enter the oxygen free environment in close proximity to the permeable membrane. Similarly, the diffusion distance would also be eliminated by spreading the blood into an impracticably thin volume. The present disclosure provides methods and devices that optimize the devices and methods to achieve high rates of depletion.

The present disclosure provides for, and includes, methods of mixing blood in an oxygen depletion device 10 that achieves rapid rates of deoxygenation and rate constant of between about $0.5 \times 10^{-2}$ min$^{-1}$ and about $5.0 \times 10^{-2}$ min$^{-1}$. In aspects according to the present disclosure, the rate constant is at least $-1.28 \times 10^{-2}$ min$^{-1}$. In other aspects, deoxygenation occurs at rate having a rate constant of at least $-0.5 \times 10^{-2}$. In another aspect, deoxygenation occurs at rate having a rate constant of at least $-0.9 \times 10^{-2}$. In another aspect, deoxygenation occurs at rate having a rate constant of at least $-1.0 \times 10^{-2}$. In another aspect, deoxygenation occurs at rate having a rate constant of at least $-1.5 \times 10^{-2}$. In further aspects, deoxygenation occurs at rate having a rate constant between $-1.0 \times 10^{-2}$ min$^{-1}$ and $-3.0 \times 10^{-2}$ min$^{-1}$. In further aspects, deoxygenation occurs at rate having a rate constant between $-1.0 \times 10^{-2}$ min$^{-1}$ and $-2.0 \times 10^{-2}$ min$^{-1}$. In further aspects, deoxygenation occurs at rate having a rate constant between $-1.0 \times 10^{-2}$ min$^{-1}$ and $-4.0 \times 10^{-2}$ min$^{-1}$.

In an aspect according to the present disclosure, proper mixing is achieved in an oxygen depletion device 10 having a surface to volume ratio of at least 5.0 cm$^2$/ml. Not to be limited by theory, it is hypothesized that at lower surface to volume ratios, the collapsible blood container does not have sufficient capacity to allow for the movement of blood and no mixing occurs. It would be appreciated that a bag, filled to capacity like an engorged tick, would be essentially refractory to mixing and no convection or other currents could be readily induced. In other words, an inner collapsible container 102 that is filled to capacity to the extent that the flexibility of the bag material is reduced beyond its ability to yield during agitation results in essentially no mixing. Accordingly, by selecting a surface to volume ratio of at least 4.85 cm$^2$/ml mixing can occur as the blood is 'sloshed' around. It would be appreciated that improper mixing leads to undesirable hemolysis of the red blood cells. Accordingly, mixing also has practical limits. The present disclosure provides for devices and methods to reduce potential hemolysis while achieving significant mixing.

In an aspect according to the present disclosure, a method of reducing the oxygen from red blood cells includes placing the red blood cells in a device according to the present disclosure and placing the device on an agitator to enhance the oxygen removal from the red blood cells. The use of agitators in the practice of blood transfusion is well known with respect to preventing clot formation, such as in the use of rocker tables and donation scale mixers when used with whole blood and suspensions of red blood cells, and also for platelet storage, wherein the platelets require oxygen for survival and agitation to prevent clumping and activation of the platelets.

With respect to currently available devices for agitating red blood cells, whether whole blood or other red blood cell suspensions, a platform is typically rotated a few degrees about a central axis to provide for a gentle rocking motion and there are many available choices commercially available. For example, Bellco Glass model #7740-10000 (Bellco Glass, Inc., Vineland, NJ) provides for 7 degrees tilt and 1 to about 12 oscillations per minute. The Medicus Health model 5277M5 nutating mixer (Medicus Health, Kentwood, MI) provides for a 20 degree angle of inclination at 24 rpm for the suspension of red blood cell samples, while another style device used at the time of donation to prevent clotting of whole blood is the Genesis blood collection mixer model CM735A (GenesisBPS, Ramsey, NJ), which provides for about 20 degrees of tilt and performs 3 cycles in about 3 seconds, then rests for about 2 seconds to weigh the sample and repeats until the desired weight is achieved. The Benchmark Scientific model B3D2300 (Benchmark Scientific, Inc., Edison, NJ) provides for a variable 0-30 degree tilt angle and 2-30 oscillations per minute.

The present disclosure further includes and provides for other available means of agitation of blood samples including orbital shakers, such as the model LOS-101 from Labocon (Labocon Systems, Ltd, Hampshire, U.K.), having a displacement of 20 mm and an oscillation rate of 20-240 rpm, or the model EW-51820-40 from Cole-Parmer (Cole-Parmer, Inc., Vernon Hills, IL) having a displacement of 20 mm and an oscillation rate of 50-250 rpm.

Devices to agitate platelets are also well known in the art and include various models such as the PF96h from Helmer Scientific (Helmer Scientific, Noblesville, IN) which provides for a linear oscillation of about 70 cycles per minute with a displacement of about 38 mm (1.5 inches), and the model PAI 200 from Terumo Penpol (Terumo Penpol Ltd., Thiruvananthapuram, India) with an oscillation of about 60 cycles per minute and a displacement of about 36 mm (1.4 inches).

While the devices of the present disclosure provide for enhanced deoxygenation of red blood cells, the use of modified motions provides for even further oxygen removal from the red blood cells. It is well known that platelets can be activated by mechanical agitation, such as shear force, and are therefore subject to limitations on how much physical agitation can be tolerated before such activation occurs. Hemolysis of red blood cells is estimated to occur at shear stress levels above approximately 6000 dyne/cm$^2$ (Grigioni et al., J. Biomech., 32:1107-1112 (1999); Sutera et al., Biophys. J., 15:1-10 (1975)) which is an order of magnitude higher than that required for platelet activation (Ramstack et al., J. Biomech., 12:113-125 (1979)). In certain aspects, currently available platelet agitators operating at about 36 mm displacement and about 65 cycles per minute (cpm) provide for deoxygenation of red blood cells as disclosed herein. In other aspects, improved rates and extent of deoxygenation without hemolysis are achieved using linear oscillating motion with a displacement of between 30 mm and about 125 mm. In another aspect, the agitation is a linear oscillation from about 50 mm to about 90 mm.

The present disclosure also provides for, and includes, adjusting the frequency of oscillation to ensure efficient mixing. In addition to platelet shakers having a displacement of about 36 mm and a frequency of about 65 cpm, in certain aspects, the frequency is from about 60 to about 150 cycles per minute (cpm). In certain aspects, the frequency of agitation is between about 80 and about 120 cpm.

In certain aspects according to the present disclosure, when using an agitator or mixer, various configurations of the chambers in a collection device 10 with more than one chamber are provided. With an agitator that moves in a horizontal motion, in one aspect, two to eight horizontal (flat on surface) chambers are arranged, side by side, end to end, one on top of the other, one on top of the other with one or more partially covering the chamber(s) beneath. In other aspects, with an agitator that moves in a vertical motion, two to eight vertical (perpendicular to surface) chambers are arranged, side by side, end to end, one on top of the other, one on top of the other with one or more partially covering the chamber(s) beneath. In another aspect, with an agitator that moves up and down traversing an angle >0 and <90 degrees to horizontal two to eight upright (>0 degrees<90 degrees to horizontal) chambers are arranged, side by side, end to end, one on top of the other, one on top of the other with one or more partially covering the chamber(s) beneath.

A further advantage of the agitation and mixing of the oxygen depletion device 10 is that the movement of the blood or blood component caused by the agitator also moves the sorbent sachet located on the top or bottom of the oxygen depletion device 10. Because the sorbent sachet is moving up and down as it rests on top, the active ingredient that absorbs the oxygen in the headspace is constantly settling. This constant movement of the active ingredient moves oxidized iron particles out of the way of non-oxidized iron particles, speeding up the oxygen absorption potential of the sorbent.

The present disclosure provides for, and includes, mixing the oxygen depletion device 10 by compression of the collapsible blood container 102. Compressing of the collapsible container 102 is achieved by applying pressure on one of the collapsible container's larger surfaces at 30 cm/sec during 1-3 seconds creating a hydrostatic pressure of 100-300 mmHg within the collapsible container, then applying a pressure to the opposite surface of the collapsible container at 10-30 cm/sec during 1-3 seconds creating a hydrostatic pressure of 100 to 300 mmHg within the collapsible container. This operation is to be performed for 2 to 4 hours.

The present disclosure provides for, and includes, mixing the oxygen depletion device 10 by massage of the collapsible blood container 102. Massaging of the collapsible container 102 is achieved by displacing a roller type device along one surface of the collapsible container completing the full translation in 1-3 seconds and making the collapsible container collapse and agitate its contents. This operation is to be performed for 1-2 hours. In another aspect, a roller travels along another surface of the collapsible container, completing the full translation in 1-3 seconds and making the collapsible container collapse and agitate its content. This operation is to be performed for 1-2 hours.

The present disclosure provides for, and includes, a blood storage device 20, for storing oxygen depleted blood and maintaining the blood in a deoxygenated state during the storage period. Certain anaerobic blood storage devices (ASB) are known in the art, including for example U.S. Pat. No. 6,162,396 to Bitensky et al. The anaerobic blood storage devices of the prior art did not include ports and inlets designed to be substantially impermeable to oxygen. Accordingly, the prior art anaerobic storage devices had poor shelf lives prior to use and were susceptible to significant ingress of oxygen. As provided in the present disclosure, an improved blood storage device 20 comprising features directed to maintaining the integrity of the device while allowing for the sampling of the blood that occurs during storage and blood banking. The improved ASB also provides for improved diffusion of oxygen from the blood, providing for additional depletion during the storage period.

The blood storage device 20 comprises an outer receptacle 201 that is substantially impermeable to oxygen, a collapsible blood container 202 comprising a locating feature 203 adapted to align the collapsible blood container 202 within the geometry of the outer receptacle 201; at least one inlet/outlet 30 comprising connecting to the collapsible blood container 202 and a bond 302 to the outer receptacle 201, wherein the bond 302 to the outer receptacle 201 is substantially impermeable to oxygen and an oxygen sorbent 207 situated within the outer receptacle 201.

As used herein, an outer receptacle 201 is at least equivalent to an outer receptacle 101. Also as used herein, an inner collapsible blood container 202 includes blood containers as provided above for an inner collapsible blood container 102 but also provides for collapsible blood containers 202 comprising materials that are less permeable to oxygen, such as PVC. Also as provided herein, oxygen sorbent 207 is at least equivalent to sorbent 103 and may be provided in sachets as discussed above.

Also included and provided for in the present disclosure are blood collecting kits. In an aspect according to the present disclosure, an oxygen depletion device for depleting oxygen from blood is included in a blood collection kit that reduces or eliminates the introduction of oxygen during the blood collection process. Blood collection kits in the art do not include any features or elements that prevent the introduction of oxygen during the collection process. Accordingly, kits in the art having multiple containers provide from about 3 cc's of residual oxygen per container, plus additional ingress through materials and fittings, and thereby increase the saturation of oxygen (sO2) from the venous oxygen saturation (SvO2) of about 40 to 60% to up to full saturation. In an aspect according to the present disclosure, the entire blood collection kit is contained in an oxygen free or oxygen reduced environment. In an aspect, the blood collection kit is contained within a kit enclosure bag that is substantially oxygen impermeable and includes within the enclosure bag an amount of oxygen sorbent absorb oxygen. Amounts of sorbent for a blood collection kit according to the present disclosure are separate from, and in addition to amounts of sorbent that may be included in a blood collection bag or anaerobic storage bag.

In certain aspects according to the present disclosure, the amount of oxygen sorbent included in a blood collection kit is sufficient to remove oxygen from a blood collection kit introduced during manufacture. In an aspect, the blood collection kit includes oxygen sorbent sufficient to absorb 10 cc's of oxygen. In another aspect, the blood collection kit includes oxygen sorbent sufficient to absorb 60 cc's of oxygen. In another aspect, the blood collection kit includes oxygen sorbent sufficient to absorb 100 cc's of oxygen. In another aspect, the blood collection kit includes oxygen sorbent sufficient to absorb 200 cc's of oxygen. In another aspect, the blood collection kit includes oxygen sorbent sufficient to absorb 500 cc's of oxygen. In another aspect, the blood collection kit includes oxygen sorbent sufficient to absorb from 10 to 500 cc's of oxygen. In another aspect, the blood collection kit includes oxygen sorbent sufficient to absorb up to 24,000 cc to allow for the management of shelf life of the device. In certain aspects according to the present disclosure, the oxygen sorbent is disposed in one or more sachets.

In an aspect, the amount of oxygen sorbent is sufficient to maintain an oxygen depleted environment for the blood collection kit during the storage. In certain aspects, oxygen is flushed from the blood collection kit during manufacture. Accordingly, the amount of oxygen sorbent may be reduced to account for leakages and residual permeability of the substantially impermeable kit enclosure bag.

Also included and provided for in the present disclosure are additive solution bags that are substantially impermeable to oxygen. In an aspect according to the present disclosure, substantially oxygen impermeable additive solution bags avoid the reintroduction of oxygen to the oxygen reduced blood after oxygen reduction in the oxygen reduction blood collection bag.

In aspects of the present disclosure, the method may further include adding an additive solution to the packed RBCs to form a suspension. In certain aspects, the additive solution may be selected from the group consisting of AS-1, AS-3 (Nutricel®), AS-5, SAGM, PAGG-SM, PAGG-GM, MAP, SOLX, ESOL, EAS61, OFAS1, and OFAS3, alone or in combination. Additive AS-1 is disclosed in Heaton et al., "Use of Adsol preservation solution for prolonged storage of low viscosity AS-1 red blood cells," Br J Haematol., 57(3): 467-78 (1984). In a further aspect, the additive solution may have a pH of from 5.0 to 9.0. In another aspect, the additive may include an antioxidant. In some aspects according the present disclosure, the antioxidant may be quercetin, alpha-tocopheral, ascorbic acid, or enzyme inhibitors for oxidases.

EXAMPLES

Example 1: Fabrication of Outer Receptacle 101

A barrier bag is fabricated by heat sealing along one edge by placing a pair of RollPrint Clearfoil® Z film #37-1275 (Rollprint Packaging Products, Inc., Addison, IL) sheets about 23×30.5 cm (9×12 inches) into a heat sealer along the shorter 23 cm length. A piece of multilayer tubing having a polyethylene outer layer, a PVC inner layer, and an intermediary bonding layer of EVA (Pexco, Inc., Athol, MA or Extrusion Alternatives, Inc., Portsmouth, NH) 0.4 cm I.D. by 0.55 cm O.D. by about 2.6 cm long is placed onto a solid brass mandrel about 0.4 cm diameter by about 2.5 cm length and then placed between the films and located in the transverse groove of the heat sealing dies heated to about 130° C. The press is activated and set to about 4 seconds duration at $21 \times 10^4$ Pascal (Pa) to create a continuous welded seal along the length of the dies, with the short piece of multilayer tubing sealed in place. The short multilayer tubing provides for an oxygen impermeable seal around the outer diameter of the tubing while also providing fluid connectivity through the seal. A piece of PVC tubing 0.3 cm I.D.×0.41 cm O.D. by about 30.5 cm length (Pexco, Inc., Athol, MA, or Extrusion Alternatives, Inc., Portsmouth, NH) is solvent bonded using cyclohexanone to the multilayer tubing from the outside of the bag.

Sealing of the two long edges of the barrier film is performed with an impulse heat sealer (McMaster Carr #2054T35, McMaster Carr, Inc., Robbinsville, NJ), leaving the last remaining short edge of the barrier bag unsealed to place a blood container 102 inside.

Example 2: Preparation of Silicone Sheets

Liquid Silicone Rubber (LSR)

Silicone sheets having a thickness of about 25 m are fabricated by mixing equal parts of a two-part silicone elastomer dispersion in a suitable solvent, such as xylene, for example NuSil MED10-6640. MED 10-6640 is supplied as a 2 part resin system. As the first step, Part A and Part B are mixed in equal measure to create the dispersion. Next, the air was removed under vacuum. The vacuum time was selected to ensure that no bubbles were left in the dispersion. Next the dispersion is spread out and passed under a precision knife edge on a custom built knife coating tray. The sheet is partially cured by heating before placing a sheet of polyester mesh fabric (Surgical Mesh, Inc., Brookfield, CT #PETKM3002) onto the partially cured silicone sheet. The polyester mesh fabric is pressed into the partially cured sheet by applying a load onto the laminate. The laminate is cured using a ramp cure using the following sequence of time and temperature combination: 30 minutes at ambient temperature and humidity, 45 minutes at 75° C. (167° F.), and 135 minutes at 150° C. (302° F.) to yield a silicone membrane 113 about 25 μm thick, and having an integrated spacer 110, whose thickness is not inclusive of the resulting silicone membrane. The polyester mesh fabric is adhered to the cured silicone membrane 113, but was not totally encapsulated by the silicone membrane 113. The one surface of the membrane 113 has a matte finish suitable for contact with blood or blood products.

Additional integrated silicone membranes having thicknesses of about 13 μm and about 50 μm are fabricated using the silicone dispersion method.

Example 3: Fabrication of an Inner Collapsible Blood Container 102

A silicone blood bag is fabricated from a pair of silicone sheets by bonding the edges together with Smooth On Sil-Poxy RTV adhesive (Smooth-On, Inc. Easton, PA) and placing the bonded sheets between a pair of flat aluminum plates to yield a silicone blood bag. A silicone inlet tube (McMaster Carr #5236K83, McMaster Carr, Inc., Robbinsville, NJ) is bonded within the seam to provide for fluid passage and nested within a groove in the aluminum plates before clamping the plates together with large binder clamps and allowing the adhesive to cure overnight. The silicone blood bag is removed from the aluminum plates the next day and leak tested by insufflating with compressed air and submerging in water to observe for bubbles before use. The silicone blood bag is then placed in an outer barrier bag fabricated as described in Example 1.

The silicone blood bag is placed inside the barrier bag as disclosed in Example 1 and the silicone inlet tube of the silicone blood bag is connected to the multilayer tube using a plastic barb fitting (McMaster Carr #5116K18, McMaster Carr, Inc., Robbinsville, NJ), and an oxygen sensor tab (Mocon #050-979, Mocon, Inc., Minneapolis, MN) is affixed to the inside of the barrier bag. A pair of plastic mesh spacers (McMaster Carr #9314T29, NJ McMaster Carr, Inc., Robbinsville, NJ) are cut to about 12.7×17.8 cm (5×7 inches) and one or more sachets of oxygen sorbent (Mitsubishi Gas Chemical America, New York, NY) are affixed near the center of each piece of plastic mesh just seconds prior to placing the plastic mesh spacers between the blood bag and barrier bag and sealing the final edge of the barrier bag with the impulse sealer. The resulting oxygen depletion device 10 is used in subsequent testing.

Example 4: Blood Preparation

Whole blood and blood products including leukoreduced whole blood and leukoreduced packed red blood cells are prepared using techniques known in the art. Samples are analyzed as indicated using a Radiometer ABL-90 hemoanalyzer (Radiometer America, Brea, CA) according to manufacturer instructions including pH, blood gas, electrolyte, metabolite, oximetry, and baseline $sO_2$, and pO2 levels. Free hemoglobin is measured using the Hemocue® Plasma Low Hb Photometer according to manufacturer instructions.

As appropriate, blood $sO_2$ levels are increased to levels typical of collected whole blood (65 to 90%) by passing the blood or blood component through a Sorin D100 oxygenator (Arvada, CO) with oxygen as the exchange gas. All experiments begin with ≥50% $sO_2$ prior to transferring the blood to an oxygen depletion device for testing.

Example 5: Test of Deoxygenation

An oxygen depletion device of Example 2 is provided with blood and tested as follows. Whole blood (124 grams) is obtained and saturated with oxygen by injecting several cc of pure oxygen gas and placed in the silicone blood bag of Example 2 by sterile transfer using a Terumo Sterile Connection Device (SCD) and weighing the bag during transfer. The outer receptacle 101 headspace oxygen level is measured using a Mocon OpTech Platinum oxygen analyzer and determined to be 1.60 torr at the start of the experiment. An initial sample of blood is taken and measured on a Radiometer ABL-90 hemoanalyzer (Radiometer America, Brea, CA) and the saturated oxygen content (sO2) found to be 98.7%. The barrier bag with blood is placed on a work bench at room temperature (21.0° C.) and allowed to stand one hour without agitation. After one hour, the sO2 is determined to be 93.5% $SO_2$ and the barrier bag headspace oxygen is determined to be 0.70 torr oxygen. The barrier bag with blood is incubated at room temperature (21.0° C.) for about 14 hours without agitation. After 14 hours incubation, the $sO_2$ is determined to be 66.7%, and a final determination of $sO_2$ is 51.2% after an additional 7 hours incubation at 21° C. without agitation. The rate of deoxygenation follows first order kinetics and the rate constant is calculated to be on the order of about $min^1$.

Example 6: Serpentine Urethane Flow Oxygen Depletion Devices

A collapsible blood bag is fabricated from breathable polyurethane film (American Polyfilm, Branford, CT) having a reported moisture vapor transmission rate of 1800 $gr/m^2/24$ hrs., wherein a serpentine tortuous flow path is fabricated using a custom heat sealing die to weld a pair of the films together to create the geometry. The collapsible bag with tortuous path comprised a series of 12 channels of about 5 mm width and 220 mm in length, providing for an overall flow path of about 2640 mm. The collapsible bag is sealed within an outer barrier according to Example 1. The resulting depletion device further includes two multilayer tubes sealed within one end, as previously described in this disclosure, such that the inlet and outlet of the tortuous path are in fluid connectivity with the pieces of multilayer tube.

Two pieces of plastic spacer mesh (McMaster Carr #9314T29, McMaster Carr, Inc., Robbinsville, NJ) are cut to about 125×180 mm (5×7 inches) and placed on both sides of the collapsible blood container within the outer barrier receptacle. A sachet of oxygen sorbent (SS-200, Mitsubishi Gas Chemical America, NY, NY) is placed between each of the plastic mesh spacers and the outer barrier receptacle (2 sachets total) and an oxygen sensor tab (Mocon #050-979, Mocon, Inc. Minneapolis, MN) before sealing the final edge of the outer barrier receptacle. A length of standard IV tubing (Qosina T4306, Qosina, Corp., Edgewood, NY) 914 mm (36 inches) is solvent bonded using cyclohexanone to each of the multilayer tubes. A ratchet clamp (Qosina #140072, Qosina, Corp., Edgewood, NY) is placed onto the outlet tubing to control flow.

A standard 500-mL blood bag (model KS-500, KS Mfg., Avon, MA) is connected to the length of outlet tubing using a Terumo sterile tubing welder (model TSCD-II, Terumo BCT, Inc., Lakewood, CO). A second standard 500-mL blood bag (model KS-500, KS Mfg., Avon, MA) is filled with 325 grams of blood at 20.8° C. and a sample measured on a Radiometer ABL-90 hemoanalyzer (Radiometer America, Brea, CA) and found to have 83.0% $SO_2$ and 70.1 mm Hg $pO_2$. A ratchet clamp (Qosina #140072, Qosina, Corp., Edgewood, NY) is placed onto the inlet tubing to control flow and the filled blood bag is then connected to the inlet tube using a Terumo sterile tubing welder (model TSCD-II, Terumo BCT, Inc., Lakewood, CO). The ratchet clamps are closed to prevent flow and the filled blood bag is hung from an IV pole such that the inlet tubing was fully extended and the collapsible blood bag is on the laboratory bench. The outlet bag is tared on a balance before it is placed on the floor with the outlet tubing fully extended. The headspace oxygen level in the outer receptacle is measured using a Mocon Op-Tech platinum oxygen analyzer and found to be 0.05 torr oxygen at the start. The clamps are opened and a stopwatch timer started to measure the duration of flow, and after 3 minutes 25 seconds the inlet blood bag is emptied and the ratchet clamps are closed. A sample of blood is taken and measured and found to have 84.1% $sO_2$ and 71.6 mmHg $pO_2$, the increase presumably from residual oxygen in the empty circuit. The headspace measured 0.00 torr oxygen and the outlet blood bag contained 277 grams of blood.

The empty inlet blood bag is removed from the IV pole and placed on the floor, while the outlet blood bag with 277 grams of blood is hung from the IV pole to repeat the flow. The IV pole is lowered to 457 mm (18 inches) to reduce the flow rate and the clamps opened to repeat the cycle. The process is repeated 5 times, and then the collapsible blood bag is filled with blood and allowed to remain stationary on the laboratory bench for 80 minutes and a terminal blood sample is taken for measurements on the hemoanalyzer. The table below summarizes the results, which show a slight gradual increase in the oxygen level of the blood during flow, with a slight decrease after standing. The results indicate that the system does not provide for an appreciable deoxygenation of the blood over the course of the study, but rather absorbs oxygen from the permeable standard PVC blood bags. From this, the importance of taking additional measures to prevent the ingress of oxygen at inlets, outlets, ports, and tubing is demonstrated.

TABLE 3

| | | | | Headspace |
|---|---|---|---|---|
| Flow Pass # | Time (min:sec) | sO$_2$% | pO$_2$ mmHg | O$_2$ torr |
| Start | n/a | 83.0 | 70.1 | 0.05 |
| 1* | 3:25 | 84.1 | 71.6 | 0.00 |
| 2 | 7:45 | 84.8 | 72.6 | 0.09 |
| 3 | 6:38 | 85.2 | 72.9 | 0.09 |
| 4 | 7:16 | 85.6 | 73.4 | 0.13 |
| 5 | 6:31 | 85.4 | 72.9 | 0.15 |
| Stagnant | 80:00 | 83.6 | 64.3 | 0.15 |

*914 mm head height; all other flow passes at 457 mm height.

Example 7: Test of Inner Collapsible Blood Container 102 Configurations

A series of inner collapsible blood containers 102 are prepared according to Table 4 below and sealed in an outer receptacle 101 as provided in Example 1. Leukoreduced packed red blood cells (LRpRBC) are introduced into the container 102. The resulting oxygen depletion devices 10 further included a Mocon Optech-O2 sensor. Assembled blood containers according to Table 4 are placed on a Helmer Labs Platelet Shaker, Model PF96 and blood and headspace samples are obtained and analyzed at time points between 0 and 300 minutes.

As shown in FIG. 5, the depletion of oxygen follows first order kinetics. The rate constants are provided in Table 5.

TABLE 5

| Rate constants | |
|---|---|
| Sample | Rate Constant (min$^{-1}$) |
| Simulation | −1.20 × 10$^{-2}$ |
| 1A | −1.00 × 10$^{-2}$ |
| 2A | −0.41 × 10$^{-2}$ |
| 3A | −0.62 × 10$^{-2}$ |
| 4A | −0.82 × 10$^{-2}$ |
| 5A | −0.93 × 10$^{-2}$ |
| 1B | −1.12 × 10$^{-2}$ |
| 2B | n/a |
| 3B | −1.40 × 10$^{-2}$ |
| 4B | −1.03 × 10$^{-2}$ |
| 5B | −1.34 × 10$^{-2}$ |
| 6B | −0.95 × 10$^{-2}$ |

Example 8: 30.5×30.5 cm (12×12 Inch) Thick Silicone Bag

A collapsible blood container 102 is fabricated from a pair of silicone sheets 152 μm thick and 228 μm thick, respectively (McMaster Carr #87315K71, McMaster Carr, Inc., Robbinsville, NJ), bonded together around the periphery Sil-Poxy silicone adhesive (Smooth-On, Inc., Easton, PA) and bonding silicone tubing (McMaster Carr #9628T42, McMaster Carr, Inc., Robbinsville, NJ) for fluid communication as an inlet tube. The bonded sheets are cured two days between clamped aluminum plates.

The collapsible blood bag inlet tube is connected with a multilayer tube of an outer receptacle barrier bag 101 according to Example 1 with a plastic barb fitting (McMaster Carr #5116K18, McMaster Carr, Inc., Robbinsville, NJ). The resulting outer receptacle bag 101 is leak tested by insufflation submersion as described in Example 1.

TABLE 4

| Inner collapsible blood container 102 test configurations | | | | | | | |
|---|---|---|---|---|---|---|---|
| Sample | LRpRBC Hct | sO$_{2i}$ | Material | Source | Thickness or Pore size | Compartments | # Sorbent Sachets* |
| 1A | >45% | >80% | Silicone | Wacker Silpuran | 30 μm | Double | 10 |
| 2A | >45% | >80% | Silicone | McMaster-Carr | 127 μm | Single | 2 |
| 3A | >45% | >80% | Silicone | Polymer Science | 76 μm | Triple | 15 |
| 4A | >45% | >80% | Silicone | Polymer Science | 76 μm | Triple | 15 |
| 5A | >45% | >80% | PVDF GVSP | Millipore | 0.22 μm | Singe | 5 |
| 1B | 52% | >50% | PVDF VVSP | Millipore | 0.22 μm | Single | 5 |
| 2B | 52% | >50% | PVDF VVSP | Millipore | 0.1 μm | Single | 5 |
| 3B | 52% | >50% | PVDF VVSP | Millipore | 1.0 μm | Single | 5 |
| 4B | 52% | >50% | Silicone | Wacker | 50 μm | Single | 5 |
| 5B | 52% | >50% | Silicone | Wacker | 20 μm | Single | 5 |
| 6B | 52% | >50% | Silicone | Polymer Science | 76 μm | Single | |

All oxygen depletion devices include an outer receptacle 101 according to Example 1.
All examples incorporate a spacer 110 to maintain headspace The device 10 is assembled with two 330×330 mm mesh spacers (McMaster Carr #9314T29, McMaster Carr, Inc., Robbinsville, NJ) and four sachets of oxygen sorbent are affixed to each mesh spacer with tape (SS-200, Mitsubishi Gas Chemical America, NY, NY), the collapsible blood container, and an oxygen sensor tab (Mocon #050-979, Mocon, Inc. Minneapolis, MN) inserted and heat sealed in the barrier bag 101. The inlet tube comprised standard IV tubing (200 mm Qosina T4306, Qosina, Corp., Edgewood, NY) is solvent bonded with cyclohexanone to the multilayer tube of barrier bag 101. A ratchet clamp (Qosina #140072, Qosina, Corp., Edgewood, NY) provides for control flow.

A pair of matched units of blood are prepared for the study by adjusting the hematocrit to 50% after centrifugation and recombining the red cells and desired amount of plasma to achieve the target hematocrit. The initial blood $SO_2$ is measured on a Radiometer ABL-90 hemoanalyzer (Radiometer America, Brea, CA) and found to have 39.0% $sO_2$; three syringes containing 30-cc of 100% oxygen were added to the blood to obtain a $SO_2$ level of 85.6% before starting the study. A portion of the blood is transferred to a tared standard 500-mL blood bag (model KS-500, KS Mfg., Avon, MA) and filled with 532 grams of blood to represent a typical 500-mL unit of donated blood having a high hematocrit and saturated oxygen level. The standard 500-mL blood bag (model KS-500, KS Mfg., Avon, MA) is connected to the length of inlet tubing using a Terumo sterile tubing welder (model TSCD-II, Terumo BCT, Inc., Lakewood, CO) and the contents transferred into the collapsible blood bag under test.

The collapsible blood bag is placed on a Helmer model PF96 platelet agitator (Helmer Scientific, Nobelsville, IN) and a sample of blood is taken and measured on a Radiometer ABL-90 hemoanalyzer (Radiometer America, Brea, CA) and the headspace oxygen level measured on a Mocon Op-Tech platinum oxygen analyzer (Mocon, Inc., Minneapolis, MN). At the beginning, the blood is found to have 84.5% $SO_2$ and the headspace oxygen partial pressure is 2.48 torr. Samples are agitated on the platelet agitator and samples taken and measured every 30 minutes for 150 minutes duration. The results are summarized in Table 6 below.

TABLE 6

| Deoxygenation using a 30.5 × 30.5 cm silicon bag | | | | |
|---|---|---|---|---|
| Time (min) | $sO_2\%$ | $pO_2$ mmHg | $pCO_2$ mmHg | Headspace $O_2$ torr |
| 0 | 84.5 | 63.9 | 88.9 | 2.48 |
| 30 | 70.3 | 40.0 | 50.7 | 4.63 |
| 60 | 64.9 | 34.9 | 43.6 | 5.24 |

The calculated deoxygenation rate constant is $-0.34 \times 10^{-2}$ $min^{-1}$.

Example 9: Effect of Mixing on Oxygen Depletion

Four oxygen reduction bags (ORB), having a silicone inner collapsible blood container 102, are prepared according to Example 3. The inner collapsible blood container 102, is filled with leukocyte reduced packed red blood cells (LRPRBC), prepared according to Example 4, to obtain a surface area to volume (SAV) ratio of approximately 6 $cm^2/ml$. Three LRPRBC filled ORBs are placed flat on a Helmer PF-96 Platelet Agitator (Noblesville, IN) or a PF-8 agitator, with the standard cycles per minute (72 cpm) or modified to a reduced-standard cpm (42 cpm) linear oscillation. A third set of filled ORB's are placed on a Benchmark 3D 5RVH6 agitator (Sayretville, NJ). Samples are collected and analyzed at 0, 60, 120, and 180 mins for various ABL-90 outputs outlined in Example 4.

As shown in FIG. 12, 3D mixing results in the highest rate of oxygen depletion and the lowest percent $SO_2$ at $T_{180}$ compared to the linear oscillation method of mixing. Further, a higher rate of oxygen depletion is obtained with the standard cpm linear oscillation (SLO) compared to the reduced-standard cpm linear oscillation (R-SLO).

Example 10: Effect of Surface to Volume Ratios on Oxygen Depletion

In another example, six oxygen reduction bags (ORB), having an inner collapsible blood container 102, are prepared with Bentec silicone. LRPRBC is collected and prepared according to Example 4. The silicone inner collapsible blood containers 102, are filled with 176, 220, 250, 270, 300, and 350 mL of LRPRBC, to provide the surface to area ratios between 3.41-6.8 $cm^2/ml$ as shown in Table 7. The percent $sO_2$ is measured in the ORBs containing the various LRPRBC volumes at 0, 30, 60, 120, and 180 mins as described in Example 4.

TABLE 7

| Surface Area to Volume Ratio | | | | | | |
|---|---|---|---|---|---|---|
| Blood Volume (ml) | 176 | 220 | 250 | 270 | 300 | 350 |
| SAV Ratio ($cm^2$/ml) | 6.8 | 5.45 | 4.8 | 4.4 | 4 | 3.41 |

As shown in FIG. 13, the surface area kinetic rates decrease once the SAV ratio is below 5.45 $cm^2/ml$.

In another example, five oxygen reduction bags (ORB), having an inner collapsible blood container 102, are prepared with PVDF instead of silicone. LRPRBC is collected and prepared according to Example 4. The PVDF inner collapsible blood containers 102 are filled with 95, 110, 220, 300, or 360 ml blood volume, to provide the surface area to volume ratios shown in Table 8. The percent $sO_2$ is measured in the ORBs containing the various LRPRBC volumes at 0, 30, 60, 120, and 180 mins as described in Example 4.

As shown in FIG. 14, the lowest percent $sO_2$ after 180 mins is achieved when the SAV ratio is above 5.

TABLE 8

| Surface Area to Volume Ratio | | | | | |
|---|---|---|---|---|---|
| Blood Volume (ml) | 95 | 110 | 220 | 300 | 360 |
| SAV Ratio ($cm^2$/ml) | 6.8 | 5.9 | 2.9 | 2.2 | 1.8 |
| Kinetic Rate (×100) | −1.39 | −1.9 | −0.82 | −0.06 | −0.32 |

In another example, four oxygen reduction bags (ORB), having single or double sided membranes (PSU or PVDF) are prepared. LRPRBC is collected and prepared according to Example 4. The inner collapsible blood containers 102 are filled with 112-118 ml LRPRBC, to provide a 50% reduction in surface area volume in the double sided membrane. The percent $sO_2$ is measured in the ORBs containing the single or double membrane as described in Example 4. As shown in FIG. 15, a 50% reduction in surface area results in a 50-60% reduction in the overall kinetic rate.

Example 11: Preparation of Collapsible Blood Containers from Microporous Polysulfone or PVDF Heat sealed polysulfone and PVDF oxygen permeable collapsible blood containers 102 are prepared. The prepared seal results in the breakdown of the microporous structure of the films to produce a crystalline area that is sensitive to the flexural stresses associated with fluid movement in the resulting containers 102. The containers 102 are subject to leakage and breakage and are not suitable for ORB's intended for use outside of an experimental setting.

To overcome the inability to heat seal polysulfone or PVDF membranes in a manner suitable for use in transfusion medicine, a heat laminable "tie" layer 105 is included in the construction of the containers 102 prepared from microporous membranes 113. As shown in FIG. 9B, the seal area is reinforced by pre-laminating low density polyethylene (LDPE) strips to the inside surfaces of the upper and lower membranes to align with the bag seal area. The pre-lamination results in pre-laminate seals 107 as shown in FIG. 9B. The two pre-laminated membranes 113 (114) are then heat sealed to form the seal 108 as shown in FIG. 9B. Also as shown in FIG. 9B, the tie layers extend beyond the width of the seal by an amount.

LDPE melts at about 105° C., well below the melting temperatures of polysulfone (187° C.) or PVDF (177° C.). The bag is completed by aligning the seal areas and heat sealing the upper and lower membranes together to form a bag. Without being limited to a specific mechanism, it is believed that the LDPE flows into the membrane pores, acting as a reinforcing strain relief inboard of the seal and a low temperature "tie" layer for the seal.

In addition to strengthening the seal between the microporous membranes 113, the tie layer also serves as a geometric feature 121. Thus the overall internal geometry can be readily adjusted by selecting the shape of the tie layers 105. Examples of exemplary geometries are shown in FIG. 10. As shown, the geometric feature 121 provides a rounded internal geometry thereby avoiding reduced mixing associated with corners. As shown in FIG. 10, the resulting container 102 can be oval or round and may further include a mixing feature 119 which provides for a circular flow of blood product and enhances mixing.

An inner collapsible blood bag is fabricated from a pair of Millipore PVDF membranes having 0.22 μm pore size, 177×177 mm square, by first heat bonding a low density polyethylene (LDPE) tie layer frame to each membrane. The LDPE tie layer frame has a thickness of about 0.02-0.10 mm and is about 177×177 mm square on the outside dimensions and has an inside dimension that is about 160×160 mm square for use with a 15 mm wide seal, thereby providing for about 4 mm of overlap between the edge of the seal and the end of the tie layer to provide stress relief in the seal edge. The tie layer frame is heat bonded to the PVDF membrane using an impulse heat sealer. The pair of tie layer bonded membranes are then heat sealed together around their periphery using a pair of custom fabricated constant heat aluminum dies having a tube sealing groove, as previously described, to yield an inner collapsible blood container. A pair of Conwed Thermanet part #R03470 polymer integrating mesh sheets are cut to approximately 10 mm larger than the inner collapsible blood bag periphery and placed on both sides of the inner collapsible blood bag with the adhesive sides of the polymer integrating mesh in contact with the inner collapsible blood bag. The assembly is placed between a pair of aluminum plates and heated to about 93-110° C., up to as much as 120° C., for about 3-15 minutes to melt the adhesive and allow it to flow into the pores of the PVDF membrane directly underneath the integrating polymer mesh, and also around the periphery of the inner collapsible blood bag where the polymer integrating mesh is in contact with itself, thereby providing a strong mechanical bond. The assembly is allowed to cool below about 50° C. before removing the plates.

Example 12: Effect of Spacer 110 on Deoxygenation Rates

Inner collapsible blood bag and oxygen depletion device are according the examples above with and without a spacer 110 according to the present disclosure. As shown in FIG. 16, incorporation of a spacer 110 significantly increases the rate of oxygen depletion.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. A method to prepare oxygen-reduced blood for storage comprising:

providing an oxygen depletion device 10 comprising:
  an outer receptacle 101 substantially impermeable to oxygen;
  an inner collapsible blood container 102 comprising one or more chambers that are permeable to oxygen;
  a non-sachet spacer 110 situated between the outer receptacle 101 and the inner collapsible blood container 102, wherein the non-sachet spacer 110 is a mesh or mat comprising at least one interstice 111 and maintains a headspace defined by the outer receptacle 101 and the inner collapsible blood container 102, wherein the at least one interstice 111 comprises between 50% to 80% of the total area of the mesh or mat material of the non-sachet spacer 110;
  an oxygen or oxygen and carbon dioxide sorbent 103 situated within a sachet and within the headspace; and
flowing the blood into the inner collapsible blood container 102 of the oxygen depletion device 10; and
producing oxygen-reduced blood having less than 20% oxygen saturation.

2. The method of claim 1, wherein the blood is selected from the group consisting of whole blood, leukoreduced red blood cells (RBCs), platelet reduced RBCs, and leukoreduced and platelet reduced RBCs.

3. The method of claim 1, wherein the inner collapsible blood container 102 comprises a first and second membrane joined by a peripheral tie layer consisting of silicone.

4. The method of claim 1, wherein the oxygen depletion device 10 further comprises a. an oxygen indicator 104 situated between the outer receptacle 101 and the inner collapsible blood container 102;
b. at least one inlet/outlet 30 passing through the outer receptacle 101 comprising a tube 301, a bond 302, and a port 303, wherein the tube 301 and the bond 302 are substantially impermeable to oxygen, and wherein the at least one inlet/outlet 30 is in fluid communication with the inner collapsible blood container 102; or c. both a and b.

5. The method of claim 1, wherein blood collected in the oxygen depletion device 10 is deoxygenated at a rate constant of at least $-0.5 \times 10^{-2}$ min$^{-1}$.

6. The method of claim 1, further comprising storing the oxygen-reduced blood at a storage temperature of between 2° C. and 6° C. for up to 64 days.

7. The method of claim 1, further comprising agitating the oxygen depletion device 10 after the flowing for up to 4 hours.

8. The method of claim 7, wherein the agitating comprises 3D mixing or linear oscillation mixing.

9. The method of claim 1, wherein a. the headspace has a volume that is between 10 and 500 milliliters (ml);

b. the at least one interstice 111 comprises between 60% to 75% of the total area of the mesh or mat material of the non-sachet spacer 110; or c. both a and b.

10. A method to prepare stored oxygen-reduced blood comprising:

providing an oxygen depletion device 10 comprising:

an outer receptacle 101 substantially impermeable to oxygen;

an inner collapsible blood container 102 comprising one or more chambers that are permeable to oxygen;

a non-sachet spacer 110 situated between the outer receptacle 101 and the inner collapsible blood container 102, wherein the non-sachet spacer 110 is a mesh or mat comprising at least one interstice 111 and maintains a headspace defined by the outer receptacle 101 and the inner collapsible blood container 102, wherein the at least one interstice 111 comprises between 50% to 80% of the total area of the mesh or mat material of the non-sachet spacer 110; and an oxygen or oxygen and carbon dioxide sorbent 103 situated within a sachet and disposed within the headspace, wherein the non-sachet spacer 110 does not enclose the oxygen or oxygen and carbon dioxide sorbent 103;

flowing the blood into the inner collapsible blood container 102 of the oxygen depletion device 10;

producing oxygen-reduced blood having less than 20% oxygen saturation; and storing the oxygen-reduced blood in the oxygen depletion device 10.

11. The method of claim 10, wherein the mat is selected from the group consisting of a molded mat, a woven mat, a non-woven mat, a strand veil, and a strand mat.

12. The method of claim 10, wherein the storing is at a storage temperature of between 2° C. and 6° C. for up to 64 days.

13. The method of claim 10, further comprising agitating the oxygen depletion device 10 after the flowing for up to 4 hours.

14. The method of claim 10, wherein a. the headspace has a volume that is between 10 and 500 milliliters (ml);

b. the at least one interstice 111 comprises between 60% to 75% of the total area of the mesh or mat material of the non-sachet spacer 110; or c. both a and b.

15. A method to prepare oxygen-reduced blood for storage comprising:

providing an oxygen depletion device 10 comprising:

an outer receptacle 101 substantially impermeable to oxygen;

an inner collapsible blood container 102 comprising one or more chambers comprising polyvinyl chloride (PVC) or polyolefin;

a spacer 110 situated between the outer receptacle 101 and the inner collapsible blood container 102, wherein the spacer 110 is a mesh or mat comprising at least one interstice 111 and maintains a headspace defined by the outer receptacle 101 and the inner collapsible blood container 102, wherein the at least one interstice 111 comprises between 50% to 80% of the total area of the mesh or mat material of the spacer 110;

an oxygen sorbent 103 disposed within the headspace, wherein the headspace ensures efficient diffusion of oxygen from a surface of the inner collapsible blood container 102 to the oxygen sorbent 103;

flowing the blood into the inner collapsible blood container 102 of the oxygen depletion device 10; and producing oxygen-reduced blood having less than 20% oxygen saturation.

16. The method of claim 15, wherein the inner collapsible blood container 102 comprises a material selected from the group consisting of a multilayered membrane, PVC comprising a citrate plasticizer, at least one layer consisting of polyester, PVC comprising a di(2-ethylhexyl) phthalate (DEHP) plasticizer, a mixing structure, and a hydrophobic microporous membrane.

17. The method of claim 15, wherein the oxygen sorbent 103 is an oxygen and carbon dioxide sorbent 103.

18. The method of claim 15, wherein the inner collapsible blood container 102 has a surface area to volume ratio of at least 4.48 centimeters$^2$/milliliter (cm$^2$/ml) when filled with a unit of blood for oxygen depletion and enclosed within the outer receptacle 101.

19. The method of claim 15, further comprising storing the oxygen-reduced blood at a storage temperature of between 2° C. and 6° C. for up to 64 days.

20. The method of claim 15, wherein the blood is selected from the group consisting of whole blood, leukoreduced red blood cells (RBCs), platelet reduced RBCs, and leukoreduced and platelet reduced RBCs.

\* \* \* \* \*